US009212211B2

(12) United States Patent
Hill et al.

(10) Patent No.: US 9,212,211 B2
(45) Date of Patent: *Dec. 15, 2015

(54) TRAIL COLLECTIN FUSION PROTEINS

(71) Applicant: APOGENIX GMBH, Heidelberg (DE)

(72) Inventors: Oliver Hill, Neckarsteinach (DE);
Christian Gieffers, Dossenheim (DE);
Meinolf Thiemann, Schriesheim (DE);
Marcus Branschädel, Heidelberg (DE)

(73) Assignee: APOGENIX GMBH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/322,830

(22) Filed: Jul. 2, 2014

(65) Prior Publication Data

US 2015/0126709 A1  May 7, 2015

Related U.S. Application Data

(63) Continuation of application No. 13/776,559, filed on Feb. 25, 2013, now Pat. No. 8,907,063, which is a continuation of application No. 12/668,188, filed as application No. PCT/EP2008/005644 on Jul. 10, 2008, now Pat. No. 8,383,774.

(30) Foreign Application Priority Data

Jul. 10, 2007 (EP) .................................... 07013506

(51) Int. Cl.
  *C07K 14/525* (2006.01)
  *C07K 14/42* (2006.01)
  *C07K 14/47* (2006.01)
  *C12N 15/62* (2006.01)

(52) U.S. Cl.
  CPC .............. *C07K 14/525* (2013.01); *C07K 14/42* (2013.01); *C07K 14/4726* (2013.01); *C12N 15/62* (2013.01); *C07K 2319/00* (2013.01); *C07K 2319/32* (2013.01)

(58) Field of Classification Search
  CPC .. C07K 14/525; C07K 14/42; C07K 14/4726; C07K 2319/00; C07K 2319/32; C12N 15/62
  See application file for complete search history.

(56) References Cited

U.S. PATENT DOCUMENTS

| 2003/0119149 A1 | 6/2003 | Reddy |
| 2004/0047873 A1 | 3/2004 | Al-Shamkhani et al. |
| 2004/0197876 A1 | 10/2004 | Tschopp et al. |
| 2004/0247563 A1 | 12/2004 | Lynch et al. |
| 2009/0325867 A1 | 12/2009 | Cohen et al. |
| 2010/0322922 A1 | 12/2010 | Martin Villalba et al. |
| 2012/0041181 A1 | 2/2012 | Hill et al. |

FOREIGN PATENT DOCUMENTS

| JP | H10-500298 A | 1/1998 |
| JP | 2003518949 A | 6/2003 |
| WO | 9531540 A1 | 11/1995 |
| WO | 9701633 A1 | 1/1997 |
| WO | 0142298 A1 | 6/2001 |
| WO | 02090553 A2 | 11/2002 |
| WO | 03060072 A2 | 7/2003 |
| WO | 03086301 A2 | 10/2003 |
| WO | 2004024925 A2 | 3/2004 |
| WO | 2007102690 A1 | 9/2007 |

OTHER PUBLICATIONS

Wu X, et al., Molecular Immunology. 46:2381-2388, 2009.*
European Search Report of European Application No. EP 12166865.1, mailed Jul. 4, 2012.
Hakansson, K. and K.B. Reid; "Collectin Structure: A Review [In Process Citation]"; Protein Science; vol. 9, pp. 1607-1617 (2000).
Haswell, L.E. et al.; "Analysis of the Oligomeric Requirement for Signaling by CD40 Using Soluble Multimeric Forms of its Ligand, CD154"; European Journal of Immunology; vol. 31, No. 10, pp. 3094-3100 (Oct. 1, 2001).
Hoppe, H.-J. et al.; "A Parallel Three Stranded Alpha-Helical Bundle at the Nucleation Site of Collagen Triple-Helix Formation"; FEBS Letters; vol. 344, No. 2/03, pp. 191-195 (Jan. 1, 1994).
International Search Report and Written Opinion of PCT Application No. PCT/EP2008/005644, mailed Jan. 26, 2009.
Kishore, et al.; "Surfactant Proteins SP-A and SP-D: Structure, Function and Receptors"; Molecular Immunology; vol. 43, pp. 1293-1315 (2006).
Kornbluth, R.S. et al.; "CD40L (CD154) Fusion Protein with Pulmonary Surfactant Protein D as a Prototype for Soluble Multimeric TNF Superfamily Ligand Molucules"; FASEB Journal, Fed. Of American Soc. For Experimental Biology; vol. 14, No. 6, p. A1162 (Apr. 20, 2000).
Sano, H. and Y. Kuroki; "The Lung Collectins, SP-A and SP-D, Modulate Pulmonary Innate Immunity"; vol. 42, pp. 279-287 (2005).
Wu, X., et al.; "Trimeric Coiled-Coil Domain of Human Pulmonary Surfactant Protein D Enhances Zinc-Binding Ability and Biologic Activity of Soluble TRAIL"; Molecular Immunology; vol. 46, pp. 2381-2388 (2009).
Crouch, Erika, et al., "Contributions of Phenylalanine 335 to Ligand Recognition by Human Surfactant Protein D: Ring Interactions with SP-D Ligands", The Journal of Biological Chemistry (Apr. 2006), vol. 281, No. 26, p. 18008-18014.

(Continued)

*Primary Examiner* — Robert Landsman
(74) *Attorney, Agent, or Firm* — Perkins Coie LLP; Viola T. Kung

(57) ABSTRACT

The present invention refers to a fusion protein comprising a TNF-superfamily (TNFSF) cytokine or a receptor binding domain thereof fused to a collectin trimerization domain, to a nucleic acid molecule encoding the fusion protein, and to a cell comprising the nucleic acid molecule. The fusion protein is present as a trimeric complex or as an oligomer thereof. The fusion protein, the nucleic acid, and the cell is suitable as pharmaceutical composition or for therapeutic, diagnostic and/or research applications.

25 Claims, 34 Drawing Sheets

(56) References Cited

OTHER PUBLICATIONS

Holler, N. et al., "Two Adjacent Trimeric Fas Ligands are Required for Fas Signaling and Formation of a Death-Inducing Signaling Complex", Molecular Cell Biology, American Society for Microbiology; (Feb. 2003) vol. 23, No. 4, pp. 1428-1440.

Sissoeff, L. et al., "Stable Trimerization of Recombinant Rabies Virus Glycoprotein Ectodomain is Required for Interaction with the p75NTR Receptor", Journal of General Virology (2005), vol. 86, No. 9, pp. 2543-2552.

Crystal structure of trail-DR5 complex, 1 D4V, Protein Data Bank, 1999 [retrieved on Apr. 30, 2014], URL, http://www.rcsb.org/pdb/explore/explore.do?structureId=1D4V.

Crystal Structure of Human CD40 Ligand, 1ALY, Protein Data Bank, 1997 [retrieved on Apr. 30, 2015], URL, http://www.rcsb.org/pdb/explore/explore.do?structureId=1ALY.

* cited by examiner

SEC of affinity purified CD95L-ASPD

Silver gel of SEC fractions A1-A11 from affinity purified CD95L-ASPD

Caspase activity on Jurkat cells induced by SEC fractions A1-A15 from affinity purified CD95L-ASPD Cytotoxicity of CD95L-ASPD on WM35, HT1080 and HeLa cells

SEC of affinity purified LIGHT-ASPD

Binding of HVEM-Fc to immobilized LIGHT-ASPD

Western blot from transiently transfected HEK cells transiently transfected with TRAIL-constructs Caspase activity in Jurkat T-cells Size exclusion chromatography of TRAIL-ASPD Cytotoxic activity of TRAIL-ASPD against human cancer cells

TRAIL-ASPD induced caspase activity in Jurkat

Cytotoxicity assay with TRAIL-ASPD or TRAIL-DSPD on HT1080 cells

Western blot from transiently transfected HEK cells transiently transfected with TRAIL-SPD-constructs or TRAIL-receptor selective SPD constructs.

TRAIL-Receptor selective ligands (TRAILR1mut and TRAILR2mut) immobilized on Streptactin plates, are differentially detected by TRAIL-Receptor 1-Fc or TRAIL-Receptor 2-Fc

A

B

C

D

Binding of TRAIL-Receptors to Receptor-selective "mutein" ligands

Size exclusion chromatography of affinity purified TRAILR1mut-ASPD

Silver stained SDS-PAGE of SEC fractions A1-A14 from affinity purified TRAILR1mut-ASPD Caspase activity of SEC fractions A1-A14 from affinity purified TRAILR1mut-ASPD on Jurkat cells Size exclusion chromatography of affinity purified TRAILR2mut-ASPD Silver stained SDS-PAGE of SEC fractions A1-A14 from affinity purified TRAILR2mut-ASPD Jurkat Kill Assay Jurkat of SEC fractions A1-A14 from affinity purified TRAILR2mut-ASPD Cytotoxic activity of TRAIL-ASPD, TRAILR1mut-ASPD and TRAILR2mut-ASPD on human cancer cells.

Receptor selective TRAIL-SPD proteins are highly souble

SEC of affinity purified TRAIL-ASPD_F335A

Silver stained SDS-PAGE of SEC fractions A1-A13

Cytotoxic effect of TRAIL-ASPD_F335A on human cancer cells

SEC of affinity purified TRAIL-ASPD_F335D

Silver stained SDS-PAGE of SEC from affinity purified TRAIL-ASPD_F335D

Cytotoxic effect TRAIL-SPD_F335D on human cancer cells

Binding of TRAIL-ASPD fusion protein to carbohydrates

Pharmacokinetics of TRAIL-ASPD (A) or TRAIL-ASPD_F335 D (B) Fusion Proteins

Caspase activity in primary human hepatocytes

Western Blot of supernatants from HEK293 cells transiently transfected with trimerized APRIL constructs TACI-Fc binds to APRIL-ASPD

TRAIL COLLECTIN FUSION PROTEINS

This application is a continuation application of U.S. application Ser. No. 13/776,559, filed Feb. 25, 2013, now U.S. Pat. No. 8,907,063; which is a continuation application of U.S. application Ser. No. 12/668,188, filed Mar. 24, 2010, now U.S. Pat. No. 8,383,774; which is a National Stage of International Application PCT/EP2008/005644, filed Jul. 8, 2008, published Jan. 15, 2009, under PCT Article 21(2) in English; which claims the priority of Application No. EP07013506.6, filed Jul. 10, 2007. The above applications are incorporated herein by reference in their entireties.

REFERENCE TO ELECTRONIC SEQUENCE LISTING FILE

This application includes a sequence listing submitted electronically herewith as an ASCII text file named "sequence.txt", which is 119 kB in size and was created Feb. 25, 2013; the electronic sequence listing is incorporated herein by reference in its entirety.

FIELD OF INVENTION

The present invention refers to a fusion protein comprising a TNF-superfamily (TNFSF) cytokine or a receptor binding domain thereof fused to a collectin trimerization domain, to a nucleic acid molecule encoding the fusion protein, and to a cell comprising the nucleic acid molecule. The fusion protein is present as a trimeric complex or as an oligomer thereof. The fusion protein, the nucleic acid, and the cell is suitable as pharmaceutical composition or for therapeutic, diagnostic and/or research applications as described herein.

STATE OF THE ART

Ligands of the tumor necrosis factor (TNF) family fulfill crucial roles in the immune system, but have also been implicated in the development of epithelial and endothelial structures.[1] TNF family ligands are primarily expressed as trimeric type II transmembrane proteins and are often processed into soluble variants that are also organized as trimers.[1,2] While shedding of some TNF ligands does not interfere with their capability to activate their corresponding receptors and might be even important for their physiological function, other TNF ligands become inactivated by proteolytic processing.[2] Soluble TNF ligands that are not or only poorly active still interact with their cognate receptors. For example, the soluble forms of TNF, CD95L, TRAIL and CD40L interact with TNFR2, CD95, TRAILR2 and CD40, respectively, but do not or only poorly activate signaling by these receptors.[3-6] Notably, inactive or poorly active soluble TNF ligands can be converted into highly active molecules by artificially increasing their avidity. For example, soluble Flag-tagged variants of TNF, CD95L, TRAIL and CD40L stimulate robust signaling by TNFR2, CD95, TRAILR2 and CD40, respectively, provided they were crosslinked with the Flag-specific mAb M2. Likewise, hexameric and dodecameric fusion proteins of soluble CD95L and soluble CD40L as well as non-specifically aggregated preparations of TNF ligands produced in *E. coli* display high activity.[6-8]

The structural hall mark of the ligands of the TNF family is the carboxy-terminal "TNF 2 homology domain" (THD) or "receptor binding domain" (RBD), both terms are equally used herein, which is part of both the transmembrane and soluble forms of TNF ligands.[1,2] The THDs of the various TNF ligands are composed of a framework of aromatic and hydrophobic residues that adopt an almost identical tertiary fold and cause self association into trimers.[1,2] The THD also mediates receptor binding. In general, trimeric ligands of the TNF family bind to three molecules of their corresponding receptor(s). This interaction alone is not necessarily sufficient to activate receptor-associated intracellular signaling pathways. Several lines of evidence suggest that the initial formation of trimeric signaling competent ligand receptor complexes is followed by secondary multimerization into supramolecular clusters.[9-11] These two steps in TNF receptor activation (1. ligand binding; 2. secondary aggregation of receptor ligand complexes) depend to a varying extent on several factors including lipid raft localization, cytoskeleton support, receptor autoaggregation, receptor associated adapter proteins, but also on affinity and avidity of the ligand receptor interaction and the way how the ligand is presented to the receptor (membrane ligand or immobilized ligand versus soluble ligand, trimers versus higher aggregates).

It is known that trimeric complexes of TNF superfamily cytokines are difficult to prepare from recombinant monomeric units.

For example, WO 01/49866 discloses recombinant fusion proteins comprising a TNF cytokine and a multimerization component. A disadvantage of these fusion proteins is, however, that the trimerization domain usually has a large molecular weight and/or that the trimerization is rather inefficient.

Schneider et al. (J Exp Med 187 (1989), 1205-1213) describes that trimers of TNF cytokines are stabilized by N-terminally positioned stabilization motifs. In CD95L, the stabilization of the CD95L-receptor binding domain trimer is presumably caused by N-terminal amino acid domains which are located near the cytoplasmic membrane.

Shiraishi et al. (Biochem Biophys Res Commun 322 (2004), 197-202) describes that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of hepta-d-repeats in the coiled-coil zipper motif are difficult to determine. In addition, coiled-coil structures have the tendency to form macromolecular aggregates after alteration of pH and/or ionic strength.

Mc Alinden et al. (J of Biol Chem, 2002, 277(43):41274-41281) discloses the preparation of a fusion protein between a human type IIA procollagen amino acid sequence and a 14 amino acid sequence corresponding to the first two heptad repeats of the rat surfactant protein's (SP-D) neck domain.

WO 01/42298 discloses the preparation of a fusion protein between surfactant protein-D comprising the signal sequence, the collagen domain and the neck domain and CD40L. The disadvantage of those fusion proteins is that they lead to multimeric aggregates that are highly immunogenic and that they do not produce functionally defined trimeric ligands.

It was an object of the present invention to provide fusion proteins comprising a TNF cytokine or a receptor binding domain, which allow efficient recombinant manufacture combined with good trimerization properties and improved pharmaceutical properties.

SUMMARY OF THE INVENTION

The present invention relates to a fusion protein comprising (i) a TNF-superfamily cytokine or a receptor binding domain thereof, and
(ii) a collectin trimerization domain.

The invention further relates to a nucleic acid molecule encoding a fusion protein as described herein and to a cell or a non-human organism transformed or transfected with a nucleic acid molecule as described herein.

The invention also relates to a pharmaceutical or diagnostic composition comprising as an active agent a fusion protein, a nucleic acid molecule, or a cell as described herein.

The invention also relates to a fusion protein, a nucleic acid molecule, or a cell as described herein for use in therapy, e.g., the use of a fusion protein, a nucleic acid molecule, or a cell as described herein for the preparation of a pharmaceutical composition in the prophylaxis and/or treatment of proliferative disorders, particularly disorders caused by, associated with and/or accompanied by dysfunction of TNF cytokines, such as tumors, e.g. solid or lymphatic tumors, infectious diseases, inflammatory diseases, metabolic diseases, autoimmune disorders, e.g. rheumatoid and/or arthritic diseases, degenerative diseases, e.g. neurodegenerative diseases such as multiple sclerosis, apoptosis-associated diseases and transplant rejections.

DETAILED DESCRIPTION OF THE INVENTION

Figure 1:
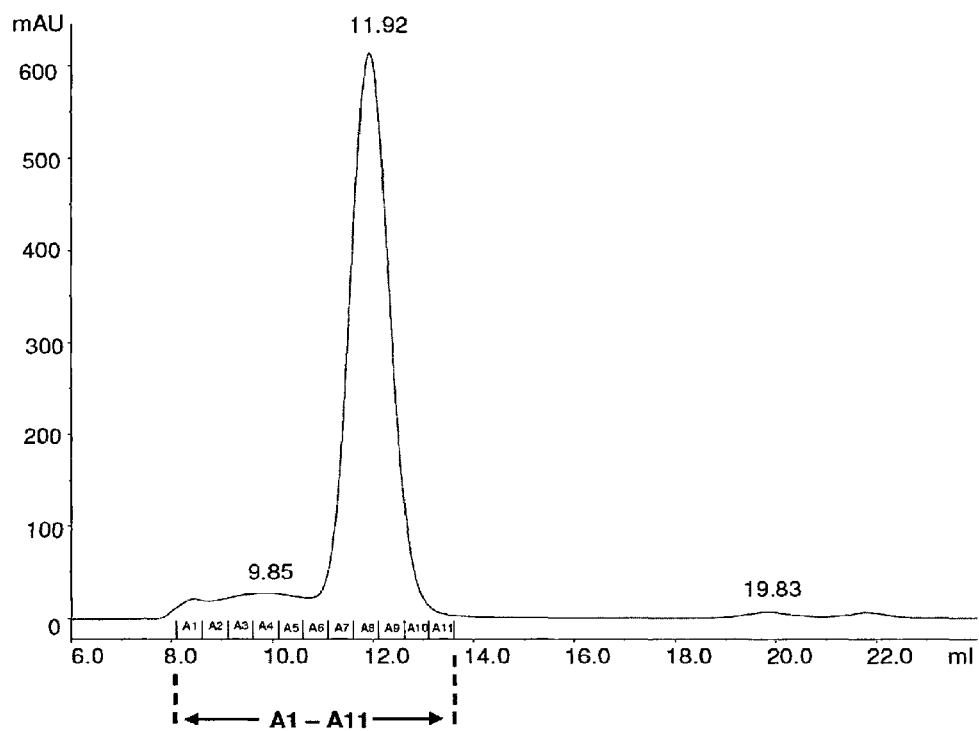
FIG. 1 shows SEC of affinity purified CD95L-ASPD.

The fusion protein may be a monomeric protein or a multimeric protein. Preferably, the fusion protein is present as a trimeric complex consisting of three monomeric units which may be identical or different. Preferably, a trimeric complex consists of three identical fusion proteins. In a further preferred embodiment, the complex is formed by covalent linkage between three of the fusion proteins described herein, e.g., a covalent linkage of disulfide bridges between cysteines of the collectin trimerization domain (ii) as described herein. The trimeric complex as such shows biological activity. It was found, however, that oligomers of the trimeric complex, e.g. defined complexes wherein the basic trimeric structure is present 2, 3 or 4 times, also have biological activity. Thus, also preferred is an oligomer of the trimeric complex.

One component (i) of the fusion protein is a cytokine of the TNF superfamily or a receptor binding domain thereof. Preferably, component (i) is a mammalian, particularly human cytokine or a receptor binding domain thereof including allelic variants and/or derivatives thereof. Further, it is preferred that the TNF cytokine is a receptor binding domain thereof capable of binding to the corresponding cytokine receptor and preferably capable of receptor activation, whereby apoptotic or proliferative activity may be caused. The cytokine may e.g. be selected from TNF superfamily members, e.g. human TNFSF-1 to -18 as indicated in Table 1, preferably from LTA (SEQ ID NO:1), TNFα (SEQ ID NO:2), LTB (SEQ ID NO:3), OX40L (SEQ ID NO:4), CD40L (SEQ ID NO:5), CD95L (SEQ ID NO:6), CD27L (SEQ ID NO:7), CD30L (SEQ ID NO:8), CD137L (SEQ ID NO:9), TRAIL (SEQ ID NO:10), RANKL (SEQ ID NO:11), TWEAK (SEQ ID NO:12), APRIL 1 (SEQ ID NO:13), APRIL 2 (SEQ ID NO:14), BAFF (SEQ ID NO:15), LIGHT (SEQ ID NO:16), TL1A (SEQ ID NO:17), GITRL (SEQ ID NO:18), EDA-A1 (SEQ ID NO:19), EDA-A2 (SEQ ID NO:20), or a receptor binding domain thereof. Preferred receptor binding domains of the respective proteins are indicated in Table 1 (NH$_2$-aa to COOH-aa) and comprise, e.g., comprises amino acids 59-205 or 60-205 of LTA (SEQ ID NO:1), 86-233 of TNFα (SEQ ID NO:2), 82-244 or 86-244 of LTB (SEQ ID NO:3), 52-183 or 55-183 of OX40L (SEQ ID NO:4), 112-261 or 117-261 of CD40L (SEQ ID NO:5), 51-193 or 56-193 of CD27L (SEQ ID NO:7), 97-234, 98-234 or 102-234 of CD30L (SEQ ID NO:8), 86-254 of CD137L (SEQ ID NO:9), 161-317 of RANKL (SEQ ID NO:11), 103-249, 104-249 or 105-249 of TWEAK (SEQ ID NO:12), 112-247 or 113-247 of APRIL 1 (SEQ ID NO:13), 112-250 or 113-250 of APRIL 2 (SEQ ID NO:14), 140-285 of BAFF (SEQ ID NO:15), 91-240 of LIGHT (SEQ ID NO:16), 91-251 or 93-251 of TL1A (SEQ ID NO:17), 52-177 of GITRL (SEQ ID NO:18), 245-391 of EDA-A1 (SEQ ID NO:19), 245-389 of EDA-A2 (SEQ ID NO:20).

More preferably, the cytokine of the TNF superfamily or a receptor binding domain thereof is selected from CD95L or TRAIL or a receptor binding domain thereof. In an especially preferred embodiment, the cytokine of the TNF superfamily or a receptor binding domain thereof comprises the extracellular portion of a TNF cytokine including the receptor binding domain without membrane located domains.

In a preferred embodiment, the cytokine of the TNF superfamily or a receptor binding domain thereof of the fusion protein is selected from human CD95L (SEQ ID NO:6), particularly amino acids 142-281 or 144-281 of human CD95L.

In a further preferred embodiment, the cytokine of the TNF superfamily or a receptor binding domain thereof of the fusion protein is selected from human TRAIL (SEQ ID NO:10), particularly amino acids 95-281, 116-281, 117-281, 118-281, 119-281 or 120-281 of human TRAIL. In another preferred embodiment human TRAIL comprise any amino acid from 95-120 as initial amino acid—amino acid 281 of SEQ ID NO:10.

In a further preferred embodiment of the invention, the cytokine of the TNF superfamily or a receptor binding domain thereof of the fusion protein as described herein comprises a mutant of the cytokine of the TNF superfamily or a receptor binding domain thereof which binds and/or activates TRAIL-receptor 1 (TRAILR1) and/or TRAIL-receptor 2 (TRAILR2). The binding and/or activity of the mutant may be, e.g., determined by the assays as disclosed herein, e.g., in the Examples or by the assays disclosed in van der Sloot et al. (PNAS, 2006, 103:8634-8639), Kelley et al. (J. Biol. Chem., 2005, 280:2205-2215), or MacFarlane et al. (Cancer Res., 2005, 65: 11265-11270).

The mutant may be generated by any technique and is known by the skilled person, e.g., the techniques disclosed in an der Sloot et al. (PNAS, 2006, 103:8634-8639), Kelley et al. (J. Biol. Chem., 2005, 280:2205-2215), or MacFarlane et al. (Cancer Res., 2005, 65: 11265-11270) any may comprise any type of structural mutations, e.g., substitution, deletion, duplication and/or insertion of an amino acid. A preferred embodiment is the generation of substitutions. The substitution may affect at least one amino acid of the cytokine of the TNF superfamily or a receptor binding domain thereof as described herein. In a preferred embodiment, the substitution may affect at least one of the amino acids of TRAIL, e.g., human TRAIL (e.g., SEQ ID NO:10). Preferred substitutions in this regard affect at least one of the following amino acids of human TRAIL of SEQ ID NO:10: R130, G160, Y189, R191, Q193, E195, N199, K201, Y213, T214, S215, H264, 1266, D267, D269. Preferred amino acid substitutions of human TRAIL of SEQ ID NO:10 are at least one of the following substitutions: R130E, G160M, Y189A, Y189Q, R191K, Q193S, Q193R, E195R, N199V, N199R, K201R, Y213W, T214R, S215D, H264R, 1266L, D267Q, D269H, D269R, or D269K.

The amino acid substitution(s) may affect the binding and/or activity of TRAIL, e.g., human TRAIL, to or on either the TRAILR1 or the TRAILR2. Alternatively, the amino acid substitution(s) may affect the binding and/or activity of TRAIL, e.g., human TRAIL, to or on both, the TRAILR1 and the TRAILR2. The binding and/or activity of the TRAILR1 and/or TRAILR2 may be affected positively, i.e., stronger, more selective or specific binding and/or more activation of the receptor. Alternatively, the binding and/or activity of the TRAILR1 and/or TRAILR2 may be affected negatively, i.e., weaker, less selective or specific binding and/or less or no activation of the receptor.

Examples of mutants of TRAIL with amino acid substitution(s) that affect binding and/or activity of both TRAILR1 and TRAILR2 may be found, e.g., in Table 1 of MacFarlane et al. (cf. above) and may comprise human TRAIL mutants with the following two amino acid substitutions of SEQ ID NO:10 Y213W and S215D or the following single amino acid substitution Y189A.

Examples of mutants of TRAIL with amino acid substitution(s) that affect binding and/or activity of TRAILR1 may be found, e.g., in Table 1 of MacFarlane et al. (cf. above) and may comprise human TRAIL mutants with the following four amino acid substitutions of SEQ ID NO:10 N199V, K201R, Y213W and S215D or the following five amino acid substitutions Q193S, N199V, K201R, Y213W and S215D or in Table 2 of Kelley et al. (cf. above) and may comprise human TRAIL mutants with the following six amino acid substitutions Y213W, S215D, Y189A, Q193S, N199V, and K201R or Y213W, S215D, Y189A, Q193S, N199R, and K201R.

Examples of mutants of TRAIL with amino acid substitution(s) that affect binding and/or activity of TRAILR2 may be found, e.g., in Table 1 of MacFarlane et al. (cf. above) or in Table 2 of Kelley et al. (cf. above) and may comprise human TRAIL mutants with the following six amino acid substitutions of SEQ ID NO:14 Y189Q, R191K, Q193R, H264R, 1266L, and D267Q or in Table 2 of van der Sloot et al. (cf. above) and may comprise human TRAIL mutants with the following single amino acid substitution D269H, the following two amino acid substitutions D269H and E195R or D269H and T214R.

In a further preferred embodiment, the cytokine portion of the fusion protein is derived from human LIGHT (SEQ ID NO:16), particularly amino acids 91-240 of SEQ ID NO:16.

In a still further preferred embodiment, the cytokine portion of the fusion protein is derived from human APRIL (SEQ ID NO:13 or 14), particularly amino acids 112-247 or 113-247 of SEQ ID NO:13, or 112-250 or 113-250 of SEQ ID NO:14.

A flexible linker element may additionally located between the cytokine of the TNF superfamily or a receptor binding domain thereof (i) and the collectin trimerization domain as described herein (ii). The flexible linker element preferably has a length of 3-20 amino acids, particularly a length of 3, 6, 9, 10, 12, 15 or 18 amino acids. More preferably, the length of the linker is 9-15 amino acids. The linker element is preferably a glycine/serine linker, i.e., a peptide linker substantially consisting of the amino acids glycine and serine. In an especially preferred embodiment, the linker has the amino acid sequence $(GSS)_a(SSG)_b(GSG)_c$ wherein a, b, c is each 0, 1, 2, 3, 4, 5 or 6. It is clear to the skilled person that in cases in which the cytokine of the TNF superfamily or a receptor binding domain thereof already terminates with a G, e.g.

human TRAIL (SEQ ID NO:10) such a G may form the first G of the linker in the linker sequence $(GSS)_a(SSG)_b(GSG)_c$.

The collectin trimerization domain (ii) may comprise any collectin family member. Such members and their structures are summarized in, e.g., Hakansson et al. (Protein Science, 2000, 9:1607-1617) and may comprise surfactant protein-D, surfactant protein-A, mannan-binding protein-A, mannan-binding-protein-C, collectin liver 1, collectin placenta 1, or collectin-11. The collectin trimerization domain as described herein may be from a different species than the cytokine of the TNF superfamily or a receptor binding domain thereof as described herein. Alternatively, the collectin trimerization domain as described herein may be from the same species than the cytokine of the TNF superfamily or a receptor binding domain thereof described herein. In a preferred embodiment, the collectin domain as described herein is from human and the cytokine of the TNF superfamily or a receptor binding domain thereof as described herein is from human. In a preferred embodiment, the collectin trimerization domain comprises the neck and carbohydrate binding domain (CRD) domain of the surfactant protein-D, particularly amino acids 217-375, 218-375, 219-375, 220-375, 221-375, 222-375, 223-375, 224-375, 225-375 from human surfactant protein-D of SEQ ID NO:21. In another preferred embodiment, the collectin trimerization domain comprises the neck domain of the surfactant protein-D, particularly amino acids 217-257, 218-257, 219-257, 220-257, 221-257, 222-257, 223-257, 224-257, or 225-257 from human surfactant protein-D of SEQ ID NO:21. In another preferred embodiment, the collectin trimerization domain comprises the neck and carbohydrate binding domain (CRD) domain of collectin-11, particularly amino acids 110-271, 116-271, or 121-271 of human collectin-11 of SEQ ID NO:22. In another preferred embodiment, the collectin trimerization domain comprises the neck domain of collectin-11, particularly amino acids 110-147, 110-148, 110-149, 110-150, 110-151, 116-147, 116-148, 116-149, 116-150, 116-151, 121-147, 121-148, 121-149, 121-150, or 121-151 of human collectin-11 of SEQ ID NO:22.

The collectin trimerization domain (ii) may comprise a mutant, e.g., a mutant of surfactant protein-D or collectin-11, which does not bind to mannose. Such mutants may be identified by methods known to the skilled person, e.g., the methods disclosed in Crouch et al. (J Biol Chem, 2006, 281(26): 18008-18014). The collectin trimerization domain (ii) may further comprise a mutant which comprise at least one amino acid substitution as is described herein and may be generated as described herein. Such amino acid substitutions may modify the binding of the collectin trimerization domain to its ligand mannose and lead to an alteration of the clearance rate of a fusion protein as described herein when used in therapy and/or as pharmaceutical composition. The modification may result in a decreased or no binding to mannose and a low clearance rate. Such modifications may be achieved by, e.g., amino acid substitution that affect amino acid position F355 of human surfactant protein-D of SEQ ID NO:21, particularly by the amino acid substitutions F355A, F355S, F355T, F355E, F355D, F355K, or F355R. Especially preferred is the substitution F355D. Alternatively, the modification may result in an increased binding to mannose and a high clearance rate. Such modifications may be achieved by, e.g., amino acid substitution that affect amino acid position F355 of human surfactant protein-D of SEQ ID NO:21, particularly by the amino acid substitutions F355L, F355Y, or F355W.

In the fusion protein of the invention as described herein, the collectin trimerization domain (ii) may be located C-terminally of the cytokine of the TNF superfamily or a receptor binding domain thereof (i). Thus, the fusion protein may comprise a cytokine of the TNF superfamily or a receptor binding domain thereof as described herein and a collectin trimerization domain that comprises the neck domain alone or the neck and the CRD domain, e.g., the neck domain and the CRD and/or neck domain of surfactant protein-D or the neck domain and the CRD and/or neck domain of collectin-11 both as described herein wherein those domains are located C-terminally of the TNF superfamily or a receptor binding domain thereof (i). In this embodiment, it is preferred that the collectin trimerization domain comprises the neck domain and the CRD.

In the fusion protein of the invention as described herein, the collectin trimerization domain (ii) may be located N-terminally of the cytokine of the TNF superfamily or a receptor binding domain thereof (i). Thus, the fusion protein may comprise a cytokine of the TNF superfamily or a receptor binding domain thereof as described herein and a collectin trimerization domain that comprises the neck domain, e.g., the neck domain of surfactant protein-D or the neck domain of collectin-11 both as described herein wherein those domains are located N-terminally of the TNF superfamily or a receptor binding domain thereof (i).

In a preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the CRD and neck domain of surfactant protein-D, preferably amino acids 217-375, 218-375, 219-375, 220-375, 221-375, 222-375, 223-375, 224-375, 225-375 of human surfactant protein-D of SEQ ID NO:21 wherein the collectin trimerization domain is located C-terminally of TRAIL or mutant TRAIL as described herein. Preferred fusion proteins in this regard are SEQ ID Nos:26 or 27. Alternatively, the above fusion protein may additionally comprise a linker as described herein, e.g., a linker with the amino acid sequence $(GSS)_a(SSG)_b(GSG)_c$ wherein a, b, c is each 0, 1, 2, 3, 4, 5 or 6. Preferably, the linker has a length of 9-15 amino acids.

In a preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the neck domain of surfactant protein-D, preferably amino acids 217-257, 218-257, 219-257, 220-257, 221-257, 222-257, 223-257, 224-257, or 225-257 of human surfactant protein-D of SEQ ID NO:21 wherein the collectin trimerization domain is located C-terminally of TRAIL or mutant TRAIL as described herein. A preferred fusion protein in this regard is SEQ ID NO:28. Alternatively, the above fusion protein may additionally comprise a linker as described herein, e.g., a linker with the amino acid sequence $(GSS)_a(SSG)_b(GSG)_c$ wherein a, b, c is each 0, 1, 2, 3, 4, 5 or 6. Preferably, the linker has a length of 9-15 amino acids.

In another preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the CRD and neck domain of collectin-11, preferably amino acids 110-271, 116-271, or 121-271 of human collectin-11 of SEQ ID NO:22 wherein the collectin trimerization domain is located C-terminally of TRAIL or mutant TRAIL as described herein. Preferred fusion proteins in this regard are SEQ ID Nos:29 or 30. Alternatively, the above fusion protein may additionally comprise a linker as described herein, e.g., a linker with the amino acid sequence $(GSS)_a(SSG)_b(GSG)_c$ wherein a, b, c is each 0, 1, 2, 3, 4, 5 or 6.

Preferably, the linker has a length of 9-15 amino acids.

In another preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the neck domain of collectin-11, preferably amino acids 110-147, 110-148, 110-149, 110-150, 110-151, 116-147, 116-148, 116-149, 116-150, 116-151, 121-147, 121-148, 121-149, 121-150, or 121-151 of human collectin-11 of SEQ ID NO:22 wherein the collectin trimerization domain is located C-terminally of TRAIL or mutant TRAIL as described herein. A preferred fusion protein in this regard is SEQ ID NO:31. Alternatively, the above fusion protein may additionally comprise a linker as described herein, e.g., a linker with the amino acid sequence $(GSS)_a(SSG)_b(GSG)_c$ wherein a, b, c is each 0, 1, 2, 3, 4, 5 or 6. Preferably, the linker has a length of 9-15 amino acids. Preferred fusion proteins in this regard are SEQ ID Nos:36 or 37.

In a preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the neck domain of surfactant protein-D, preferably amino acids 217-257, 218-257, 219-257, 220-257, 221-257, 222-257, 223-257, 224-257, or 225-257 of human surfactant protein-D of SEQ ID NO:21 wherein the collectin trimerization domain is located N-terminally of TRAIL or mutant TRAIL as described herein. Alternatively, the above fusion protein may additionally comprise a linker as described herein, e.g., a linker with the amino acid sequence $(GSS)_a(SSG)_b(GSG)_c$ wherein a, b, c is each 0, 1, 2, 3, 4, 5 or 6. Preferably, the linker has a length of 9-15 amino acids.

In another preferred embodiment, the fusion protein comprises TRAIL, particularly human TRAIL or a receptor binding domain thereof or a mutant of TRAIL as described herein, preferably 95-281, 116-281, 117-281, 118-281, 119-281 or 120-281 of human TRAIL (SEQ ID NO:10) and a collectin trimerization domain or mutant thereof as described herein, particularly the neck domain of collectin-11, preferably amino acids 110-147, 110-148, 110-149, 110-150, 110-151, 116-147, 116-148, 116-149, 116-150, 116-151, 121-147, 121-148, 121-149, 121-150, or 121-151 of human collectin-11 of SEQ ID NO:22 wherein the collectin trimerization domain is located N-terminally of TRAIL or mutant TRAIL as described herein. Preferred fusion proteins in this regard are SEQ ID Nos:32-34. Alternatively, the above fusion protein may additionally comprise a linker as described herein, e.g., a linker with the amino acid sequence $(GSS)_a(SSG)_b(GSG)_c$ wherein a, b, c is each 0, 1, 2, 3, 4, 5 or 6. Preferably, the linker has a length of 9-15 amino acids. Preferred fusion proteins in this regard is SEQ ID NO: 35.

In another preferred embodiment, the fusion protein comprises CD95L, particularly human CD95L, or a receptor binding domain thereof as described herein, e.g. amino acids 21-160 of SEQ ID NO:40, and a collectin trimerization domain comprising the neck domain and optionally the CRD of human SP-D, e.g. amino acids 172-209 and 210-327 of SEQ ID NO:40, respectively, or a mutant thereof as described herein. Preferably, the fusion protein may comprise a linker, e.g. a flexible linker, more preferably a glycine/serine linker as described herein having a length of preferably 9-15 amino acids. A preferred fusion protein in this regard comprises SEQ ID NO:40, particularly amino acids 21-327 of SEQ ID NO:40.

In another preferred embodiment, the fusion protein comprises LIGHT, particularly human LIGHT or a receptor binding domain thereof as described herein, preferably amino acids 21-170 of SEQ ID NO:41, and a collectin trimerization domain comprising the neck domain and optionally the CRD of human SP-D, e.g. amino acids 182-219, and 220-337 of SEQ ID NO:41, respectively, or a mutant thereof as described herein. Preferably, the cytokine and the collectin domain are connected by a linker, e.g. a glycine/serine linker as described herein, having a length of preferably 9-15 amino acids. A preferred fusion protein in this regard comprises SEQ ID NO:41, particularly amino acids 21-327 of SEQ ID NO:41.

In another preferred embodiment, the fusion protein comprises TRAIL, particularly human TRAIL or a receptor binding domain thereof or mutant of TRAIL as described herein, e.g. amino acids 21-181 of SEQ ID NO:43 (wild type TRAIL), amino acids 21-181 of SEQ ID NO:47 (TRAILR1mut) or amino acids 21-181 of SEQ ID NO:48 (TRAILR2mut). Further, the fusion protein comprises a collectin trimerization domain selected from the neck domain and optionally the CRD of human SP-D, e.g. amino acids 193-230, and 231-384 of SEQ ID NO:43, respectively, or a mutant thereof as described herein, e.g. mutants as shown in SEQ ID NO:49 or 50. Preferably, the fusion polypeptide comprises both the neck region and the CRD of human SP-D. The cytokine and collectin domain are preferably connected by a linker, e.g. a glycine/serine linker as described herein. Preferably, the linker has a length of 9-15 amino acids. Preferred fusion proteins in this regard comprise (i) SEQ ID NO:43, particularly amino acids 21-348 of SEQ ID NO:43, (ii) SEQ ID NO:44, particularly amino acids 21-230 of SEQ ID NO:44, (iii) SEQ ID NO:47, particularly amino acids 21-348 of SEQ ID NO:47, (iv) SEQ ID NO:48, particularly amino acids 21-348 of SEQ ID NO:48, (v) SEQ ID NO: 49, particularly amino acids 21-348 of SEQ ID NO:49 or (vi) SEQ ID NO:50, particularly amino acids 21-348 of SEQ ID NO:50.

In another preferred embodiment, the fusion protein comprises TRAIL, particularly human TRAIL or receptor-binding domain thereof or a mutant of TRAIL as described herein above, and a collectin trimerization domain, which is the neck domain of human collectin 11, and optionally the CRD of human collectin 11, e.g. amino acids 193-224 and 225-347 of SEQ ID NO:45, respectively. Preferably, the CRD is present. Preferably, the cytokine and the collectin domain are connected by a linker, e.g. a glycine/serine linker as described above herein, preferably having a length of 9-15 amino acids. Preferred fusion proteins in this regard comprise SEQ ID NO:45 and SEQ ID NO:46, particularly, amino acids 21-347 of SEQ ID NO:45 or amino acids 21-229 of SEQ ID NO:46.

In another preferred embodiment, the fusion protein comprises APRIL, particularly human APRIL or a receptor binding domain thereof as described herein, e.g. amino acids 21-158 of SEQ ID NO:51 and a collectin trimerization domain as described herein, particularly the neck domain and optionally the CRD of human SP-D or a mutant thereof, as described herein, e.g. amino acids 170-207 and 208-325 of SEQ ID NO:51, respectively. The cytokine and the collectin domain are preferably connected by a linker, e.g. a glycine/ serine linker as described herein, preferably having a length of 9-15 amino acids. The preferred fusion protein in this regard comprises SEQ ID NO:51, particularly amino acids 21-325 of SEQ ID NO:51.

The fusion protein as described herein may additionally comprise an N-terminal signal peptide domain, which allows processing, e.g., extracellular secretion, in a suitable host cell. Preferably, the N-terminal signal peptide domain comprises a protease, e.g., a signal peptidase cleavage site and thus may be removed after or during expression to obtain the mature protein. In a preferred embodiment, the N-terminal signal peptide domain comprises the sequence SEQ ID NO:23, SEQ ID NO:24, or SEQ ID NO:25.

Further, the fusion protein may comprise comprises a recognition/purification domain, e.g., a Strep-tag domain and/or a poly-His domain, which may be located at the N-terminus or at the C-terminus.

The fusion protein may additionally comprise a C-terminal flexible element, having a length of, e.g., 1-50, preferably 10-30 amino acids which may include and/or connect to a recognition/purification domain as described herein.

A further aspect of the present invention relates to a nucleic acid molecule encoding a fusion protein as described herein. The nucleic acid molecule may be a DNA molecule, e.g., a double-stranded or single-stranded DNA molecule, or an RNA molecule. The nucleic acid molecule may encode the fusion protein or a precursor thereof, e.g., a pro- or pre-proform of the fusion protein which may comprise a signal sequence as described herein or other heterologous amino acid portions for secretion or purification which are preferably located at the N- and/or C-terminus of the fusion protein as described herein. The nucleic acid molecule may encode the fusion protein wherein the heterologous amino acid portions may be linked to the first and/or second domain via a protease cleavage site, e.g., a Factor $X_a$, thrombin or IgA protease cleavage site.

Examples of nucleic acids that comprise the coding sequence of a fusion protein as described herein are SEQ ID Nos:38, 39 or 42.

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosal integration vector, etc. Examples of suitable expression control sequences and vectors are described for example by Sambrook et al. (1989) *Molecular Cloning, A Laboratory Manual*, Cold Spring Harbor Press, and Ausubel et al. (1989), *Current Protocols in Molecular Biology*, John Wiley & Sons or more recent editions thereof.

Various expression vector/host cell systems may be used to express the nucleic acid sequences encoding the fusion proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells. The nucleic acid molecule encoding the fusion protein as described herein may be optimized in view of its codon-usage for the expression in suitable host cells, e.g. *E. coli*, yeast cells, plant cells, insect cells, animal cells, e.g., mammalian cells or human cells.

Further, the invention relates to a non-human organism, e.g., mouse or rat, transformed or transfected with a nucleic acid molecule as described herein. Such organisms may be comprise knock-out organisms, generated by known methods of genetic transfer including homologous recombination. Alternatively, such organisms may comprise transgenic organisms which comprise several copies of the nucleic acid molecule as described herein. The generation of transgenic organisms is known in the art.

The fusion protein, the nucleic acid coding therefore, the transformed or transfected cell as well as the trimeric complexes or oligomers of the trimeric complexes, all as described herein may be used for pharmaceutical, diagnostic and/or research applications. For these applications it is preferred to use fusion proteins in which both the TNF-superfamily cytokine or receptor binding domain thereof as described herein and the collectin trimerization domain as described herein are from the same species in order to minimize immunological effects, e.g., from human when applying such proteins to humans. In addition, the fusion of a TNF-superfamily cytokine or receptor binding domain thereof as described herein to a neck-collectin trimerization domain as described herein, e.g., neck domain from surfactant protein-D or collectin-11, may lead to fast clearance. Alternatively, the fusion of a TNF-superfamily cytokine or receptor binding domain thereof as described herein to a neck and CRD-collectin trimerization domain as described herein, e.g., neck and CRD domain from surfactant protein-D or collectin-11, may lead to low clearance. The use of mutants of the collectin trimerization domain as described herein may modify the clearance rate of the fusion protein in a way as described herein.

A further aspect of the present invention relates to a pharmaceutical or diagnostic composition comprising as an active agent at least one fusion protein, the nucleic acid coding therefore, the transformed or transfected cell as well as the trimeric complexes or oligomers of the trimeric complexes, all as described herein.

At least one fusion protein, the nucleic acid coding therefor, the transformed or transfected cell as well as the trimeric complexes or oligomers of the trimeric complexes, all as described herein may be used in therapy, e.g., in the prophylaxis and/or treatment of disorders selected from proliferative disorders, particularly disorders caused by, associated with and/or accompanied by dysfunction of TNF cytokines, such as tumors, e.g. solid or lymphatic tumors, infectious diseases, inflammatory diseases, metabolic diseases, autoimmune disorders, e.g. rheumatoid and/or arthritic diseases, degenerative diseases, e.g. neurodegenerative diseases such as multiple sclerosis, apoptosis-associated diseases and transplant rejections.

The composition may be administered as monotherapy or as combination therapy with further medicaments, e.g. cytostatic or chemotherapeutic agents, corticosteroids and/or antibiotics. Preferably, the composition is administered together with tumor-selective apoptosis sensitizing and/or inducing agents, e.g. as described in Example 2.8.

The fusion protein is administered to a subject in need thereof, particularly a human patient, in a sufficient dose for the treatment of the specific conditions by suitable means. For example, the fusion protein may be formulated as a pharmaceutical composition together with pharmaceutically acceptable carriers, diluents and/or adjuvants. Therapeutic efficacy and toxicity may be determined according to standard protocols. The pharmaceutical composition may be administered systemically, e.g. intraperitoneally, intramuscularly or intravenously or locally, e.g. intranasally, subcutaneously or intrathecally. Preferred is intravenous administration.

The dose of the fusion protein administered will of course be dependent on the subject to be treated, on the subject's weight, the type and severity of the disease, the manner of administration and the judgement of the prescribing physician. For the administration of fusion proteins, a daily dose of 0.001 to 100 mg/kg is suitable. Table 1 shows a list of cytokines of the TNF super family which may be used in the present invention.

TABLE 1

| Approved Gene symbol | TNFSF-number | Synonyms | Accession | NH2-aa | COOH-aa | Length |
|---|---|---|---|---|---|---|
| LTA | TNFSF-1 | LTA | gi\|6806893\|ref\|NP_000586.2\| | Ser59 | Leu205 | 147aa |
|  |  |  |  | Thr60 | Leu205 | 146aa |
| TNF | TNFSF-2 | TNF-alpha | gi\|25952111\|ref\|NP_000585.2\| | Asp86 | Leu233 | 148aa |
| LTB | TNFSF-3 | LTB | gi\|4505035\|ref\|NP_002332.1\| | Asp82 | Gly244 | 163aa |
|  |  |  |  | Gly86 | Gly244 | 159aa |
| TNFSF4 | TNFSF-4 | OX40L/GP34 | gi\|4507603\|ref\|NP_003317.1\| | Val52 | Leu183 | 132aa |
|  |  |  |  | Arg55 | Leu183 | 129aa |
| CD40LG | TNFSF-5 | CD40L | gi\|4557433\|ref\|NP_000065.1\| | Asp117 | Leu261 | 150aa |
|  |  |  |  | Glu112 | Leu261 | 145aa |
| FASLG | TNFSF-6 | CD95L/APO-L/7FAS-L | gi\|4557329\|ref\|NP_000630.1\| | Glu142 | Leu281 | 140aa |
|  |  |  |  | Arg144 | Leu281 | 138aa |
| TNFSF7 | TNFSF-7 | CD27L | gi\|4507605\|ref\|NP_001243.1\| | Glu51 | Pro193 | 143aa |
|  |  |  |  | Asp56 | Pro193 | 138aa |
| TNFSF8 | TNFSF-8 | CD30L | gi\|4507607\|ref\|NP_001235.1\| | Lys97 | Asp234 | 138aa |
|  |  |  |  | Ser98 | Asp234 | 137aa |
|  |  |  |  | Leu102 | Asp234 | 133aa |
| TNFSF9 | TNFSF-9 | 4-1BB/CD137L | gi\|4507609\|ref\|NP_003802.1\| | Asp86 | Glu254 | 169aa |
| TNFSF10 | TNFSF-10 | TRAIL | gi\|4507593\|ref\|NP_003801.1\| | Glu116 | Gly281 | 166aa |
|  |  |  |  | Gly118 | Gly281 | 164aa |
| TNFSF11 | TNFSF-11 | TRANCE/RANKL | gi\|4507595\|ref\|NP_003692.1\| | Glu161 | Asp317 | 157aa |
| TNFSF12 | TNFSF-12 | TWEAK/Apo-3 | gi\|4507597\|ref\|NP_003800.1\| | Ala103 | His249 | 147aa |
|  |  |  |  | Arg104 | His249 | 146aa |
|  |  |  |  | Arg105 | His249 | 145aa |
| TNFSF13 | TNFSF-13 | APRIL/TALL-2/TRDL-1 | gi\|26051248\|ref\|NP_742085.1\| | Lys112 | Leu247 | 136aa |
| TNFSF13 | TNFSF-13 | APRIL/TALL-2/TRDL-1 | gi\|4507599\|ref\|NP_003799.1\| | Lys112 | Leu250 | 139aa |
| TNFSF13B | TNFSF-13B | BAFF/Blys | gi\|5730097\|ref\|NP_006564.1\| | Glu140 | Leu285 | 146aa |
| TNFSF14 | TNFSF-14 | LIGHT | gi\|25952144\|ref\|NP_003798.2\| | Glu91 | Val240 | 150aa |
| TNFSF15 | TNFSF-15 | TL1A/VEGI | gi\|23510445\|ref\|NP_005109.2\| | Asp91 | Leu251 | 161aa |
|  |  |  |  | Asp93 | Leu251 | 159aa |
| TNFSF18 | TNFSF-18 | GITRL | gi\|4827034\|ref\|NP_005083.1\| | Glu52 | Ser177 | 126aa |
| EDA |  | EDA-A1 | gi\|4503449\|ref\|NP_001390.1\| | Glu245 | Ser391 | 147aa |
| EDA |  | EDA-A2 | gi\|54112101\|ref\|NP_001005609.1\| | Glu245 | Ser389 | 145aa |

In a different aspect, the present invention refers to novel amino acid substitution variants of human surfactant protein-D (SP-D) comprising a carbohydrate recognition domain with reduced carbohydrate binding capacity, optionally fused to at least one heterologous polypeptide or polypeptide domain as well as nucleic acid molecules encoding such fusion polypeptides. Preferably, the mutated SP-D polypeptides of the present invention have an amino acid substitutions at position F355 of human surfactant protein-D of SEQ ID NO:21, particularly an amino acid substitution by hydrophilic or charged amino acid, e.g. F355S, F355T, F355E, F355D, F355H or F355R, particularly F355D. The heterologous polypeptide or polypeptide domain is preferably of mammalian, e.g. human origin, e.g. a TNSF cytokine domain as described above. The mutated SP-D polypeptides preferably comprise an SP-D neck domain as described above. The heterologous polypeptide may be fused to N- and/or C-terminus of the SP-D domain. Preferably, a linker, e.g. a linker as described herein above, is present between the SP-D and heterologous polypeptide domain.

Basic Structure of a Fusion Protein

In the following, the basic structure of the recombinant proteins of the invention is shown exemplified for the TNF-superfamily cytokines as described herein.

1.1 Sequences of the Signal Peptides

```
                                              (SEQ ID NO: 23)
                    MNFGFSLIFLVLVLKGVQC (SEQ ID NO: 24)
                    METDTLLLWVLLLWVPGSTG (SEQ ID NO: 25)
                    METDTLLLWVLLLWVPAGNG
```

1.2 Flag-Epitope/Enterokinase-Processing Site

```
                         DYKDDDDKD
```

1.3 Human Collectins

```
Surfactant Protein-D
                                              (SEQ ID NO: 21)
  1 MLLFLLSALV LLTQPLGYLE AEMKTYSHRT TPSACTLVMC SSVESGLPGR DGRDGREGPR

61 GEKGDPGLPG AAGQAGMPGQ AGPVGPKGDN GSVGEPGPKG DTGPSGPPGP PGVPGPAGRE

121 GPLGKQGNIG PQGKPGPKGE AGPKGEVGAP GMQGSAGARG LAGPKGERGV PGERGVPGNA

181 GAAGSAGAMG PQGSPGARGP PGLKGDKGIP GDKGAKGESG LPDVASLRQQ VEALQGQVQH

241 LQAAFSQYKK VELFPNGQSV GEKIFKTAGF VKPFTEAQLL CTQAGGQLAS PRSAAENAAL
```

```
301 QQLVVAKNEA AFLSMTDSKT EGKFTYPTGE SLVYSNWAPG EPNDDGGSED CVEIFTNGKW

361 NDRACGEKRL VVCEF

Collectin-11
                                                       (SEQ ID NO: 22)
  1 MRGNLALVGV LISLAFLSLL PSGHPQPAGD DACSVQILVP GLKGDAGEKG DKGAPGRPGR

61 VGPTGEKGDM GDKGQKGSVG RHGKIGPIGS KGEKGDSGDI GPPGPNGEPG LPCECSQLRK

121 AIGEMDNQVS QLTSELKFIK NAVAGVRETE SKIYLLVKEE KRYADAQLSC QGRGGTLSMP

181 KDEAANGLMA AYLAQAGLAR VFIGINDLEK EGAFVYSDHS PMRTFNKWRS GEPNNAYDEE

241 DCVEMVASGG WNDVACHTTM YFMCEFDKEN M
```

Various fragments of the human collectins Surfactant protein-D and collectin-11 are conceivable as trimerization domains as described herein.

1.4 Flexible Linker Element $(GSS)_a(SSG)_b(GSG)_c$ wherein a, b, c is each 0, 1, 2, 3, 4, 5 or 6

1.5 TNF-Superfamily Cytokine/Receptor Binding Domain Thereof (See Also Table 1)

```
SEQ NP_000586_TNFSF1_LTA
KEYWORD PROTEIN
FEATURES
ORIGIN
                                                            SEQ-ID-01
  1    MTPPERLFLP RVCGTTLHLL LLGLLLVLLP GAQGLPGVGL TPSAAQTARQ HPKMHLAHST

61    LKPAAHLIGD PSKQNSLLWR ANTDRAFLQD GFSLSNNSLL VPTSGIYFVY SQVVFSGKAY

121    SPKATSSPLY LAHEVQLFSS QYPFHVPLLS SQKMVYPGLQ EPWLHSMYHG AAFQLTQGDQ

181    LSTHTDGIPH LVLSPSTVFF GAFAL

SEQ NP_000585_TNESF2_TNFa
KEYWORD PROTEIN
ORIGIN
                                                            SEQ-ID-02
  1    MSTESMIRDV ELAEEALPKK TGGPQGSRRC LFLSLFSFLI VAGATTLFCL LHFGVIGPQR

61    EEFPRDLSLI SPLAQAVRSS SRTPSDKPVA HVVANPQAEG QLQWLNRRAN ALLANGVELR

121    DNQLVVPSEG LYLIYSQVLF KGQGCPSTHV LLTHTISRIA VSYQTKVNLL SAIKSPCQRE

181    TPEGAEAKPW YEPIYLGGVF QLEKGDRLSA EINRPDYLDF AESGQVYFGI IAL

SEQ NP_002332_TNFSF3_LTB
KEYWORD PROTEIN
ORIGIN
                                                            SEQ-ID-03
  1    MGALGLEGRG GRLQGRGSLL LAVAGATSLV TLLLAVPITV LAVLALVPQD QGGLVTETAD

61    PGAQAQQGLG FQKLPEEEPE TDLSPGLPAA HLIGAPLKGQ GLGWETTKEQ AFLTSGTQFS

121    DAEGLALPQD GLYYLYCLVG YRGRAPPGGG DPQGRSVTLR SSLYRAGGAY GPGTPELLLE

181    GAETVTPVLD PARRQGYGPL WYTSVGFGGL VQLRRGERVY VNISHPDMVD FARGKTFFGA

241    VMVG

SEQ NP_003317_TNESF4_OX40L
KEYWORD PROTEIN
ORIGIN
                                                            SEQ-ID-04
  1    MERVQPLEEN VGNAARPRFE RNKLLLVASV IQGLGLLLCF TYICLHFSAL QVSHRYPRIQ

61    SIKVQFTEYK KEKGFILTSQ KEDEIMKVQN NSVIINCDGF YLISLKGYFS QEVNISLHYQ

121    KDEEPLFQLK KVRSVNSLMV ASLTYKDKVY LNVTTDNTSL DDFHVNGGEL ILIHQNPGEF

181    CVL

SEQ NP_000065_TNESF5_CD40L
KEYWORD PROTEIN
ORIGIN
                                                            SEQ-ID-05
  1    MIETYNQTSP RSAATGLPIS MKIFMYLLTV FLITQMIGSA LFAVYLHRRL DKIEDERNLH
```

-continued

```
  61    EDFVFMKTIQ RCNTGERSLS LLNCEEIKSQ FEGFVKDIML NKEETKKENS FEMQKGDQNP

121    QIAAHVISEA SSKTTSVLQW AEKGYYTMSN NLVTLENGKQ LTVKRQGLYY IYAQVTFCSN

181    REASSQAPFI ASLCLKSPGR FERILLRAAN THSSAKPCGQ QSIHLGGVFE LQPGASVFVN

241    VTDPSQVSHG TGFTSFGLLK L
```

SEQ NP_000630_TNFSF6_CD95L
KEYWORD PROTEIN
ORIGIN
SEQ-ID-06
```
   1    MQQPFNYPYP QIYWVDSSAS SPWAPPGTVL PCPTSVPRRP GQRRPPPPPP PPPLPPPPPP

61    PPLPPLPLPP LKKRGNHSTG LCLLVMFFMV LVALVGLGLG MFQLFHLQKE LAELRESTSQ

121    MHTASSLEKQ IGHPSPPPEK KELRKVAHLT GKSNSRSMPL EWEDTYGIVL LSGVKYKKGG

181    LVINETGLYF VYSKVYFRGQ SCNNLPLSHK VYMRNSKYPQ DLVMMEGKMM SYCTTGQMWA

241    RSSYLGAVFN LTSADHLYVN VSELSLVNFE ESQTFFGLYK L
```

SEQ NP_001243_TNFSF7_CD27L
KEYWORD PROTEIN
ORIGIN
SEQ-ID-07
```
   1    MPEEGSGCSV RRRPYGCVLR AALVPLVAGL VICLVVCIQR FAQAQQQLPL ESLGWDVAEL

61    QLNHTGPQQD PRLYWQGGPA LGRSFLHGPE LDKGQLRIHR DGIYMVHIQV TLAICSSTTA

121    SRHHPTTLAV GICSPASRSI SLLRLSFHQG CTIASQRLTP LARGDTLCTN LTGTLLPSRN

181    TDETFFGVQW VRP
```

SEQ NP_001235_TNESF8_CD3OL
KEYWORD PROTEIN
ORIGIN
SEQ-ID-08
```
   1    MDPGLQQALN GMAPPGDTAM HVPAGSVASH LGTTSRSYFY LTTATLALCL VFTVATIMVL

61    VVQRTDSIPN SPDNVPLKGG NCSEDLLCIL KRAPFKKSWA YLQVAKHLNK TKLSWNKDGI

121    LHGVRYQDGN LVIQFPGLYF IICQLQFLVQ CPNNSVDLKL ELLINKHIKK QALVTCESG

181    MQTKHVYQNL SQFLLDYLQV NTTISVNVDT FQYIDTSTFP LENVLSIFLY SNSD
```

SEQ NP_003802_TNFSF9_CD137L
KEYWORD PROTEIN
ORIGIN
SEQ-ID-09
```
   1    MEYASDASLD PEAPWPPAPR ARACRVLPWA LVAGLLLLLL LAAACAVFLA CPWAVSGARA

61    SPGSAASPRL REGPELSPDD PAGLLDLRQG MFAQLVAQNV LLIDGPLSWY SDPGLAGVSL

121    TGGLSYKEDT KELVVAKAGV YYVFFQLELR RVVAGEGSGS VSLALHLQPL RSAAGAAALA

181    LTVDLPPASS EARNSAFGFQ GRLLHLSAGQ RLGVHLHTEA RARHAWQLTQ GATVLGLFRV

241    TPEIPAGLPS PRSE
```

SEQ NP_003801_TNESF10_TRAIL
KEYWORD PROTEIN
ORIGIN
SEQ-ID-10
```
   1    MAMMEVQGGP SLGQTCVLIV IFTVLLQSLC VAVTYVYFTN ELKQMQDKYS KSGIACFLKE

61    DDSYWDPNDE ESMNSPCWQV KWQLRQLVRK MILRTSEETI STVQEKQQNI SPLVRERGPQ

121    RVAAHITGTR GRSNTLSSPN SKNEKALGRK INSWESSRSG HSFLSNLHLR NGELVIHEKG

181    FYYIYSQTYF RFQEEIKENT KNDKQMVQYI YKYTSYPDPI LLMKSARNSC WSKDAEYGLY

241    SIYQGGIFEL KENDRIFVSV TNEHLIDMDH EASFFGAFLV G
```

SEQ NP_003692_TNESF11_a_RANKL
KEYWORD PROTEIN
ORIGIN
SEQ-ID-11
```
   1    MRRASRDYTK YLRGSEEMGG GPGAPHEGPL HAPPPPAPHQ PPAASRSMFV ALLGLGLGQV

61    VCSVALFFYF RAQMDPNRIS EDGTHCIYRI LRLHENADFQ DTTLESQDTK LIPDSCRRIK
```

```
    121   QAFQGAVQKE LQHIVGSQHI RAEKAMVDGS WLDLAKRSKL EAQPFAHLTI NATDIPSGSH

181   KVSLSSWYHD RGWAKISNMT FSNGKLIVNQ DGFYYLYANI CFRHHETSGD LATEYLQLMV

241   YVTKTSIKIP SSHTLMKGGS TKYWSGNSEF HFYSINVGGF KLRSGEEIS IEVSNPSLLD

301   PDQDATYFGA FKVRDID

SEQ NP_003800_TNFSF12_TWEAK
KEYWORD PROTEIN
ORIGIN
                                                                    SEQ-ID-12
      1   MAARRSQRRR GRRGEPGTAL LVPLALGLGL ALACLGLLLA VVSLGSRASL SAQEPAQEEL

61   VAEEDQDPSE LNPQTEESQD PAPFLNRLVR PRRSAPKGRK TRARRAIAAH YEVHPRPGQD

121   GAQAGVDGTV SGWEEARINS SSPLRYNRQI GEFIVTRAGL YYLYCQVHFD EGKAVYLKLD

181   LLVDGVLALR CLEEFSATAA SSLGPQLRLC QVSGLLALRP GSSLRIRTLP WAHLKAAPFL

241   TYFGLFQVH

SEQ NP_742085_TNESF13_APRIL_ver1
KEYWORD PROTEIN
ORIGIN
                                                                    SEQ-ID-13
      1   MPASSPFLLA PKGPPGNMGG PVREPALSVA LWLSWGAALG AVACAMALLT QQTELQSLRR

61   EVSRLQGTGG PSQNGEGYPW QSLPEQSSDA LEAWENGERS RKRRAVLTQK QKKQHSVLHL

121   VPINATSKDD SDVTEVMWQP ALRRGRGLQA QGYGVRIQDA GVYLLYSQVL FQDVTFTMGQ

181   VVSREGQGRQ ETLFRCIRSM PSHPDRAYNS CYSAGVFHLH QGDILSVIIP RARAKLNLSP

241   HGTFLGL

SEQ NP_003799_TNESF13_APRIL_ver2
KEYWORD PROTEIN
ORIGIN
                                                                    SEQ-ID-14
      1   MPASSPFLLA PKGPPGNMGG PVREPALSVA LWLSWGAALG AVACAMALLT QQTELQSLRR

61   EVSRLQGTGG PSQNGEGYPW QSLPEQSSDA LEAWENGERS RKRRAVLTQK QKKQHSVLHL

121   VPINATSKDD SDVTEVMWQP ALRRGRGLQA QGYGVRIQDA GVYLLYSQVL FQDVTFTMGQ

181   VVSREGQGRQ ETLFRCIRSM PSHPDRAYNS CYSAGVFHLH QGDILSVIIP RARAKLNLSP

241   HGTFLGFVKL

SEQ NP_006564_TNFSF13b_BAFF
KEYWORD PROTEIN
ORIGIN
                                                                    SEQ-ID-15
      1   MDDSTEREQS RLTSCLKKRE EMKLKECVSI LPRKESPSVR SSKDGKLLAA TLLLALLSCC

61   LTVVSFYQVA ALQGDLASLR AELQGHHAEK LPAGAGAPKA GLEEAPAVTA GLKIFEPPAP

121   GEGNSSQNSR NKRAVQGPEE TVTQDCLQLI ADSETPTIQK GSYTFVPWLL SFKRGSALEE

181   KENKILVKET GYFFIYGQVL YTDKTYAMGH LIQRKKVHVF GDELSLVTLF RCIQNMPETL

241   PNNSCYSAGI AKLEEGDELQ LAIPRENAQI SLDGDVTFFG ALKLL

SEQ NP_003798_TNFSF14_LIGHT
KEYWORD PROTEIN
ORIGIN
                                                                    SEQ-ID-16
      1   MEESVVRPSV FVVDGQTDIP FTRLGRSHRR QSCSVARVGL GLLLLLMGAG LAVQGWFLLQ

61   LHWRLGEMVT RLPDGPAGSW EQLIQERRSH EVNPAAHLTG ANSSLTGSGG PLLWETQLGL

121   AFLRGLSYHD GALVVTKAGY YYIYSKVQLG GVGCPLGLAS TITHGLYKRT PRYPEELELL

181   VSQQSPCGRA TSSRVWWDS SFLGGVVHLE AGEKVVVRVL DERLVRLRDG TRSYFGAFMV

SEQ NP_005109_TNFSF15_TL1A
KEYWORD PROTEIN
ORIGIN
                                                                    SEQ-ID-17
```

```
      1   MAEDLGLSFG ETASVEMLPE HGSCRPKARS SSARWALTCC LVLLPFLAGL TTYLLVSQLR

61   AQGEACVQFQ ALKGQEFAPS HQQVYAPLRA DGDKPRAHLT VVRQTPTQHF KNQFPALHWE

121   HELGLAFTKN RMNYTNKFLL IPESGDYFIY SQVTFRGMTS ECSEIRQAGR PNKPDSITVV

181   ITKVTDSYPE PTQLLMGTKS VCEVGSNWFQ PIYLGAMFSL QEGDKLMVNV SDISLVDYTK

241   EDKTFFGAFL L

SEQ P_005083_TNFSF18_GITRL
KEYWORD PROTEIN
ORIGIN
                                                                SEQ-ID-18
      1   MCLSHLENMP LSHSRTQGAQ RSSWKLWLFC SIVMLLFLCS FSWLIFIFLQ LETAKEPCMA

61   KFGPLPSKWQ MASSEPPCVN KVSDWKLEIL QNGLYLIYGQ VAPNANYNDV APFEVRLYKN

121   KDMIQTLTNK SKIQNVGGTY ELHVGDTIDL IFNSEHQVLK NNTYWGIILL ANPQFIS

SEQ NP_001390_EDA-A1
KEYWORD PROTEIN
ORIGIN
                                                                SEQ-ID-19
      1   MGYPEVERRE LLPAAAPRER GSQGCGCGGA PARAGEGNSC LLFLGFFGLS LALHLLTLCC

61   YLELRSELRR ERGAESRLGG SGTPGTSGTL SSLGGLDPDS PITSHLGQPS PKQQPLEPGE

121   AALHSDSQDG HQMALLNFFF PDEKPYSEEE SRRVRRNKRS KSNEGADGPV KNKKKGKKAG

181   PPGPNGPPGP PGPPGPQGPP GIPGIPGIPG TTVMGPPGPP GPPGPQGPPG LQGPSGAADK

241   AGTRENQPAV VHLQGQGSAI QVKNDLSGGV LNDWSRITMN PKVFKLHPRS GELEVLVDGT

301   YFIYSQVEVY YINFTDFASY EVVVDEKPFL QCTRSIETGK TNYNTCYTAG VCLLKARQKI

361   AVKMVHADIS INMSKHTTFF GAIRLGEAPA S

SEQ NP_001005609_EDA-A2
KEYWORD PROTEIN
ORIGIN
                                                                SEQ-ID-20
      1   MGYPEVERRE LLPAAAPRER GSQGCGCGGA PARAGEGNSC LLFLGFFGLS LALHLLTLCC

61   YLELRSELRR ERGAESRLGG SGTPGTSGTL SSLGGLDPDS PITSHLGQPS PKQQPLEPGE

121   AALHSDSQDG HQMALLNFFF PDEKPYSEEE SRRVRRNKRS KSNEGADGPV KNKKKGKKAG

181   PPGPNGPPGP PGPPGPQGPP GIPGIPGIPG TTVMGPPGPP GPPGPQGPPG LQGPSGAADK

241   AGTRENQPAV VHLQGQGSAI QVKNDLSGGV LNDWSRITMN PKVFKLHPRS GELEVLVDGT

301   YFIYSQVYYI NFTDFASYEV VVDEKPFLQC TRSIETGKTN YNTCYTAGVC LLKARQKIAV

361   KMVHADISIN MSKHTTFFGA IRLGEAPAS
```

Various fragments, e.g., receptor binding domains, of TNF-superfamily cytokines are conceivable as described herein.

1.6 Examples of Fusion Proteins

```
SP-hsTrailsyn-SPD-Konstrukt-1_PRO.PRO
KEYWORD PROTEIN
ORIGIN
                                                              SEQ ID NO: 26
      1   METDTLLLWV LLLWVPAGNG QRVAAHITGT RGRSNTLSSP NSKNEKALGR KINSWESSRS

61   GHSFLSNLHL RNGELVIHEK GFYYIYSQTY FRFQEEIKEN TKNDKQMVQY IYKYTSYPDP

121   ILLMKSARNS CWSKDAEYGL YSIYQGGIFE LKENDRIFVS VTNEHLIDMD HEASFFGAFL

181   VGSGLPDVAS LRQQVEALQG QVQHLQAAFS QYKKVELFPN GQSVGEKIFK TAGFVKPFTE

241   AQLLCTQAGG QLASPRSAAE NAALQQLVVA KNEAAFLSMT DSKTEGKFTY PTGESLVYSN

301   WAPGEPNDDG GSEDCVEIFT NGKWNDRACG EKRLVVCEF

SP-hsTrailsyn-SPD-Konstrukt-2_PRO.PRO
KEYWORD PROTEIN
```

```
-continued
ORIGIN
                                                        SEQ ID NO: 27
    1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSGLP DVASLRQQVE ALQGQVQHLQ AAFSQYKKVE LFPNGQSVGE KIFKTAGFVK

241 PFTEAQLLCT QAGGQLASPR SAAENAALQQ LVVAKNEAAF LSMTDSKTEG KFTYPTGESL

301 VYSNWAPGEP NDDGGSEDCV EIFTNGKWND RACGEKRLVV CEF

ORIGIN
                                                        SEQ ID NO: 28
    1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSGLP DVASLRQQVE ALQGQVQHLQ AAFSQYKKVE LFPNG

SP-hsTrailsyn-coll11-Konstrukt-1.pro
KEYWORD PROTEIN
ORIGIN
                                                        SEQ ID NO: 29
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSQLRKAIG EMDNQVSQLT SELKFIKNAV AGVRETESKI YLLVKEEKRY ADAQLSCQGR

241 GGTLSMPKDE AANGLMAAYL AQAGLARVFI GINDLEKEGA FVYSDHSPMR TFNKWRSGEP

301 NNAYDEEDCV EMVASGGWND VACHTTMYFM CEFDKENM

SP-hsTrailsyn-coll-11-Konstrukt-2.pro
KEYWORD PROTEIN
ORIGIN
                                                        SEQ ID NO: 30
    1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSQLR KAIGEMDNQV SQLTSELKFI KNAVAGVRET ESKIYLLVKE EKRYADAQLS

241 CQGRGGTLSM PKDEAANGLM AAYLAQAGLA RVFIGINDLE KEGAFVYSDH SPMRTFNKWR

301 SGEPNNAYDE EDCVEMVASG GWNDVACHTT MYFMCEFDKE NM

SP-hsTrailsyn-coll-11-Konstrukt-3.pro
KEYWORD PROTEIN
ORIGIN
                                                        SEQ ID NO: 31
    1 METDTLLLWV LLLWVPGSTG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSQLR KAIGEMDNQV SQLTSELKFI KNAVAGVRET ES

FLAG-hColl1-hTRAIL_Glu116_Gly281.pro
KEYWORD PROTEIN
ORIGIN
                                                        SEQ ID NO: 32
    1 MNFGFSLIFL VLVLKGVQCD YKDDDDKGLP CECSQLRKAI GEMDNQVSQL TSELKFIKNA

61 VAGVRETESE RGPQRVAAHI TGTRGRSNTL SSPNSKNEKA LGRKINSWES SRSGHSFLSN

121 LHLRNGELVI HEKGFYYIYS QTYFRFQEEI KENTKNDKQM VQYIYKYTSY PDPILLMKSA

181 RNSCWSKDAE YGLYSIYQGG IFELKENDRI FVSVTNEHLI DMDHEASFFG AFLVG

FLAG-hColl1s-hTRAIL_Glu116_Gly281.pro
```

-continued

KEYWORD PROTEIN
ORIGIN
SEQ ID NO: 33
  1 MNFGFSLIFL VLVLKGVQCD YKDDDDKGLP CECSQLRKAI GEMDNQVSQL TSELKFIKNA

61 VAGVRETERG PQRVAAHITG TRGRSNTLSS PNSKNEKALG RKINSWESSR SGHSFLSNLH

121 LRNGELVIHE KGFYYIYSQT YFRFQEEIKE NTKNDKQMVQ YIYKYTSYPD PILLMKSARN

181 SCWSKDAEYG LYSIYQGGIF ELKENDRIFV SVTNEHLIDM DHEASFFGAF LVG hColl1s-hTRAIL_Glu116_Gly281.pro
KEYWORD PROTEIN
ORIGIN
SEQ ID NO: 34
  1 MNFGFSLIFL VLVLKGVQCG LPCECSQLRK AIGEMDNQVS QLTSELKFIK NAVAGVRETE

61 RGPQRVAAHI TGTRGRSNTL SSPNSKNEKA LGRKINSWES SRSGHSFLSN LHLRNGELVI

121 HEKGFYYIYS QTYFRFQEEI KENTKNDKQM VQYIYKYTSY PDPILLMKSA RNSCWSKDAE

181 YGLYSIYQGG IFELKENDRI FVSVTNEHLI DMDHEASFFG AFLVG

FLAG-hColl1-GSS-hTRAIL_Glu116_Gly281.pro
KEYWORD PROTEIN
ORIGIN
SEQ ID NO: 35
  1 MNFGFSLIFL VLVLKGVQCD YKDDDDKGLP CECSQLRKAI GEMDNQVSQL TSELKFIKNA

61 VAGVRETESG SSGSSGSSGS GERGPQRVAA HITGTRGRSN TLSSPNSKNE KALGRKINSW

121 ESSRSGHSFL SNLHLRNGEL VIHEKGFYYI YSQTYFRFQE EIKENTKNDK QMVQYIYKYT

181 SYPDPILLMK SARNSCWSKD AEYGLYSIYQ GGIFELKEND RIFVSVTNEH LIDMDHEASF

241 FGAFLVG

Sp1-hTRAIL_Glu116_Gly281-GSS-coll11.pro
KEYWORD PROTEIN
ORIGIN
SEQ ID NO: 36
  1 MNFGFSLIFL VLVLKGVQCE RGPQRVAAHI TGTRGRSNTL SSPNSKNEKA LGRKINSWES

61 SRSGHSFLSN LHLRNGELVI HEKGFYYIYS QTYFRFQEEI KENTKNDKQM VQYIYKYTSY

121 PDPILLMKSA RNSCWSKDAE YGLYSIYQGG IFELKENDRI FVSVTNEHLI DMDHEASFFG

181 AFLVGSSGSS GSSGSGLPCE CSQLRKAIGE MDNQVSQLTS ELKFIKNAVA GVRETES

Sp3-hTRAIL_Glu116_Gly281-GSS-coll11.pro
KEYWORD PROTEIN
ORIGIN
SEQ ID NO: 37
  1 METDTLLLWV LLLWVPAGNG ERGPQRVAAH ITGTRGRSNT LSSPNSKNEK ALGRKINSWE

61 SSRSGHSFLS NLHLRNGELV IHEKGFYYIY SQTYFRFQEE IKENTKNDKQ MVQYIYKYTS

121 YPDPILLMKS ARNSCWSKDA EYGLYSIYQG GIFELKENDR IFVSVTNEHL IDMDHEASFF

181 GAFLVGSSGS SGSSGSGLPC ECSQLRKAIG EMDNQVSQLT SELKFIKNAV AGVRETES

SP-hsTrailsyn-SPD-Konstrukt-1_DNA.seq: 1045 bp
KEYWORD DNA (DNA coding sequence corresponding to SEQ ID NO: 26
starts at base position 16)
ORIGIN
SEQ ID NO: 38
  1 AAGCTTGCCG CCACCATGGA GACCGATACA CTGCTCTTGT GGGTGCTCTT GCTGTGGGTT

61 CCTGCAGGTA ATGGTCAAAG AGTCGCAGCT CACATCACTG GACTAGAGG CAGGAGTAAC

121 ACCCTGAGTT CTCCCAATTC CAAGAACGAG AAAGCCCTGG GTAGGAAGAT CAACTCCTGG

181 GAAAGCTCCA GAAGCGGCCA TAGCTTTCTT AGCAACCTCC ACTTGAGGAA TGGCGAACTT

241 GTGATCCATG AGAAGGGCTT CTACTACATC TACAGCCAGA CGTACTTCAG GTTCCAGGAG

301 GAAATCAAGG AGAACACCAA GAACGACAAG CAGATGGTGC AATACATCTA CAAGTACACG

361 TCATACCCTG ATCCTATACT GCTGATGAAG TCCGCCAGAA ACAGTTGCTG GAGCAAAGAC

421 GCTGAATACG GCCTGTATTC CATCTATCAG GGCGGTATCT TTGAACTCAA GGAGAACGAC

-continued

```
481 AGGATCTTCG TGTCTGTGAC AAACGAGCAT CTGATCGACA TGGACCATGA AGCGTCTTTC

541 TTCGGTGCCT TCTTGGTGGG ATCCGGTTTG CCAGATGTTG CTTCTTTGAG ACAACAGGTT

601 GAGGCTTTGC AGGGTCAAGT CCAGCACTTG CAGGCTGCTT TCTCTCAATA CAAGAAGGTT

661 GAGTTGTTCC CAAATGGTCA ATCTGTTGGC GAAAAGATTT TCAAGACTGC TGGTTTCGTC

721 AAACCATTCA CGGAGGCACA ATTATTGTGT ACTCAGGCTG GTGGACAGTT GGCCTCTCCA

781 CGTTCTGCCC TGAGAACGC CGCCTTGCAA CAATTAGTCG TAGCTAAGAA CGAGGCTGCT

841 TTCTTGAGCA TGACTGATTC CAAGACAGAG GGCAAGTTCA CCTACCCAAC AGGAGAATCC

901 TTGGTCTATT CTAATTGGGC ACCTGGAGAG CCCAACGATG ATGGCGGCTC AGAGGACTGT

961 GTGGAAATCT TCACCAATGG CAAGTGGAAT GACAGAGCTT GTGGAGAGAA GCGTTTGGTG

1021 GTCTGTGAGT TCTAATAGCG GCCGC
```

SP-hsTrailsyn-SPD-Konstrukt-2_DNA.seq: 1057 bp
KEYWORD DNA (DNA coding sequence corresponding to SEQ ID NO: 27
starts at base position 16)
ORIGIN

SEQ ID NO: 39

```
  1 AAGCTTGCCG CCACCATGGA GACCGATACA CTGCTCTTGT GGGTACTCTT GCTGTGGGTT

61 CCGGGATCTA CCGGTGAACG TGGTCCTCAA AGAGTCGCAG CTCACATCAC TGGGACTAGA

121 GGCAGGAGTA ACACCCTGAG TTCTCCCAAT TCCAAGAACG AGAAAGCCCT GGGTAGGAAG

181 ATCAACTCCT GGGAAAGCTC CAGAAGCGGC CATAGCTTTC TTAGCAACCT CCACTTGAGG

241 AATGGCGAAC TTGTGATCCA TGAGAAGGGC TTCTACTACA TCTACAGCCA GACGTACTTC

301 AGGTTCCAGG AGGAAATCAA GGAGAACACC AAGAACGACA AGCAGATGGT GCAATACATC

361 TACAAGTACA CGTCATACCC TGATCCTATA CTGCTGATGA AGTCCGCCAG AAACAGTTGC

421 TGGAGCAAAA CGCTGAATA CGGCCTGTAT CCATCTATC AGGGCGGTAT CTTTGAACTC

481 AAGGAGAACG ACAGGATCTT CGTGTCTGTG ACAAACGAGC ATCTGATCGA CATGGACCAT

541 GAAGCGTCTT TCTTCGGTGC CTTCTTGGTG GGATCCGGTT TGCCAGATGT TGCTTCTTTG

601 AGACAACAGG TTGAGGCTTT GCAGGGTCAA GTCCAGCACT TGCAGGCTGC TTTCTCTCAA

661 TACAAGAAGG TTGAGTTGTT CCCAAATGGT CAATCTGTTG GCGAAAAGAT TTTCAAGACT

721 GCTGGTTTCG TCAAACCATT CACGGAGGCA CAATTATTGT GTACTCAGGC TGGTGGACAG

781 TTGGCCTCTC CACGTTCTGC CGCTGAGAAC GCCGCCTTGC AACAATTAGT CGTAGCTAAG

841 AACGAGGCTG CTTTCTTGAG CATGACTGAT TCCAAGACAG AGGGCAAGTT CACCTACCCA

901 ACAGGAGAAT CCTTGGTCTA TTCTAATTGG GCACCTGGAG AGCCCAACGA TGATGGCGGC

961 TCAGAGGACT GTGTGGAAAT CTTCACCAAT GGCAAGTGGA ATGACAGAGC TTGTGGAGAG

1021 AAGCGTTTGG TGGTCTGTGA GTTCTAATAG CGGCCGC
```

EXAMPLES

1. Materials and Methods

1.1 Construction of TNF-SF-Proteins Stabilised by a C-Terminal Positioned Collectin Derived Trimerization Domain The trimerization motifs (Tables 2 and 3) derived from human Collectin-11 (Col11), the "coiled coil" of Collectin-11 (CC11), human pulmonary surfactant protein-D (SP-D), the "coiled coil" of SP-D (CCSPD) were fused C-terminally to the human receptor binding domain (RBD) of CD95L ("CD95L-RBD"; Glu142-Leu281), human TRAIL-RBD (Gln120-Gly281), human LIGHT-RBD (Glu91-Val240) and human APRIL-RBD (Lys113-Leu250), respectively.

TABLE 2

List of the used regions from wild type (wt) sequences for the construction of trimerizing motifs.

| Trimerization motif | Amino acids of the unprocessed wt sequences used for motif construction | Swiss-Prot entry |
|---|---|---|
| SPD | 220-375 | P35247 |
| SPD_F335A | 220-375; Phe355 –> Ala355 | P35247 |
| SPD_F335D | 220-375; Phe355 –> Asp355 | P35247 |
| CCSPD | 220-257 | P35247 |
| Col11 | 117-271 | Q9BWP8 |
| CC11 | 116-151 | Q9BWP8 |

TABLE 3

Explanation of C-terminal trimerization motifs used to generate stable TNFSF fusion proteins.

| Trimerization motif | Explanation |
|---|---|
| SPD | human Surfactant protein-D (coiled-coiled "neck" + Carbohydrate Recognition Domain, CRD) |
| SPD_F335A | as in 1, but with the mutation Phe –> Ala at position 335 (numbering referring to processed wild type SP-D) |
| SPD_F335D | as in 1, but with the mutation Phe –> Asp at position 335 (numbering referring to processed wild type SP-D) |
| CCSPD | coiled-coiled "neck" of human SP-D |
| Col11 | human Collectin-11 (coiled-coiled "neck" + CRD of human Collectin-11) |
| CC11 | coiled-coiled "neck" of human Collectin-11 |
| T4 | Bacteriophage T4 Whisker protein (WO2008025516) |
| 69 | Bacteriophage 69 Whisker protein (WO2008025516) |

Between the TNFSF-RBD and the trimerization domain, a flexible linker element was placed with varying lengths (Table 4):

1.2 Generation of Expression Constructs

The nucleic acid molecule encoding the fusion protein as described herein may be cloned into a suitable vector for expressing the fusion protein. The molecular tools necessary in order to generate such a vector are known to the skilled person and comprise restriction enzymes, vectors, and suitable host for propagating the vectors.

For purification and analytical strategies, a Strep-tag II (amino acid sequence WSHPQFEK) was added C-terminally. This affinity tag was linked to the trimerization domain by a flexible linker element (amino acid sequence PSSSSSSA). To allow for secretory based expression, signal peptides derived from human Igκ were fused to the N-termini of said proteins. The amino acid sequences of the fusion proteins were back-translated and their codon usage optimised for mammalian cell-based expression. Gene synthesis was done by ENTELECHON GmbH (Regensburg, Germany). The final expression cassettes were subcloned into pCDNA4-HisMax-backbone, using unique Hind-III- and Not-I-sites of the plasmid. All expression cassettes were routinely verified by DNA sequencing.

Data will be presented herein for the following constructs (Table 5a and 5b):

TABLE 5A

Overview of TRAIL fusion proteins with shown data. Filled circles indicate that data are presented. N.s., not shown.

| Motif | TRAIL (wild-type) | | | | TRAIL Mutein (R1-specific) | | | | TRAIL Mutein (R2-specific) | | | |
|---|---|---|---|---|---|---|---|---|---|---|---|---|
| | A | B | C | D | A | B | C | D | A | B | C | D |
| SPD | ● | ● | ● | ● | ● | n.s. | n.s. | ● | ● | n.s. | n.s. | ● |
| SPD_F335A | ● | n.s. | n.s. | n.s. | n.s. | n.s. | n.s. | n.s. | n.s. | n.s. | n.s. | n.s. |
| SPD_F335D | ● | n.s. | n.s. | n.s. | n.s. | n.s. | n.s. | n.s. | n.s. | n.s. | n.s. | n.s. |
| CCSPD | ● | ● | ● | ● | ● | n.s. | n.s. | ● | ● | n.s. | n.s. | ● |
| Col11 | ● | ● | ● | ● | n.s. | n.s. | n.s. | n.s. | n.s. | n.s. | n.s. | n.s. |
| CC11 | ● | ● | ● | ● | n.s. | n.s. | n.s. | n.s. | n.s. | n.s. | n.s. | n.s. |
| T4 | ● | ● | ● | ● | n.s. | n.s. | n.s. | n.s. | n.s. | n.s. | n.s. | n.s. |
| 69 | ● | ● | ● | ● | n.s. | n.s. | n.s. | n.s. | n.s. | n.s. | n.s. | n.s. |

TABLE 4

Linker names and amino acid sequence

| Linker name | Amino-acid sequence |
|---|---|
| A | GSS GSS GSS GS |
| B | GSS GSS GS |
| C | GSS GS |
| D | GS |

(G = glycine; S = serine)

TABLE 5b

Overview of LIGHT-, APRIL-, and CD95L-constructs with shown data.

| | LIGHT | APRIL | CD95L |
|---|---|---|---|
| Linker: | A | A | A |
| Motif | | | |
| SPD | ● | ● | ● |
| CCSPD | ● | ● | n.s. |
| Col11 | ● | ● | n.s. |
| 69 | ● | ● | n.s. |

Filled circles indicate that data are presented.
N.s., not shown.

1.3 Expression and Purification of Engineered Ligands of the TNF Superfamily Hek 293T cells grown in DMEM+GlutaMAX (GibCo) supplemented with 10% FBS, 100 units/ml Penicillin and 100 μg/ml Streptomycin were transiently transfected with plasmids encoding a fusion protein as described herein. Cell culture supernatant containing recombinant proteins were harvested three days post transfection and clarified by centrifugation at 300×g followed by filtration through a 0.22 μm sterile filter. For affinity purification, 4 ml of 50% Streptactin Sepharose (IBA GmbH, Göttingen, Germany) were packed to a 2 ml column and equilibrated with 30 ml phosphate buffered saline, pH 7.4 (PBS; Invitrogen Cat. 10010) or buffer W (100 mM Tris-HCl, 150 mM NaCl pH 8.0). The cell culture supernatant was applied to the column at 4° C. with a flow rate of 2 ml/min. Subsequently, the column was washed with PBS or buffer W and specifically bound proteins were eluted stepwise by addition of 5×2 ml buffer E (PBS or buffer W with 2.5 mM Desthiobiotin, pH 7.4). The protein content of the eluate fractions was analysed by absorption spectroscopy and by silver-stained SDS-PAGE. Postitive fractions were subsequently concentrated by ultrafiltration (Sartorius, Vivaspin, 10,000 Da cut-off) and further analysed by size exclusion chromatography (SEC).

SEC was performed on a Superdex 200 column using an Äkta chromatography system (GE-Healthcare). The column was equilibrated with PBS (Invitrogen Cat. 10010) and the concentrated, streptactin purified proteins were loaded onto the SEC column at a flow rate of 0.5 ml/min. The elution of was monitored by absorbance at 280 nm. The apparent molecular weight of purified proteins were determined based on calibration of the Superdex 200 column with gel filtration standard proteins (Bio-Rad GmbH, München, Germany).

1.4. Cell Death Assays

To analyze caspase activation, a cellular assay with the Jurkat A3 permanent human T-cell line (cat. no. CRL2570, ATCC) was used. Jurkat cells were grown in flasks with RPMI 1640-medium+GlutaMAX (GibCo) supplemented with 10% FBS (Biochrom), 100 units/ml Penicillin and 100 μg/ml Streptomycin (GibCo). Prior to the assay, 100,000 cells were seeded per well into a 96-well microtiterplate. The addition of different solutions containing the protein with or without a crosslinking antibody to the wells (final volume: 200 μl) was followed by a 3 hour incubation at 37° C. Cells were lysed by adding 20 μl lysis buffer (250 mM HEPES, 50 mM $MgCl_2$, 10 mM EGTA, 5 Triton-X-100, 100 mM DTT, 10 mM AEBSF, pH 7.5) and plates were incubated on ice for 30 minutes to 2 hours. Apoptosis is paralleled by an increased activity of Caspases. Hence, cleavage of the specific Caspase substrate Ac-DEVD-AFC (Biomol) was used to determine the extent of apoptosis. For the Caspase activity assay, 20 μl cell lysate was transferred to a black 96-well microtiterplate. After the addition of 80 μl buffer containing 50 mM HEPES, 1% Sucrose, 0.1% CHAPS, 50 μM Ac-DEVD-AFC, and 25 mM DTT, pH 7.5, the plate was transferred to a Tecan Infinite F500 microtiterplate reader and the increase in fluorescence intensity was monitored (excitation wavelength 400 nm, emission wavelength 505 nm).

For the determination of cell death in HT1080 fibrosarcoma, HeLa cervix carcinoma and WM35 melanoma cells, 15,000 cells were plated in 96-well plates over night in RPMI 1640-medium+GlutaMAX (GibCo) supplemented with 10% FBS (Biochrom). For Colo205 cells, 50,000 cells were plated over night. Cells were stimulated the following day with indicated ligand and incubated for an additional 18 hours. For HeLa and HT1080 cells, cycloheximide (Sigma) at a final concentration of 2.5 μg/ml was used during stimulation with ligands. Cell death of HT1080, HeLa and WM35 was quantified by staining with buffer KV (0.5% crystal violet, 20% methanol). After staining, the wells were washed with water and air-dried. The dye was eluted with methanol and optical density at 595 nm was measured with an ELISA reader. Viability of Colo205 cells was quantified by MTS assay (Promega).

1.5 Hepatocellular Cytotoxicity Assay

To determine the effect of TRAIL fusion proteins, primary human hepatocytes were prepared from healthy donors and cultured in Williams E medium using 25,000 cells per well in 96-well plates. At day two, medium was changed to DMEM-F12 supplemented with 10% FCS, human insulin, Pen/Strep, minimum essential medium (MEM), sodium pyruvate and 10 mM Hepes and cultured for another day. Cells were stimulated at day three with varying concentrations of indicated proteins in presence or absence of cross-linking antibodies (StrepMabImmo, IBA GmbH). To evaluate the potential hepatotoxic effect of a cotreatment of ligands with chemotherapeutic agents, TRAIL-ASPD_F335D was coincubated at varying concentrations together with 5 mM of doxorubicin or 5 mM gemcitabine. Cells were incubated for 5 or 24 hours at 37° C. and 5% $CO_2$ and were then lysed for determination of caspase activity as described in section "Cell death assays".

1.6 Streptactin-ELISA

To determine the binding of receptors to constructed ligands, streptactin-coated 96-well microplates were used. Therefore, supernatants from transiently transfected HEK293 cells, mouse sera or purified proteins were immobilized on streptactin-plates (IBA GmbH) for 1-3 hours in PBS. Samples were diluted in ELISA binding/blocking buffer (PBS, 0.1% Tween-20, 20% SuperBlock T20-PBS (Pierce)). Plates were washed with PBS+0.1% Tween-20 and incubated with mouse-anti-TRAIL antibody (Pharmingen, clone RIK-2), TRAIL-Receptor 1-Fc (R&D Systems), TRAIL-Receptor 2-Fc (R&D Systems), TACI-Fc (R&D Systems) or HVEM-Fc (R&D Systems) for one hour at room temperature. Plates were again washed and Fc-proteins were detected with anti-human- or anti-mouse-Fc-specific peroxidase-conjugated antibodies (Sigma). Colour reaction was done by addition of 100 μl per well of TMB substrate (Kem-En-Tec Diagnostics) and the absorbance at 450 nm and 630 nm was determined with an ELISA reader after addition of 25 μl of 25% $H_2SO_4$ as stop-solution. Values were calculated as 450 nm-630 nm with MS Excel.

1.7 Mannan-Binding Assay

ELISA plates (Nunc Maxisorp) were incubated over night at 4° C. with 10 μg/well of yeast mannan (Sigma) in sterile coating buffer (15 mM $Na_2CO_3$, 35 mM $NaHCO_3$, 0.025%

NaN₃, pH 9.6). Plates were first incubated for one hour at room temperature with buffer BB (20 mM Tris, 140 mM NaCl, 5 mM CaCl₂, 0.1% BSA and 20% SuperBlock T20-PBS (Pierce)) and secondly for additional 90 minutes with varying concentrations of indicated ligands in buffer BB. Plates were washed with buffer WB (20 mM Tris, 140 mM NaCl, 5 mM CaCl₂, 0.05% Tween-20) and detection was done by using streptactin-HRP (IBA GmbH) in buffer BB. Plates were washed and developed with TMB substrate (Kem-En-Tec Diagnostics). The absorption at 450 nm and 630 nm was determined with an ELISA reader after addition of 25 µl of 25% $H_2SO_4$ as stop-solution. Values were calculated as 450 nm-630 nm with MS Excel.

1.8 Pharmacokinetics of TRAIL-SPD Fusion Proteins

Male CD1 mice (Charles River) were intravenously injected with 10 µg protein dissolved in 300 µl PBS (Invitrogen). Blood was collected after 0 min (predose), 5 min, 30 min, 2 hours, 6 hours and 24 hours. For each time point, two samples were collected. Blood samples were processed to obtain serum and were stored at −15° C. The concentration of TRAIL-fusion proteins was determined using an ELISA as described below (chapter 1.9) and half-lives were calculated (GraphPad Prism v4.0).

1.9 ELISA for the Quantitation of TRAIL-Constructs in Mouse Sera

To quantitate the concentration of TRAIL proteins in mouse sera (originating from pharmacokinetic studies), an ELISA method employing 96-well microplates was used.

ELISA plates were coated for 1 h at 37° C. with 2 µg/ml mouse-anti-TRAIL (clone RIK-2; Pharmingen). After washing with PBS+0.1% Tween-20 and blocking the plate for 30 min at 37° C. with StartingBlock™ (Pierce), serum samples at a concentration of 0.2% and 5%, calibration samples and control samples were added and incubated for 1 h at 37° C. Calibration and control samples were prepared from the respective TRAIL batch (TRAIL-ASPD or TRAIL-ASPD-F335A or TRAIL-ASPD-F335D) and were supplemented with 0.2% or 5% non-treated pooled CD1-mouse serum to account for potential matrix effects. Control samples (high, medium and low concentration of the TRAIL-construct) were added as quality controls to ensure precision and accuracy of the TRAIL-quantitation in the given assay window. Plates were again washed and the StrepTag-containing TRAIL-constructs were detected with 1:1000 diluted StrepTactin-POD (IBA). All samples and proteins were diluted with ELISA buffer (PBS, 0.1% Tween-20, 5% StartingBlock (Pierce)). The colour reaction started after addition of 100 µl per well TMB substrate (Kem-En-Tec Diagnostics). the absorbance at 450 nm and 630 nm was determined with an ELISA reader after addition of 25 µl of 25% H2SO4 as stop-solution. Values were calculated as 450 nm-630 nm with MS Excel.

2. Results

2.1 Characterization of CD95L Fusion Protein (CD95L-ASPD)

From the Streptactin-affinity purified CD95L-ASPD 0.5 ml (0.86 mg protein) were loaded with a flow rate of 0.5 ml/min onto a Superdex200 column using PBS as running buffer. Fractions of 0.5 ml were collected (A1 to A11 are indicated). The retention volume of the major peak at 11.92 ml corresponded to 170 kDa as determined from size exclusion standard. This indicated that the protein is a trimer composed of glycosylated monomers. The calculated molecular weight of the monomeric polypeptide is 38 kDa. An aliquot of fractions A1 to A11 was used for SDS-PAGE and caspase activity. Only the defined trimeric peak (fractions A7 to A10) was used for final analyses. The results are shown in FIG. 1.

Figure 2:
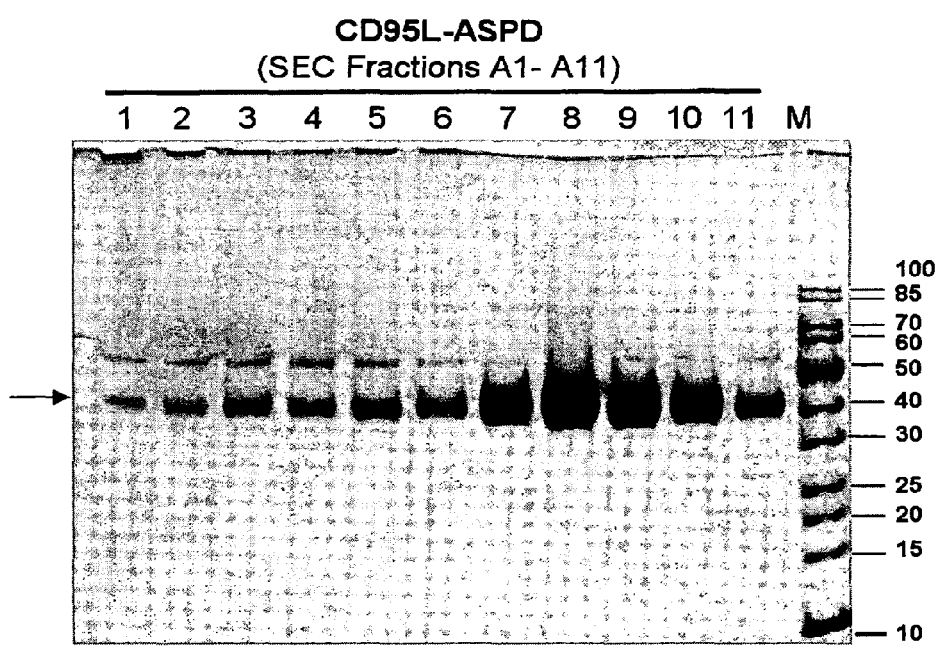
FIG. 2 shows silver gel of SEC fractions A1-A11 from affinity purified CD95L-ASPD.

An aliquot from size exclusion chromatography of affinity purified CD95L-ASPD was used for reducing SDS-PAGE followed by silver staining. The band detected at approximately 40-45 kDa (indicated by an arrow) corresponded to CD95L-ASPD. The trimeric species was present in fractions A7 to A10. The results are shown in FIG. 2.

Figure 3:
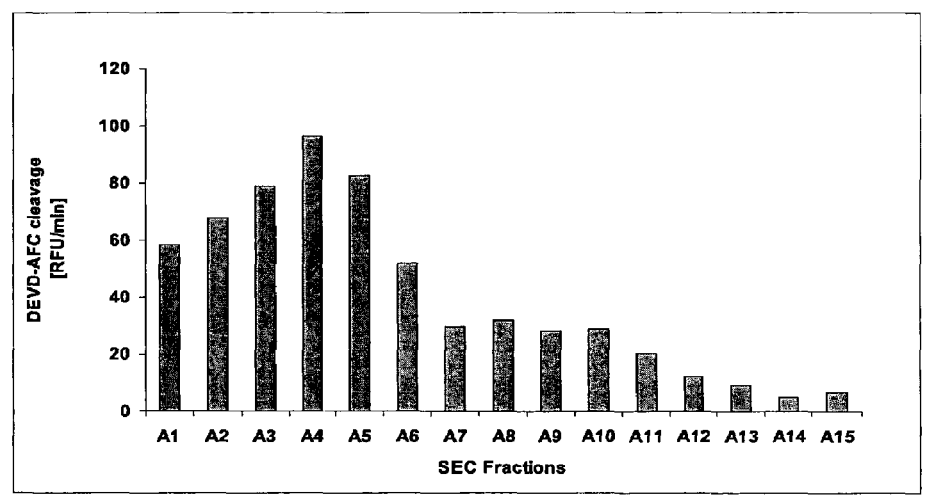
FIG. 3 shows caspase activity on Jurkat cells induced by SEC fractions A1-A15 from affinity purified CD95L-ASPD.

Jurkat cells were incubated with aliquots at a final 8-fold dilution from fractions A1 to A15 from SEC with affinity purified CD95L-ASPD. Cells were lysed after 3 h incubation and the caspase activity was determined with a fluorogenic assay. The fractions corresponding to the trimeric peak (fractions A7-A10) induced clear but weak caspase activity in Jurkat as these cells are known to require extensively cross-linked ligand. The aggregated and undefined species in fractions A1-A6 is therefore a potent inducer of caspase activation (not used further). Importantly, only the defined trimeric species (A7 to A10) was collected and used for final analyses. The results are shown in FIG. 3.

Figure 4:
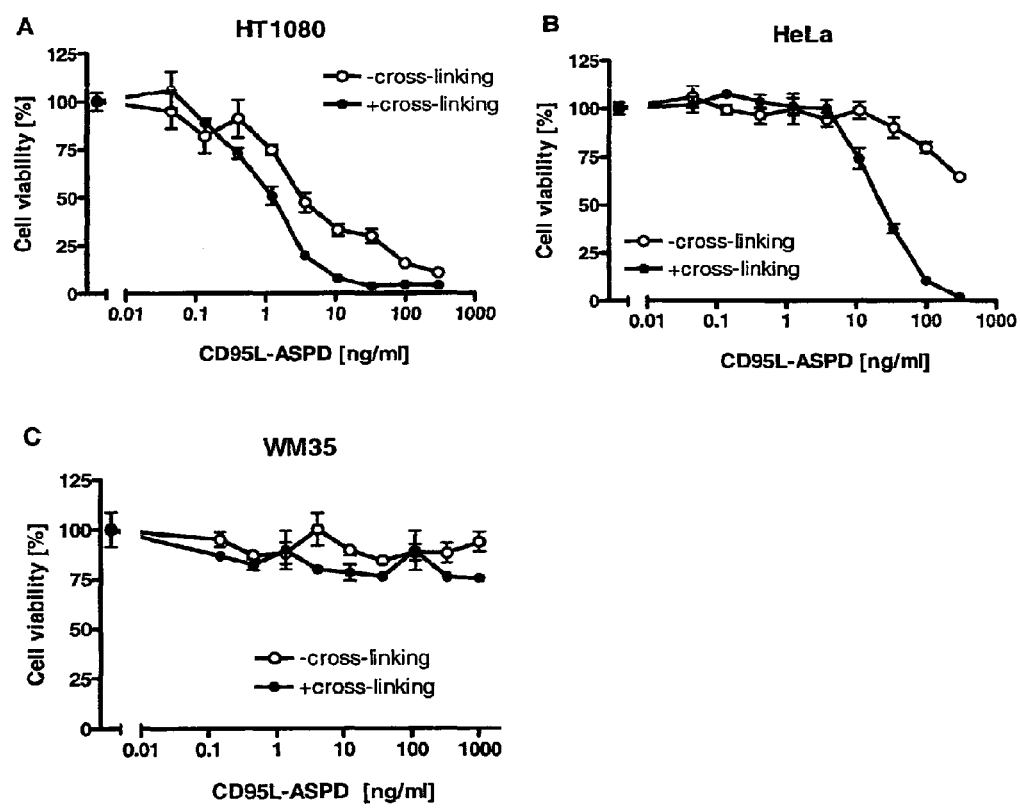
FIGS. 4A-C show cytotoxicity of CD95L-ASPD on WM35, HT1080 and HeLa cells.

The human cancer cell lines HT1080 (A), HeLa (B) or WM35 (C) were incubated with indicated concentrations of purified, trimeric CD95L-ASPD in the presence or absence of cross-linking antibody (2.5 microgram/ml of anti-Strep-tag II). Cells were incubated for 18 h and cytotoxicity was analyzed by crystal violet staining. As a result, CD95L-ASPD induced cell death in HeLa cervix cacinoma and HT1080 fibrosarcoma, but not in WM35 melanoma cells. The results are shown in FIG. 4.

The amino acid sequence of CD95L-ASPD is shown below.

```
Sp-CD95L-ASPD
Total amino acid number: 346, MW = 37682
ORIGIN
                                                                SEQ ID 40
   1 METDTLLLWV LLLWVPGSTG ELRKVAHLTG KSNSRSMPLE WEDTYGIVLL SGVKYKKGGL

61 VINETGLYFV YSKVYFRGQS CNNLPLSHKV YMRNSKYPQD LVMMEGKMMS YCTTGQMWAR

121 SSYVGAVFNL TSADHLYVNV SELSLVNFEE SQTFFGLYKL GSSGSSGSSG SGLPDVASLR

181 QQVEALQGQV QHLQAAFSQY KKVELFPNGQ SVGEKIFKTA GFVKPFTEAQ LLCTQAGGQL
```

```
                                     -continued
    241 ASPRSAAENA ALQQLVVAKN EAAFLSMTDS KTEGKFTYPT GESLVYSNWA PGEPNDDGGS 301 EDCVEIFTNG KWNDRACGEK RLVVCEFGGS PSSSSSSAWS HPQFEK
    1-20:    Secretion signal peptide (Sp; underlined)
    21-160:  CD95L-receptor binding domain
    161-171: Flexible linker element (A-linker; italic)
    172-209: Coiled coil "neck" region of human SP-D
    210-327: C-type lectin domain of human SP-D
    328-338: Linker element (GGSPSSSSSSA)
    339-346: Strep-tag II (WSHPQFEK)
```

2.2 Characterization of LIGHT Fusion Proteins (LIGHT-ASPD)

Figure 5:
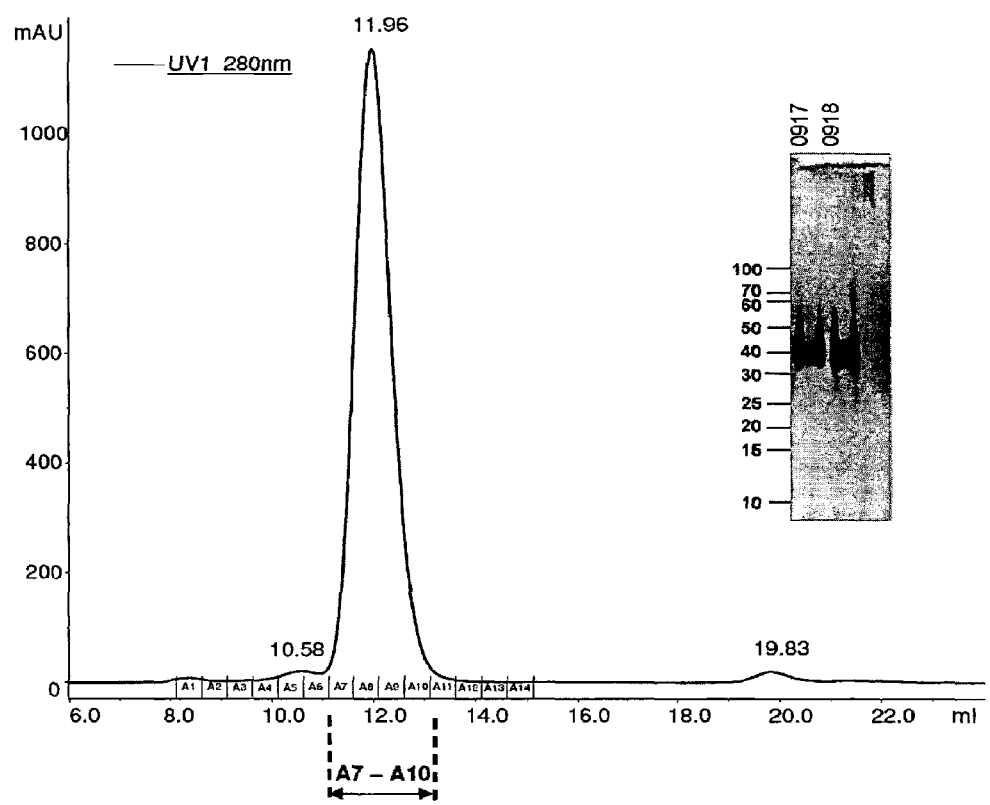
FIG. 5 shows SEC of affinity purified LIGHT-ASPD.

From affinity purified LIGHT-ASPD 0.5 ml (1.56 mg) were loaded onto a Superdex 200 column and resolved at 0.5 ml/min using PBS as running buffer. The major peak detected at 11.96 ml corresponded to a size of 170-180 kDa indicating that LIGHT-ASPD is a trimer composed of three glycosylated monomers. The trimeric peak (fractions A7 to A10) was collected and used for final analyses. The inset shows the silver stained SDS-PAGE of two independent purified and trimeric LIGHT-ASPD batches (designated 0917 and 0918). The results are shown in FIG. 5.

Figure 6:
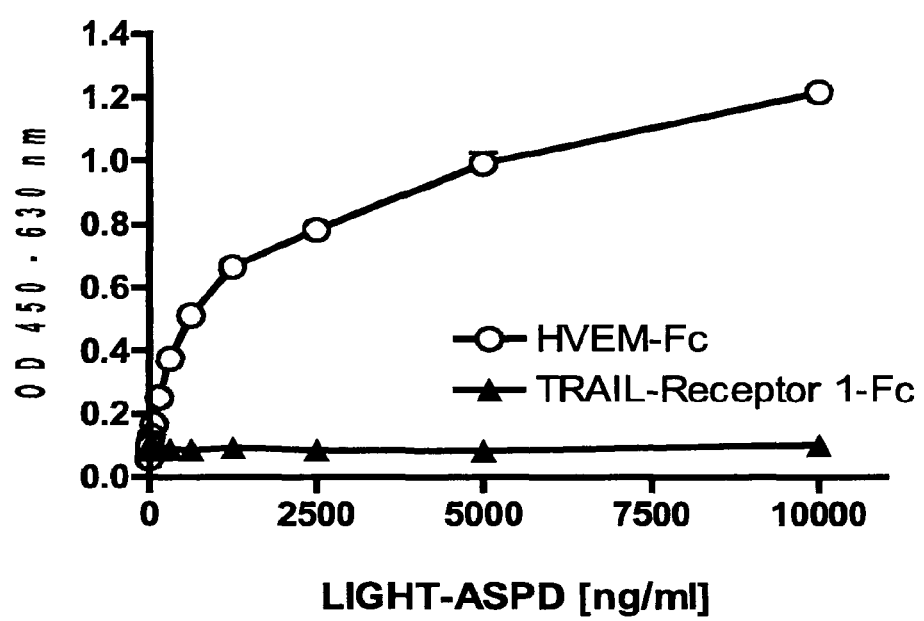
FIG. 6 shows binding of HVEM-Fc to immobilized LIGHT-ASPD.

Varying concentrations (0-10 microgram/ml) of affinity and SEC purified, trimeric LIGHT-ASPD were used for immobilized via the Strep-tag II on Streptactin-coated microplates. LIGHT-ASPD was then detected in a ELISA set-up using 100 ng/ml of Fc-fusion proteins of the receptors HVEM and TRAIL-Receptor 1, respectively. Whereas the ELISA signal increased for HVEM-Fc with increasing amounts of immobilized ligand, no signal was detected for TRAIL-Receptor 1-Fc over the whole range analyzed. This indicated that LIGHT-ASPD is a functional molecule that could bind to its receptor HVEM. The results are shown in FIG. 6.

The amino acid sequence of the LIGHT-ASPD fusion protein is shown below:

TABLE 6

Overview fusion proteins produced by transient transfection of expression vecors. The ligand TRAIL was transfected as fusion proteins comprising one of six stabilzing trimerization motifs and the linker element (A, B, C and D linker).

| No | Ligand | Linker  | Trimerization motif |
|----|--------|---------|---------------------|
| 1  | TRAIL  | A/B/C/D | 69                  |
| 2  | TRAIL  | A/B/C/D | T4                  |
| 3  | TRAIL  | A/B/C/D | SPD                 |
| 4  | TRAIL  | A/B/C/D | CCSPD               |
| 5  | TRAIL  | A/B/C/D | Col11               |
| 6  | TRAIL  | A/B/C/D | CC11                |

Supernatants were used for SDS-PAGE and TRAIL-constructs were detected by Western Blot analysis employing an antibody specific for Strep-tag II.

Figure 7:
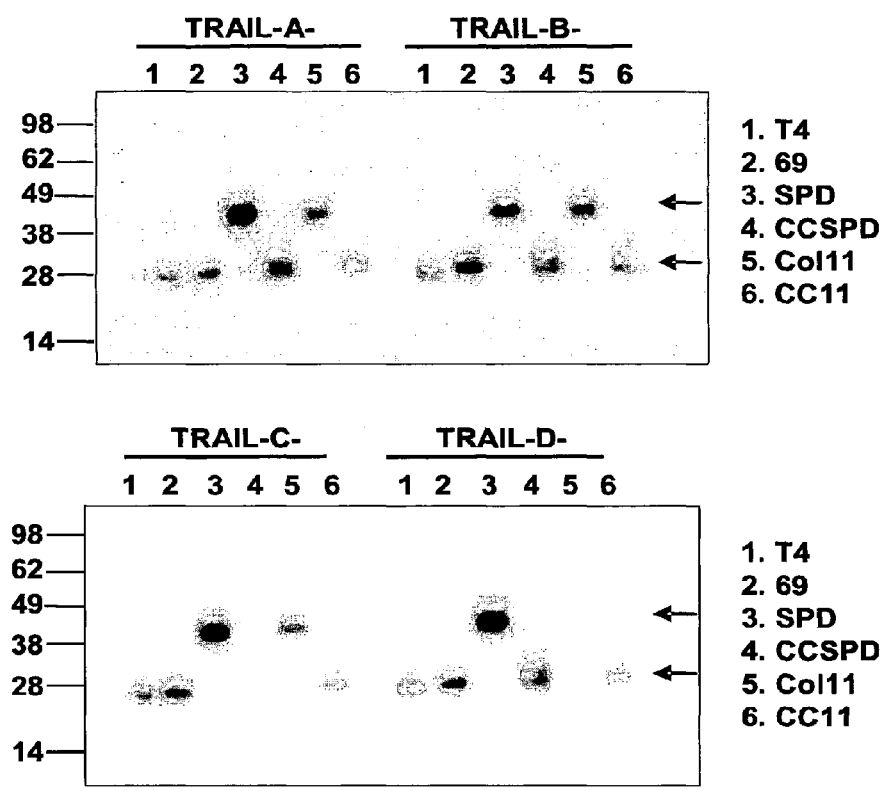
FIG. 7 shows western blot from transiently transfected HEK cells transiently transfected with TRAIL-constructs.

Specific bands detected are indicated by an arrow. The expression strength depended on the type of the trimerization motif employed for construction, (SPD>69/T4/Collectin11/CCSPD/CC11) as well as on the length of the linker element (A>B>C>D). The results are shown in FIG. 7.

Jurkat cells were incubated for three hours in the presence (filled bars, anti-Strep-tag II) or absence (clear bars) of a cross-linking antibody (2.5 micrograms/ml anti-Strep-tag II) with supernatants from transiently transfected HEK cells. Supernatants contained TRAIL-fusion proteins with different trimerization motifs (T4, 69, SPD, CCSPD, Col11, CC11)

```
Sp-LIGHT-ASPD
Total amino acid number: 356, MW = 37931
ORIGIN
                                                                SEQ ID 41
    1 METDTLLLWV LLLWVPGSTG EVNPAAHLTG ANSSLTGSGG PLLWETQLGL AFLRGLSYHD

61 GALVVTKAGY YYIYSKVQLG GVGCPLGLAS TITHGLYKRT PRYPEELELL VSQQSPCGRA

121 TSSSRVWWDS SFLGGVVHLE AGEEVVVRVL DERLVRLRDG TRSYFGAFMV GSGSGSGSSG

181 SGLPDVASLR QQVEALQGQV QHLQAAFSQY KKVELFPNGQ SVGEKIFKTA GFVKPFTEAQ

241 LLCTQAGGQL ASPRSAAENA ALQQLVVAKN EAAFLSMTDS KTEGKFTYPT GESLVYSNWA

301 PGEPNDDGGS EDCVEIFTNG KWNDRACGEK RLVVCEFGGS PSSSSSSAWS HPQFEK
1-20:    Secretion signal peptide (Sp; underlined)
21-170:  LIGHT-receptor binding domain
171-181: Flexible linker element (A-linker; italic)
182-219: Coiled coil "neck" region of human SP-D
220-337: C-type lectin domain of human SP-D
338-348: Linker element (GGSPSSSSSSA)
349-356: Strep-tag II (WSHPQFEK)
```

2.3 Characterization of TRAIL Fusion Proteins

HEK293 cells were transiently transfected with 24 different expression vectors encoding for TRAIL fusion proteins (Table 6).

fused through varying linker elements (A, B, C and D linker). As negative control, cell supernatant from untransfected cells was used. Jurkat cells were lysed and analyzed for caspase activity with a fluorogenic assay.

Figure 8:
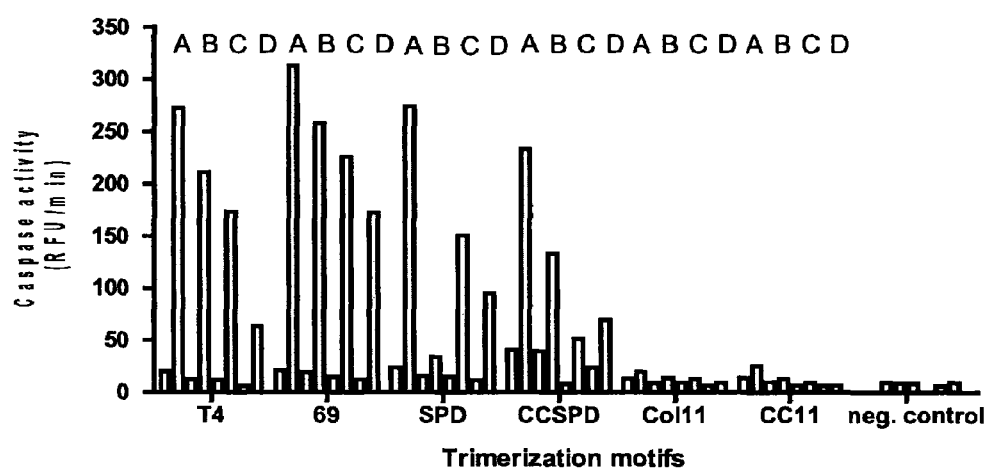
FIG. 8 shows caspase activity in Jurkat T-cells.

As a result, the caspase activity decreased with the type of linker element employed (A>B>C>D) and on the Fold-On employed. Collectin-11 or coiled coil of Collectin-11 (CCCol11) containing TRAIL constructs are expressed (shown by Western Blot analyses), however were not functional, whereas SPD-derived fold-on motifs yielded functional TRAIL-ligands. The results are shown in FIG. 8.

Figure 9:
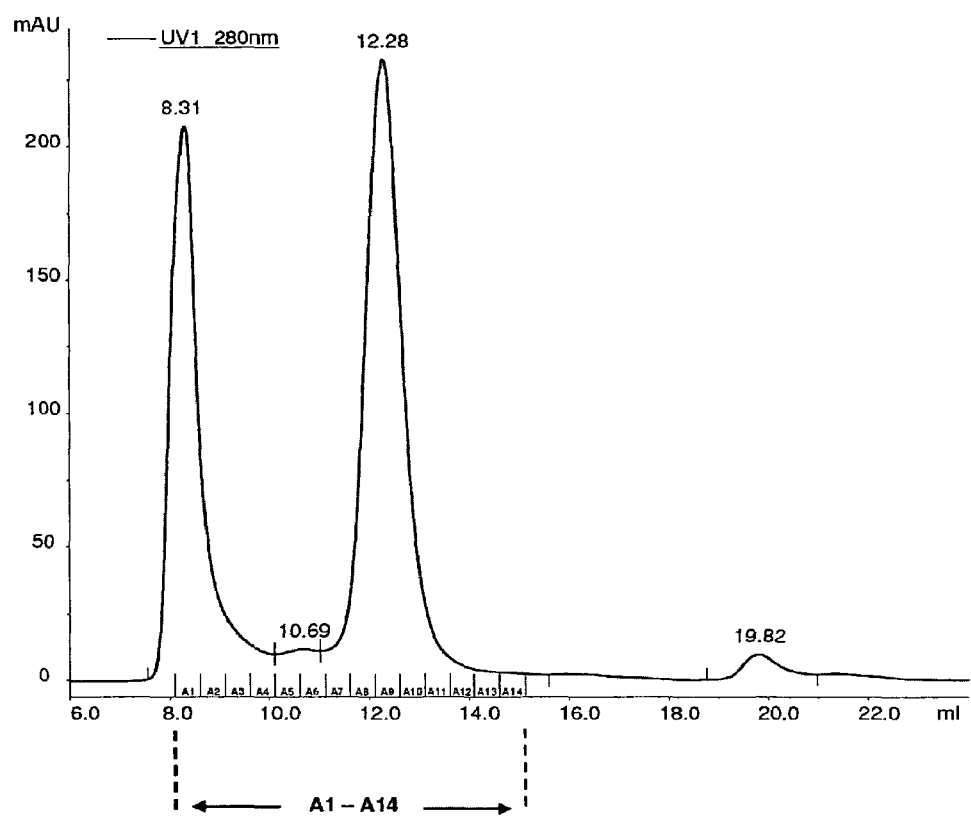
FIG. 9 shows size exclusion chromatography of TRAIL-ASPD.

Affinity purified TRAIL-ASPD was subjected to SEC by loading 0.5 ml (0.4 mg protein) to a Superdex200 column at 0.5 ml/min with PBS as running buffer. Protein elution was monitored by absorption at 280 nm and 0.5 ml fractions were collected. The retention volume of 12.28 ml corresponds to 135-140 kDa as determined from size exclusion standard. This indicated that TRAIL-ASPD is a homotrimer, as the calculated molecular weight of the monomeric polypeptide is 40 kDa. Importantly, for all fusion proteins analyzed by SEC consisting of the wild-type TRAIL-RBD sequence, an additional peak at around 8 ml corresponding to aggregated and non-active TRAIL-fusion protein was observed. From the collected fractions A1-A14 only the trimeric peak (A8-A10) was used for further analyses. The results are shown in FIG. 9.

Figure 10:
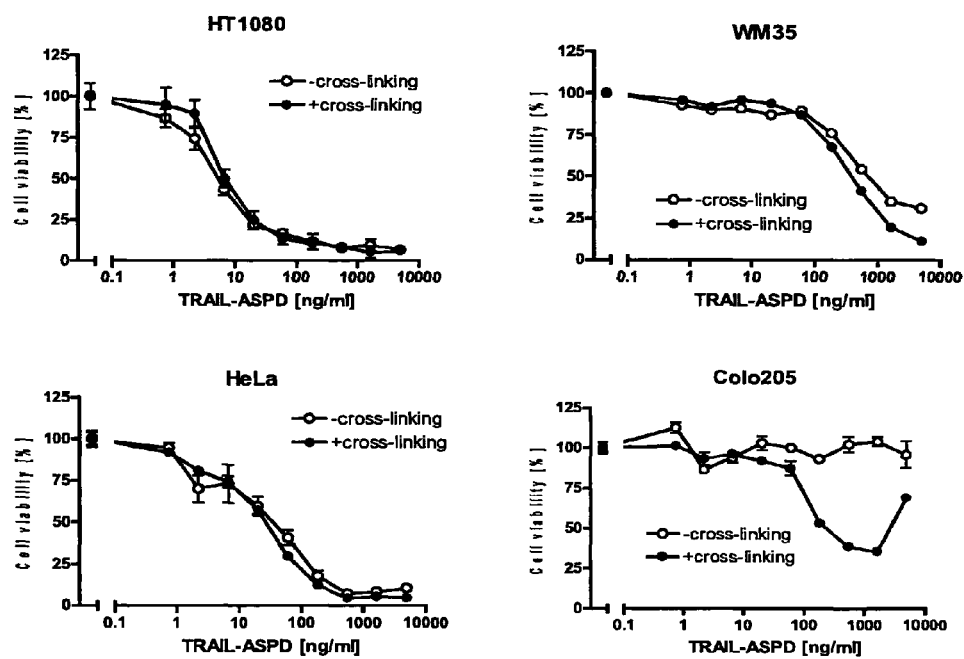
FIG. 10 shows cytotoxic activity of TRAIL-ASPD against human cancer cells.

The human cancer cell lines HeLa, HT1080, Colo205 or WM35 were incubated for 18 hours with indicated concentrations of purified, trimeric TRAIL-ASPD in the presence or absence of cross-linking antibody (2.5 microgram/ml of anti-Strep-tag II). Cell death was quantified by crystal violet staining (HeLa, WM35 and HT1080) or by MTS assay (Colo205). The rise in the viability of Colo205 cells at high ligand concentration is likely due to limitation of cross-linking antibody. The results are shown in FIG. 10.

Figure 11:
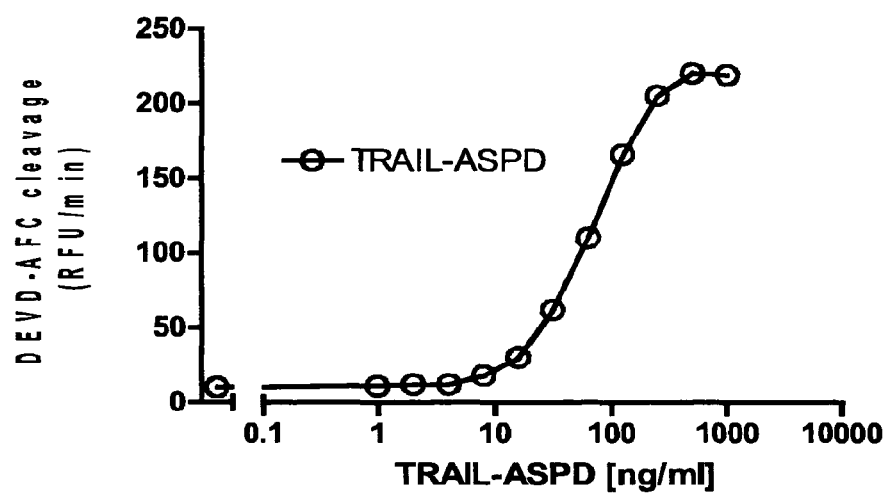
FIGS. 11A-B show TRAIL-ASPD induced caspase activity in Jurkat.
Figure 11:
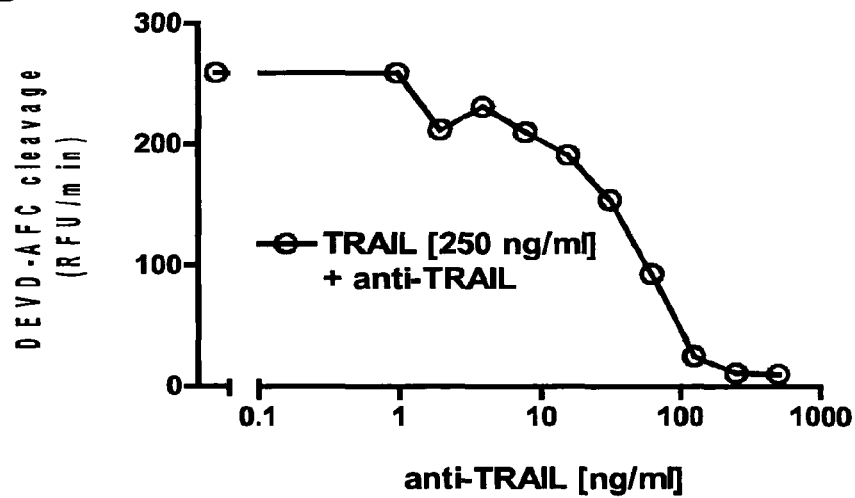

Varying (A) or a constant (B) concentration of affinity and SEC purified, trimeric TRAIL-ASPD was used for immobilization on Streptactin-coated 96-well plates. Plates were then incubated for 5 h with 100,000 Jurkat cells per well at 37° C., 5% CO2 and the caspase activity was determined with a fluorogenic assay. To analyze specificity, plate (B) was incubated for 30 minutes with indicated varying concentrations of an antagonistic anti-TRAIL antibody (clone RIK-2, Pharmingen) prior addition of cells. The results are shown in FIG. 11.

Figure 12:
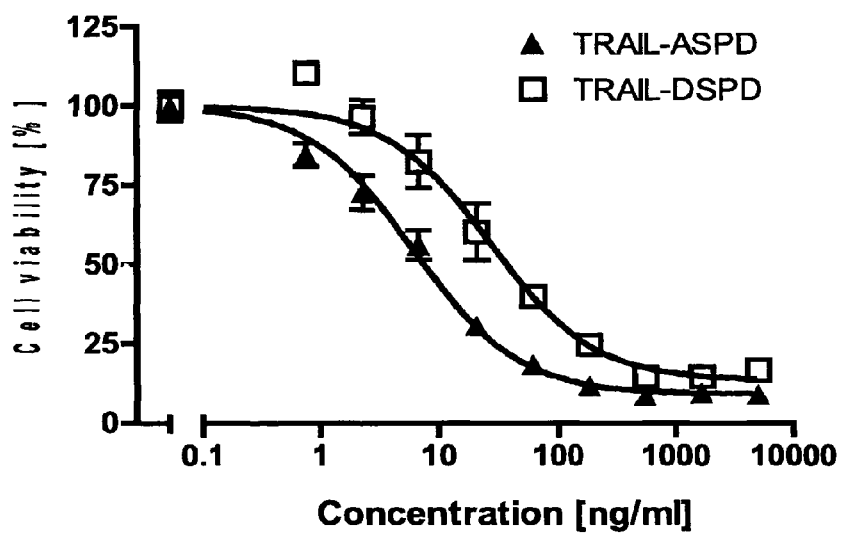
FIG. 12 shows cytotoxicity assay with TRAIL-ASPD or TRAIL-DSPD on HT1080 cells.

HT1080 cells were incubated on the same 96-well plate with purified and trimeric TRAIL-ASPD or TRAIL-DSPD at indicated concentrations. Cell death was quantified the following day by crystal violet staining. The use of the D-linker reduced the bioactivity approximately 4.5-fold, as indicated by the EC50 values of 27 ng/ml and 6 ng/ml for TRAIL-DSPD and TRAIL-ASPD, respectively. The results are shown in FIG. 12.

The nucleic acid and amino sequences of TRAIL fusion polypeptides are shown below.

```
SEQ ID 42: Expression cassette of Sp-TRAIL-ASPD
Endonuclease restriction sites are underlined (HindIII, AAGCTT;
BamHI, GGATCC; NotI, GCGGCCGC). The translational start codon is in
boldface.
ORIGIN
   1 AAGCTTGCCG CCACCATGGA GACCGATACA CTGCTCTTGT GGGTGCTCTT GCTGTGGGTT

61 CCTGCAGGTA ATGGTCAAAG AGTCGCAGCT CACATCACTG GACTAGAGG CAGGAGTAAC

121 ACCCTGAGTT CTCCCAATTC CAAGAACGAG AAAGCCCTGG GTAGGAAGAT CAACTCCTGG

181 GAAAGCTCCA GAAGCGGCCA TAGCTTTCTT AGCAACCTCC ACTTGAGGAA TGGCGAACTT

241 GTGATCCATG AGAAGGGCTT CTACTACATC TACAGCCAGA CGTACTTCAG GTTCCAGGAG

301 GAAATCAAGG AGAACACCAA GAACGACAAG CAGATGGTGC AATACATCTA CAAGTACACG

361 TCATACCCTG ATCCTATACT GCTGATGAAG TCCGCCAGAA ACAGTTGCTG GAGCAAAGAC

421 GCTGAATACG GCCTGTATTC CATCTATCAG GGCGGTATCT TTGAACTCAA GGAGAACGAC

481 AGGATCTTCG TGTCTGTGAC AAACGAGCAT CTGATCGACA TGGACCATGA AGCGTCTTTC

541 TTCGGTGCCT TCTTGGTGGG ATCCTCTGGT TCGAGTGGTT CGAGTGGTTC TGGATTGCCA

601 GACGTTGCTT CTTTGAGACA ACAGGTTGAG GCTTTGCAGG GTCAAGTCCA GCACTTGCAG

661 GCTGCTTTCT CTCAATACAA GAAGGTTGAG TTGTTCCCAA ACGGTCAATC TGTTGGCGAA

721 AAGATTTTCA AGACTGCTGG TTTCGTCAAA CCATTCACGG AGGCACAATT ATTGTGTACT

781 CAGGCTGGTG GACAGTTGGC CTCTCCACGT TCTGCCGCTG AGAACGCCGC CTTGCAACAG

841 TTGGTCGTAG CTAAGAACGA GGCTGCTTTC TTGAGCATGA CTGATTCCAA GACAGAGGGC

901 AAGTTCACCT ACCCAACAGG AGAATCCTTG GTCTATTCTA ATTGGGCACC TGGAGAGCCC

961 AACGATGATG GCGGCTCAGA GGACTGTGTG GAAATCTTCA CCAATGGCAA GTGGAATGAC

1021 AGAGCTTGTG GAGAGAAGCG TTTGGTGGTC TGTGAGTTCG GAGGCAGTCC TTCATCTTCA

1081 TCTAGCTCTG CCTGGTCGCA TCCACAATTC GAGAAATAAT AGCGGCCGC
```

-continued

SEQ ID 43 Sp-TRAIL-ASPD
Total amino acid number: 367, MW = 40404
ORIGIN
```
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIFTN GKWNDRACGE KRLVVCEFGG SPSSSSSSAW

361 SHPQFEK
```
1-20: Secretion signal peptide (Sp; underlined)
21-181: TRAIL-receptor binding domain
182-192: Flexible linker element (A-linker; italic)
193-230: Coiled coil "neck" region of human SP-D
231-348: C-type lectin domain of human SP-D
349-359: Linker element (GGSPSSSSSA)
360-367: Strep-tag II (WSHPQFEK)

SEQ ID 44 Sp-TRAIL-ACCSPD
Total amino acid number: 246, MW = 27534
ORIGIN
```
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG PSSSSSSAWS

241 HPQFEK
```
1-20: Secretion signal peptide (Sp; underlined)
21-181: TRAIL-receptor binding domain
182-192: Flexible linker element (A-linker; italic)
193-230: Coiled coil "neck" region of human SP-D
231-238: Linker element (PSSSSSSA)
239-246: Strep-tag II (WSHPQFEK)

SEQ ID 45 Sp-TRAIL-ACol11
Total amino acid number: 365, MW = 40806
ORIGIN
```
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSQLRKAIGE MDNQVSQLTS ELKFIKNAVA GVRETESKIY LLVKEEKRYA

241 DAQLSCQGRG GTLSMPKDEA ANGLMAAYLA QAGLARVFIG INDLEKEGAF VYSDHSPMRT

301 FNKWRSGEPN NAYDEEDCVE MVASGGWNDV ACHTTMYFMC EFDKENMGSP SSSSSSAWSH

361 PQFEK
```
1-20: Secretion signal peptide (Sp; underlined)
21-181: TRAIL-receptor binding domain
182-192: Flexible linker element (A-linker; italic)
193-224: Coiled coil "neck" region of human Collectin-11
225-347: C-type lectin domain of human Collectin-11
348-357: Linker element (GSPSSSSSSA)
358-365: Strep-tag II (WSHPQFEK)

SEQ ID 46 Sp-TRAIL-ACC11
Total amino acid number: 246, MW = 27431
ORIGIN
```
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGSQLRKAI GEMDNQVSQL TSELKFIKNA VAGVRETESG PSSSSSSAWS

241 HPQFEK
```
1-20: Secretion signal peptide (underlined)
21-181: TRAIL-receptor binding domain -continued 182-193: Flexible linker element (A-linker; *GSS GSS GSS GSG* italic)
194-229: Coiled coil "neck" region of human Collectin-11
230-238: Linker element (GPSSSSSA)
239-246: Strep-tag II (WSHPQFEK)

2.4 Characterization of Receptor-Selective TRAIL ('Mutein') Fusion Proteins

HEK293 cells were transiently transfected with expression plasmids encoding for different TRAIL receptor-selective SPD constructs:

| No. | Transfected Expression Vector |
|---|---|
| 1 | TRAILR1mut-A-SPD |
| 2 | TRAILR1mut-A-CCSPD |
| 3 | TRAILR1mut-D-SPD |
| 4 | TRAILR1mut-D-CCSPD |
| 5 | TRAILR2mut-A-SPD |
| 6 | TRAILR2mut-A-CCSPD |
| 7 | TRAILR2mut-D-SPD |
| 8 | TRAILR2mut-D-CCSPD |
| 9 | TRAIL-A-SPD |
| 10 | TRAIL-A-CCSPD |
| 11 | TRAIL-D-SPD |
| 12 | TRAIL-D-CCSPD |

Figure 13:
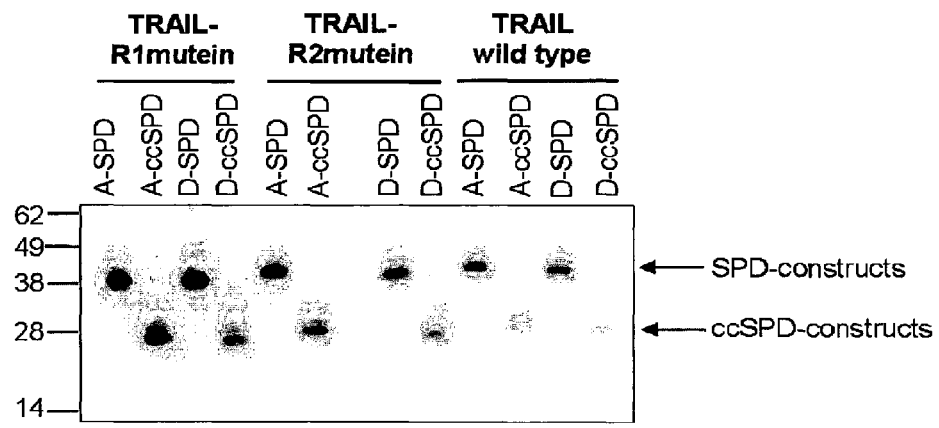
FIG. 13 shows western blot from transiently transfected HEK cells transiently transfected with TRAIL-SPD-constructs or TRAIL-receptor selective SPD constructs.

Supernatants were collected three days post-transfection and an aliquot was used for SDS-PAGE and Western Blotting employing an antibody specific for Strep-tag II. Specific bands were detected at around 38 kDa (SPD-fusion proteins) and 28 kDa (coiled-coil-SPD fusion proteins). The amount of expressed protein depended on the ligand itself (TRAILR1mutein>TRAILR2mutein>TRAIL), secondly the linker length used (A>D) and third the trimerization motif used (SPD>CCSPD). Apparent molecular weights were as expected from the calculated sizes (40 kDa and 27 kDa for SPD and CCSPD fusion proteins, respectively). The results are shown in FIG. 13.

Figure 14:
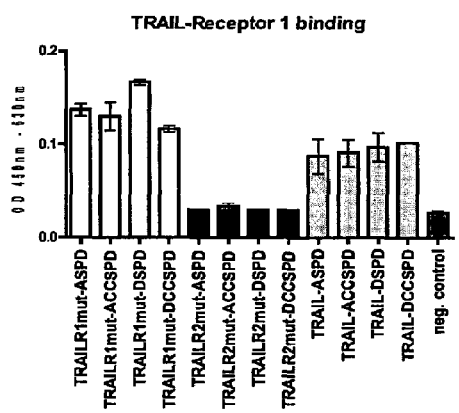
FIGS. 14A-D show TRAIL-Receptor selective ligands (TRAILR1 mut and TRAILR2mut) immobilized on Streptactin plates, are differently detected by TRAIL-Receptor 1-Fc or TRAIL-Receptor 2-Fc.
Figure 14:
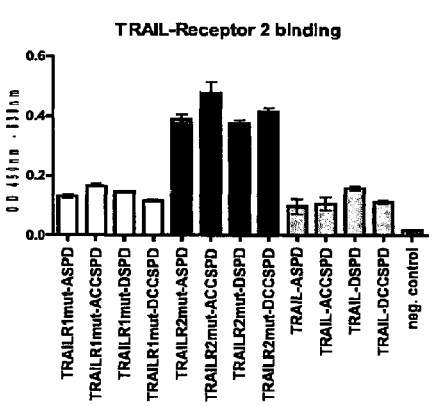
Figure 14:
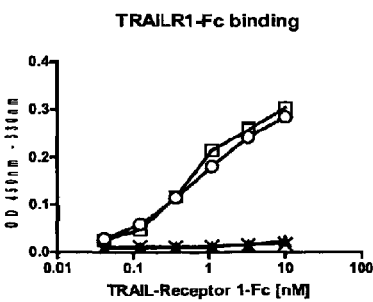
Figure 14:
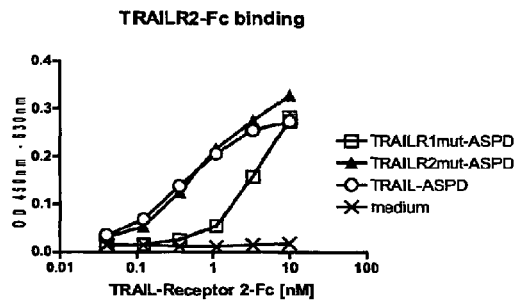

The selectivity of TRAIL-Receptor 1 or TRAIL-Receptor 2 towards fusion proteins of SPD/ccSPD and TRAIL, TRAILR1mut and TRAILR2mut was shown by Streptactin-ELISA. Therefore, TRAIL-SPD-fusion proteins in supernatants from transiently transfected HEK293 cells were immobilized on Streptactin coated microplates. Cell supernatant from untransfected cells served as negative control. The results are shown in FIG. 14. Specifically bound proteins were detected with constant (A, B) or varying (C, D) concentrations of either TRAIL-Receptor 1-Fc or TRAIL-Receptor 2-Fc. As shown in (A), the ligand TRAILR1 mut fused to SPD variants is detected by TRAIL-Receptor 1, whereas the ligand TRAILR2mut is not. As shown in (B), the ligand TRAILR2mut is preferentially detected by TRAIL-Receptor 2, whereas TRAILR1mut- and TRAIL wild-type constructs are equally well detected. As shown in C, TRAIL-Receptor 1-Fc bound to TRAIL-R1 mut-ASPD and TRAIL-ASPD equally well over the whole receptor titration range, whereas TRAIL-R2mut-ASPD is not detected. As shown in D, TRAIL-Receptor 2-Fc bound to TRAIL-R2mut-ASPD and TRAIL-ASPD equally well over the receptor titration range analyzed, whereas the signal for TRAIL-R1 mut-ASPD decreased rapidly with decreasing concentrations of receptor.

Figure 15:
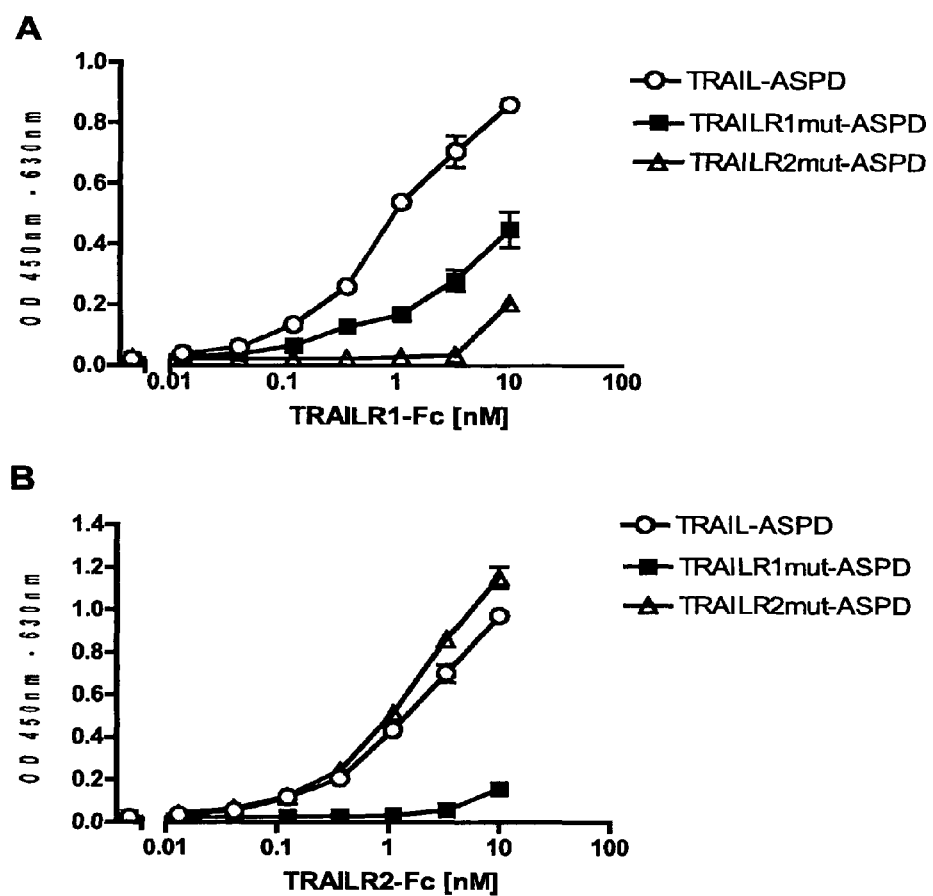
FIGS. 15A-B show binding of TRAIL-Receptors to Receptor-selective "mutein" ligands.

One microgram/ml of affinity purified, trimeric TRAIL-ASPD, TRAILR1mut-ASPD or TRAILR2mut-ASPD in 100 microliter of PBS were used for immobilization via the Strep-tag II on Streptactin-coated microplates. Bound ligands were detected in a ELISA set-up using Fc-fusion proteins of TRAIL-Receptor 1 (A) or TRAIL-Receptor 2 (B). As shown in (A), TRAIL-Receptor 1 bound preferentially to the receptor-selective TRAILR1mut-ASPD as compared to TRAILR2mut-ASPD. As shown in (B), TRAIL-Receptor 2 preferentially bound to TRAILR2mut-ASPD as compared to TRAILR1 mut-ASPD. In conclusion, the constructed TRAIL variants fused to SPD are receptor selective. The results are shown in FIG. 15.

Figure 16:
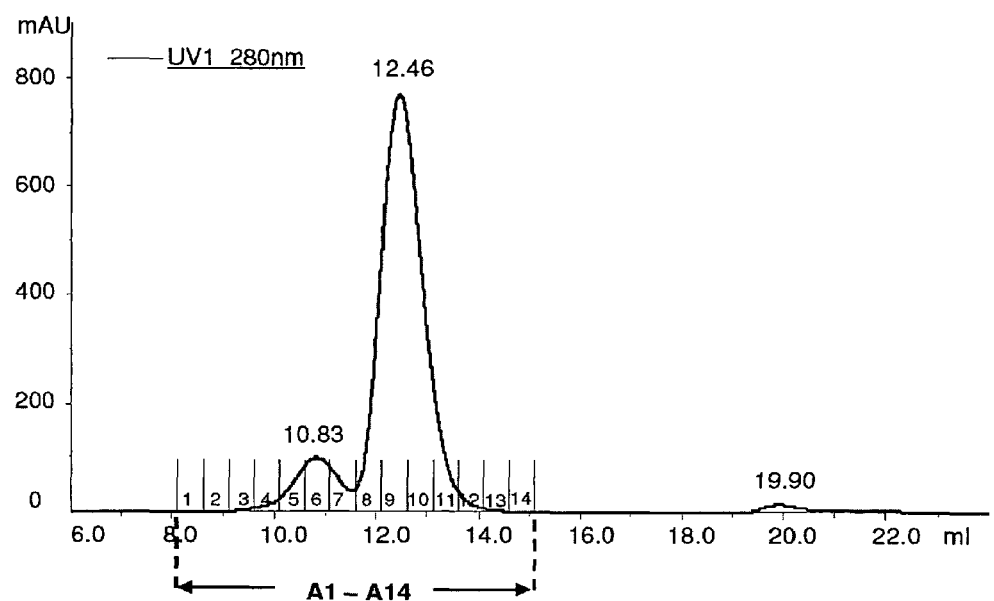
FIG. 16 shows size exclusion chromatography of affinity purified TRAILR1 mut-ASPD.

Affinity purified TRAILR1 mut-ASPD was subjected to SEC by loading 0.5 ml (0.95 mg protein) on a Superdex200 column. The results are shown in FIG. 16. Proteins were resolved at 0.5 ml/minute with PBS as running buffer and 0.5 ml fractions were collected (fractions A1 to A14 are indicated). The retention volume of 12.46 ml corresponded to 140-145 kDa as determined by size exclusion standard. A minor peak at 10.83 ml indicated some aggregated species, importantly however, no peak was detected at the running front (8 ml) indicating that this molecule is much more soluble as compared to proteins containing parts of the wild-type TRAIL amino acid sequence.

Figure 17:
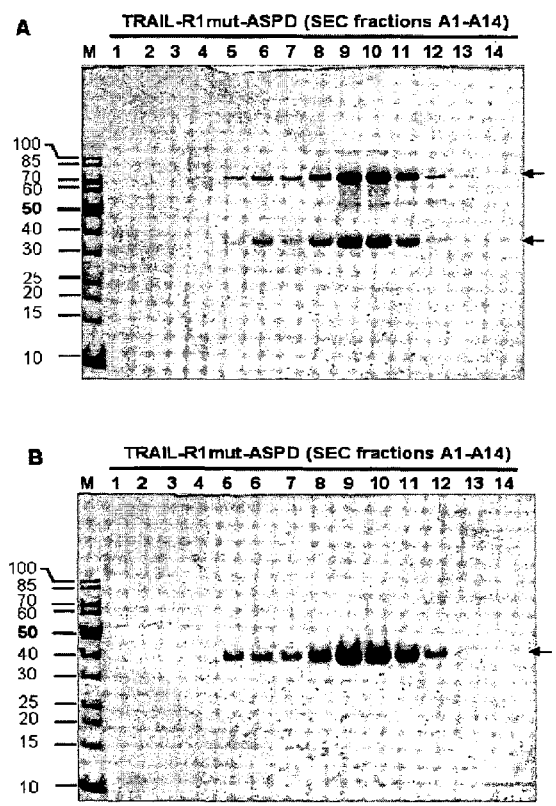
FIG. 17 shows silver stained SDS-PAGE of SEC fractions A1-A14 from affinity purified TRAILR1 mut-ASPD.

An aliquot from size exclusion chromatography of affinity purified TRAILR1mut-ASPD was used for non-reducing (A) or reducing (B) SDS-PAGE followed by silver staining as shown in FIG. 17. Under non-reducing conditions, two bands were detected at 35 and 70 kDa, whereas a single band of 40 kDa (indicated by an arrow) was detected under reducing conditions. This indicated the formation of disulphide bridged molecules. The trimeric species was present in fractions A8 to A11 and was used for later analyses.

Figure 18:
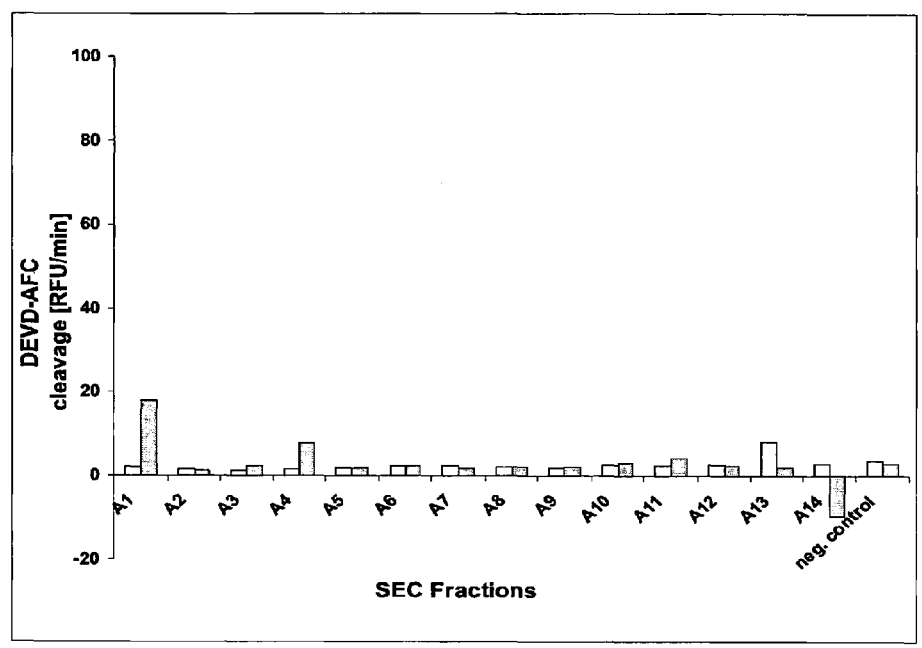
FIG. 18 shows caspase activity of SEC fractions A1-A14 from affinity purified TRAILR1 mut-ASPD on Jurkat cells.

Jurkat cells were incubated in the absence (open bars) or presence (filled bars) of 2.5 microgram/ml of cross-linking antibody with aliquots at a final 80-fold dilution from fractions A1 to A14 from SEC of affinity purified TRAILR1mut-ASPD. The results are shown in FIG. 18. As negative control, Jurkat cells were incubated with medium only. Jurkat cells were lysed after 3 h incubation and the caspase activity was determined with a fluorogenic assay. As Jurkat cells have been shown to mainly express TRAIL-Receptor 2, no fraction induced significant caspase activity, even when TRAILR1mit-ASPD was cross-linked by Strep-tag II specific antibody. This indicated that TRAILR1 mut-ASPD does not bind to TRAIL-Receptor 2.

Figure 19:
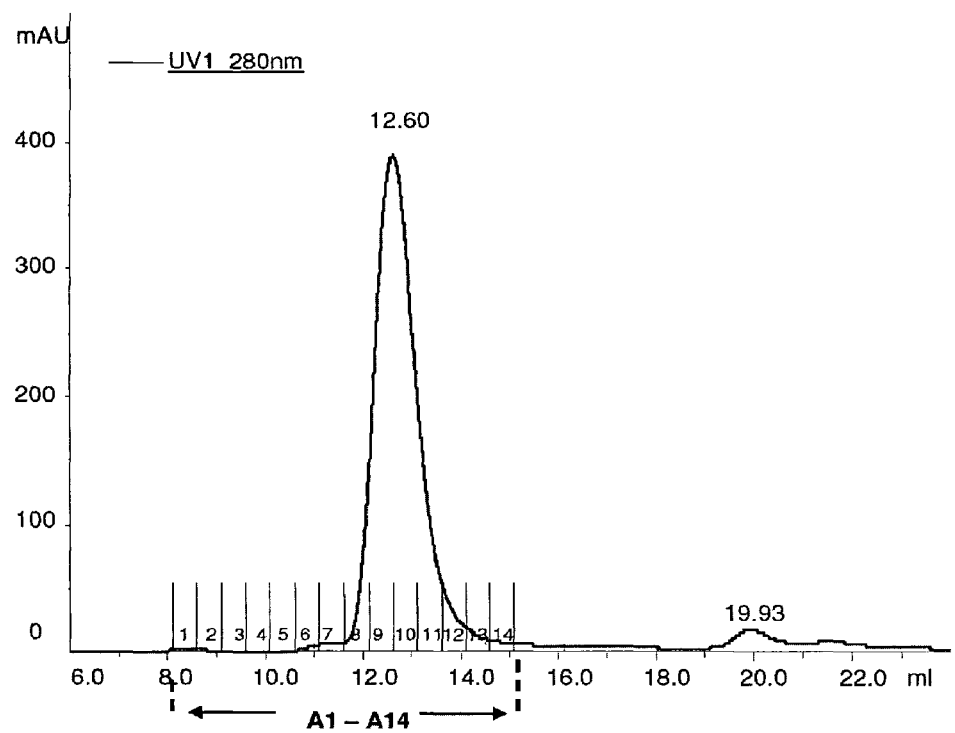
FIG. 19 shows size exclusion chromatography of affinity purified TRAILR2mut-ASPD.

Affinity purified TRAILR2mut-ASPD was subjected to size exclusion chromatography by loading 0.5 ml (0.5 mg protein) to a Superdex 200 column as shown in FIG. 19. Proteins were resolved at 0.5 ml/minute with PBS as running buffer and 0.5 ml fractions were collected (fractions A1 to A14 are indicated). The retention volume of 12.60 ml corresponds to 130-135 kDa as determined from size exclusion standard. This indicated that TRAILR2mut-ASPD is a homotrimer as calculated from the expected monomeric weight of 40 kDa. Importantly, more than 95% was present in the trimeric peak fraction and no aggregates were detected. The trimeric peak was used for later analyses.

Figure 20:
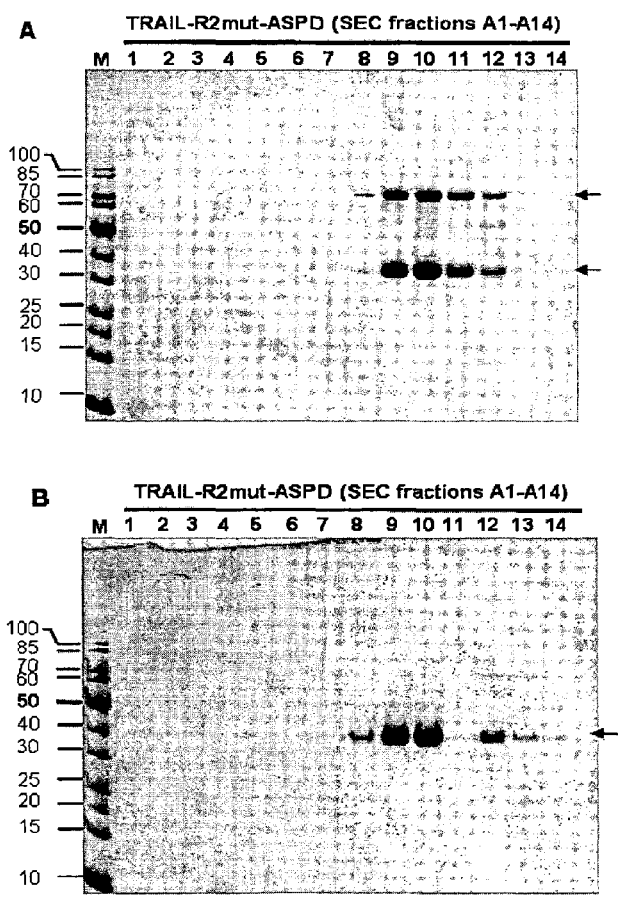
FIG. 20 shows silver stained SDS-PAGE of SEC fractions A1-A14 from affinity purified TRAILR2mut-ASPD.

An aliquot from size exclusion chromatography of affinity purified TRAILR2mut-ASPD was used for non-reducing (A) or reducing (B) SDS-PAGE followed by silver staining as shown in FIG. 20. Under non-reducing conditions, two bands were detected at 35 and 70 kDa, whereas a single band of approximately 40 kDa (indicated by an arrow) was detected under reducing conditions. This indicated the formation of disulphide bridged molecules. The trimeric species was present in fractions A9 to A11 and was used for later analyses.

Figure 21:
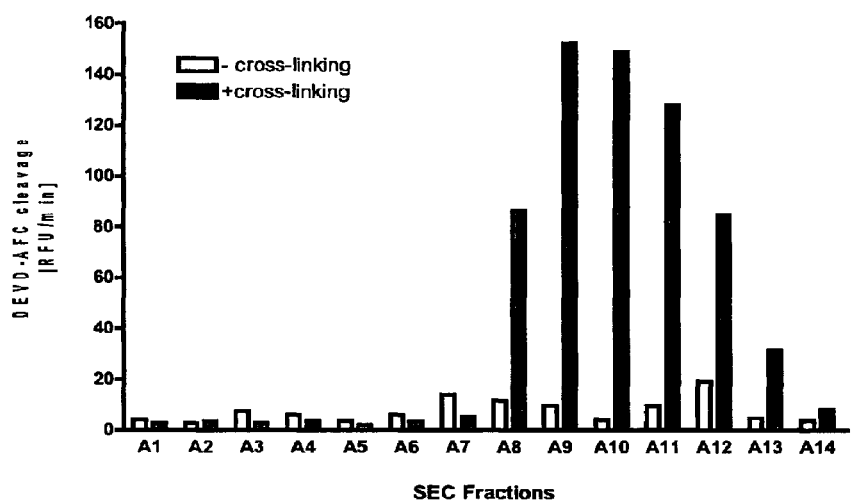
FIG. 21 shows Jurkat Kill Assay Jurkat of SEC fractions A1-A14 from affinity purified TRAILR2mut-ASPD.

The results from a Jurkat cell kill assay with TRAILR2-mut-ASPD are shown in FIG. 21. Jurkat cells were incubated in the absence (clear bars) or presence (filled bars) of cross-linking antibodies (2.5 microgram/ml anti-Strep-tag II) with aliquots from fractions A1 to A14 from SEC of affinity purified TRAILR2mut-ASPD. Samples were used at final 640-fold dilution. Cells were lysed after 3 h of incubation and the caspase activity was determined with a fluorogenic assay. As Jurkat cells have been shown to mainly express TRAIL-Receptor 2 that requires multimerized ligand forms for efficient signalling, TRAILR2mut-ASPD induced caspase activity when cross-linked. This indicated that TRAILR2mut-ASPD is a functional molecule.

Figure 22:
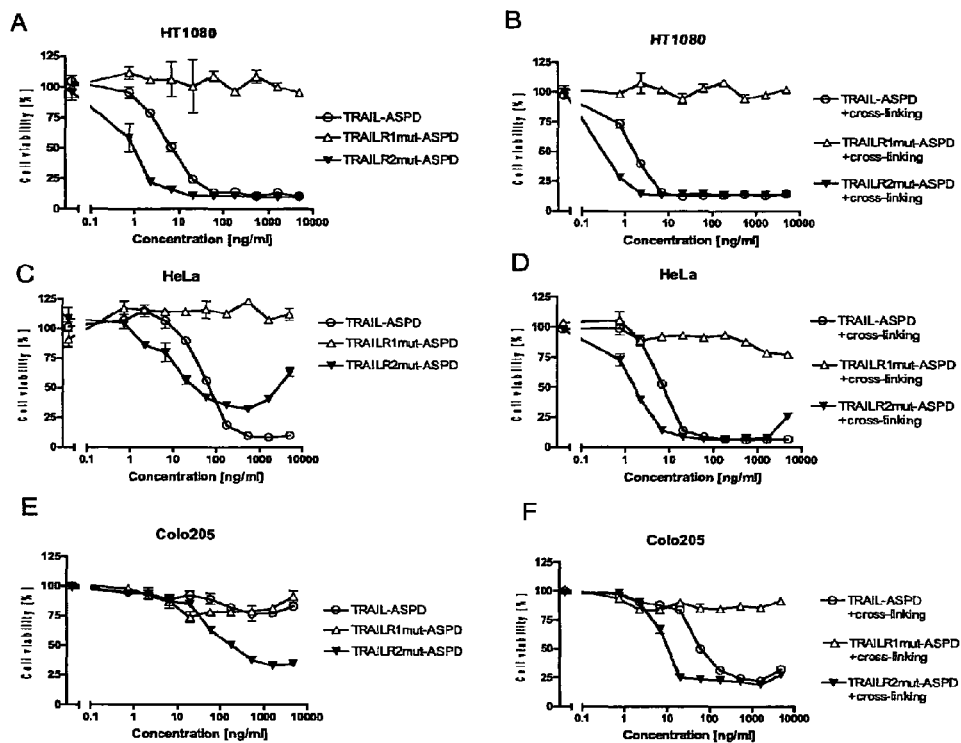
FIG. 22 shows cytotoxic activity of TRAIL-ASPD, TRAILR1 mut-ASPD and TRAILR2mut-ASPD on human cancer cells.

The cytotoxic activity of TRAIL-ASPD, TRAILR1 mut-ASPD and TRAILR2mut-ASPD on different human cancer cells is shown in FIG. 22. The indicated cell lines HT1080 (A and B), Hela (C and D) or Colo205 (E and F) were treated with varying concentrations of purified and trimeric TRAIL-ASPD, TRAILR1 mut-ASPD or TRAILR2mut-ASPD in the absence (A, C and E) or presence (B, D and F) of cross-linking antibody (anti-Strep-tag II). Cells were incubated for 18 hours with indicated concentrations of ligands and cell death was quantified by crystal violet staining (HT1080 and HeLa) or MTS assay (Colo205). As a result, the ligand TRAIL-ASPD induced cell death on the three cell lines tested and TRAILR2mut-ASPD showed superior cell killing activity. In contrast, TRAIL-Receptor 1 selective TRAILR1mut-ASPD was not active on any cell line tested.

Figure 23:
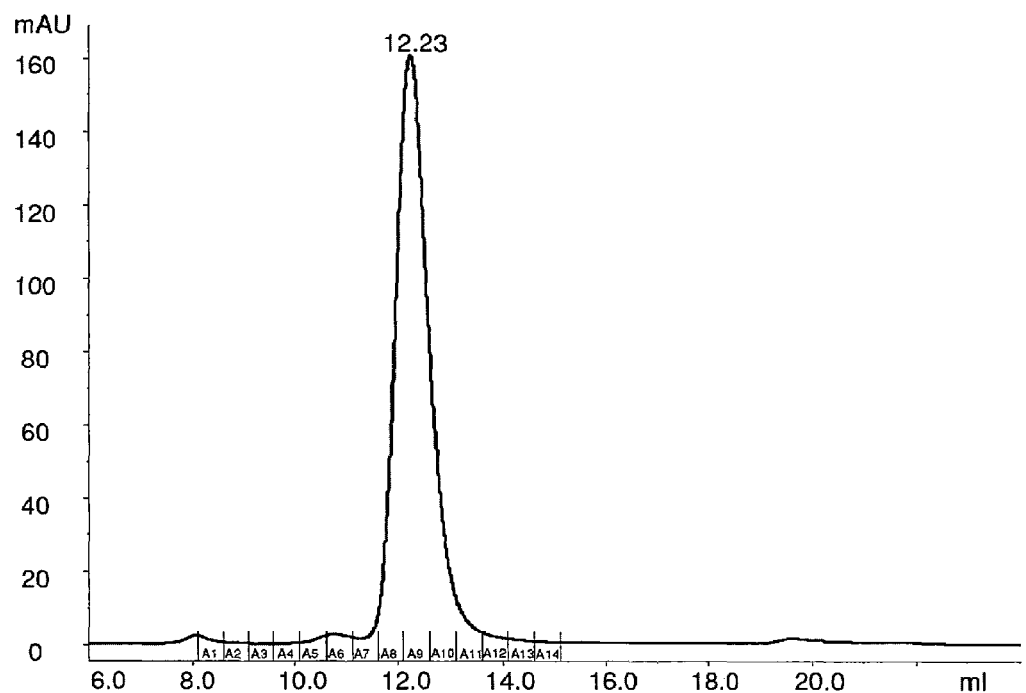
FIG. 23 shows receptor selective TRAIL-SPD proteins are highly soluble.

Affinity purified TRAILR2mut-ASPD was concentrated 20-fold in PBS by centrifugation through a 10 kDa membrane to give a solution of 2.5 mg/ml. From the concentrate, 0.1 ml were subjected to size exclusion chromatography. As a result, only the trimeric peak and no aggregates were detected, indicating that this composition has improved production capabilities (FIG. 23). Similar results were achieved for TRAILR1mut-ASPD, where a concentrated solution of even 5.4 mg/ml showed no signs of aggregation (not shown). In contrast, all fusion proteins tested containing the receptor binding domain composed of the wild type TRAIL sequence showed aggregation with 40% aggregates at concentrations as low as 0.4 mg/ml.

The amino acid sequences of receptor-selective TRAIL mutein fusion polypeptides are shown in the following.

```
Sp-TRAILR1mut-ASPD
Total amino acid number: 367, MW = 40335
ORIGIN
                                                             SEQ ID 47
    1 METDTLLLWV LLLWVPAGNG QRVAAHITGT RGRSNTLSSP NSKNEKALGR KINSWESSRS

61 GHSFLSNLHL RNGELVIHEK GFYYIYSQTA FRFSEEIKEV TRNDKQMVQY IYKWTDYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIFTN GKWNDRACGE KRLVVCEFGG SPSSSSSSAW

361 SHPQFEK
1-20: Secretion signal peptide (Sp; underlined)
21-181: TRAILR1mut-receptor binding domain
182-192: Flexible linker element (A-linker; italic)
193-230: Coiled coil "neck" region of human SP-D
231-348: C-type lectin domain of human SP-D
349-359: Linker element (GGSPSSSSSSA)
360-367: Strep-tag II (WSHPQFEK)

Sp-TRAILR2mut-ASPD
Total amino acid number: 367, MW = 40401
ORIGIN
                                                             SEQ ID 48
    1 METDTLLLWV LLLWVPAGNG QRVAAHITGT RGRSNTLSSP NSKNEKALGR KINSWESSRS

61 GHSFLSNLHL RNGELVIHEK GFYYIYSQTQ FKFREEIKEN TKNDKQMVQY IYKYTSYPDP

121 ILLMKSARNS CWSKDAEYGL YSIYQGGIFE LKENDRIFVS VTNERLLQMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIFTN GKWNDRACGE KRLVVCEFGG SPSSSSSSAW

361 SHPQFEK
1-20: Secretion signal peptide (Sp; underlined)
```

```
21-181: TRAILR2mut-receptor binding domain
182-192: Flexible linker element (A-linker; italic)
193-230: Coiled coil "neck" region of human SP-D
231-348: C-type lectin domain of human SP-D
349-359: Linker element (GGSPSSSSSSA)
360-367: Strep-tag II (WSHPQFEK)
```

2.5 Characterization of SPD Carbohydrate-Variants

Figure 24:
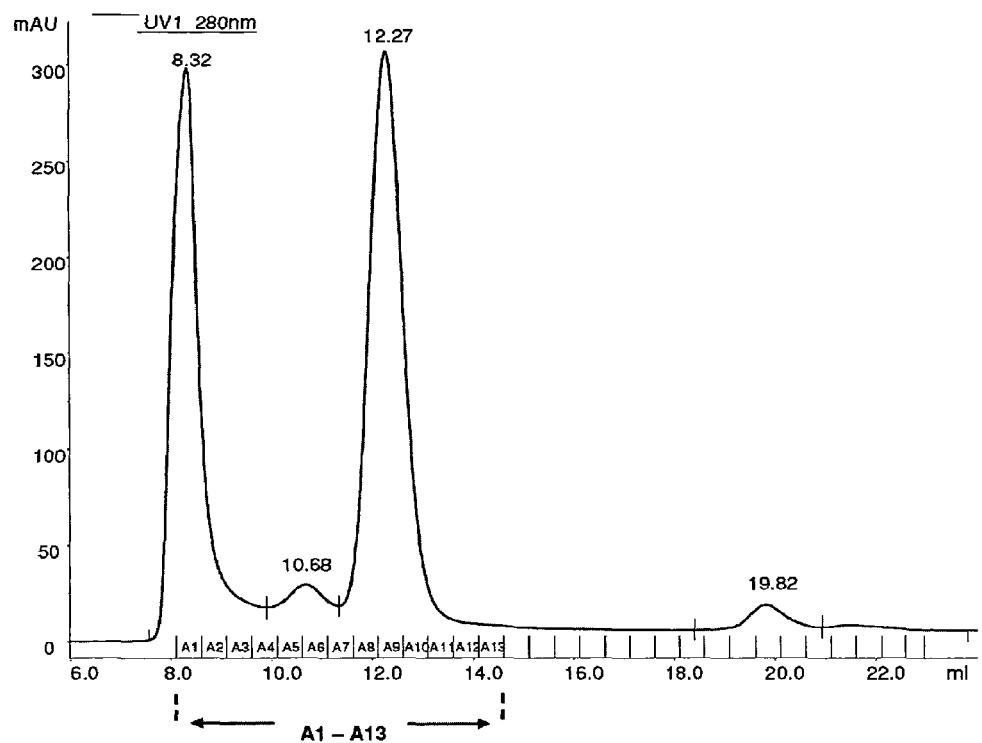
FIG. 24 shows SEC of affinity purified TRAIL-ASPD_F335A.

Affinity purified TRAIL-ASPD_F335A was subjected to Size Exclusion Chromatography by loading 0.5 ml PBS solution (0.4 mg protein) to a Superdex 200 column as shown in FIG. 24. Proteins were resolved at 0.5 ml/minute with PBS as running buffer and 0.5 ml fractions were collected (A1 to A13 are indicated). The retention volume of 12.27 ml corresponds to 135-145 kDa as determined from size exclusion standard.

Figure 25:
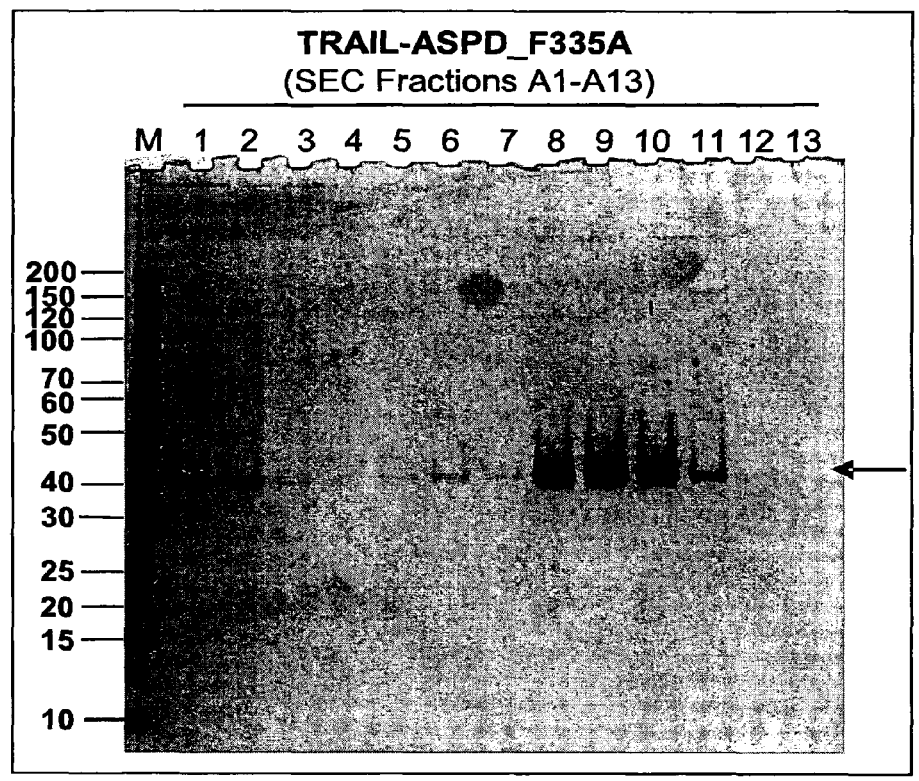
FIG. 25 shows silver stained SDS-PAGE of SEC fractions A1-A13.

PAGE and the gel was silver stained (FIG. 25). The band detected at approximately 40 kDa corresponded to the calculated molecular weight of 40 kDa for TRAIL-ASPD_F335A. Positive fractions corresponding the trimeric molecule (A8, A9, A10) of the SEC run were pooled and used for further analyses.

The amino acid sequences of TRAIL-SPD carbohydrate variant fusion proteins is shown in the following.

```
SEQ ID 49: Sp-TRAIL-ASPD_F335A
Total amino acid number: 367, MW = 40328
ORIGIN
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIATN GKWNDRACGE KRLVVCEFGG SPSSSSSSAW

361 SHPQFEK
1-20: Secretion signal peptide (Sp; underlined)
21-181: TRAIL-receptor binding domain
182-192: Flexible linker element (A-linker; italic)
193-230: Coiled coil "neck" region of human SP-D
231-348: C-type lectin domain of human SP-D (Phe mutation in bold-face)
349-359: Linker element (GGSPSSSSSSA)
360-367: Strep-tag II (WSHPQFEK)

SEQ ID 50: Sp-TRAIL-ASPD_F335D
Total amino acid number: 367, MW = 40372
ORIGIN
    1 METDTLLLWV LLLWVPAGNG QRVAAHITGT RGRSNTLSSP NSKNEKALGR KINSWESSRS

61 GHSFLSNLHL RNGELVIHEK GFYYIYSQTY FRFQEEIKEN TKNDKQMVQY IYKYTSYPDP

121 ILLMKSARNS CWSKDAEYGL YSIYQGGIFE LKENDRIFVS VTNEHLIDMD HEASFFGAFL

181 VGSSGSSGSS GSGLPDVASL RQQVEALQGQ VQHLQAAFSQ YKKVELFPNG QSVGEKIFKT

241 AGFVKPFTEA QLLCTQAGGQ LASPRSAAEN AALQQLVVAK NEAAFLSMTD SKTEGKFTYP

301 TGESLVYSNW APGEPNDDGG SEDCVEIDTN GKWNDRACGE KRLVVCEFGG SPSSSSSSAW

361 SHPQFEK
1-20: Secretion signal peptide (Sp; underlined)
21-181: TRAIL-receptor binding domain
182-192: Flexible linker element (A-linker; italic)
193-230: Coiled coil "neck" region of human SP-D
231-348: C-type lectin domain of human SP-D (Asp mutation in bold-face)
349-359: Linker element (GGSPSSSSSSA)
360-367: Strep-tagII (WSHPQFEK)
```

This indicated that TRAIL-ASPD_F335A is a homotrimer as calculated from the expected monomeric weight of 40 kDa. Two additional peaks at 8.32 and 10.68 ml indicated the formation of TRAIL-ASPD_F335A aggregates. Only the trimeric peak was used for later analyses.

Figure 26:
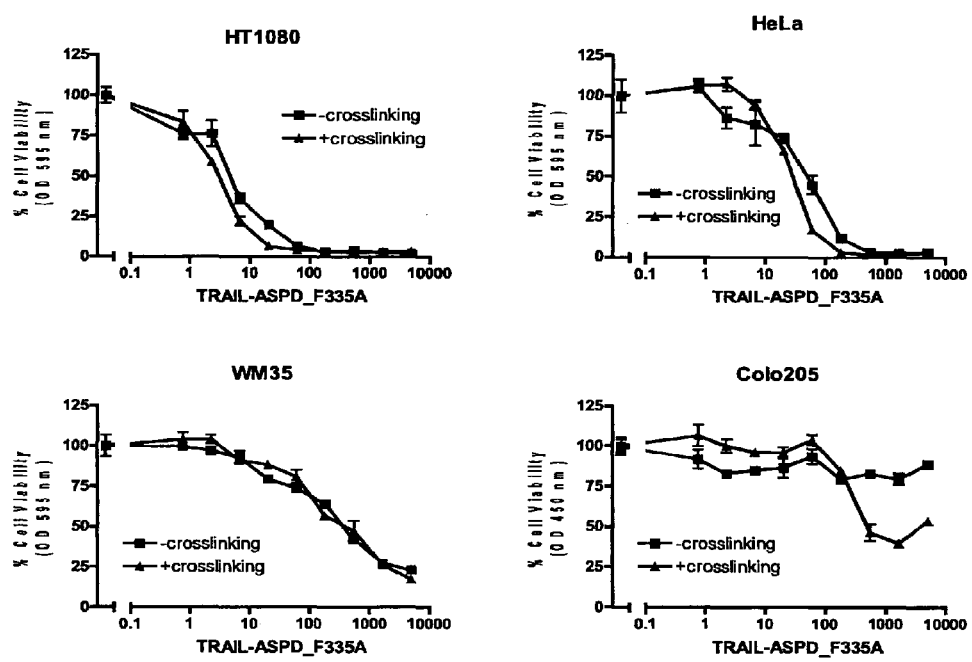
FIG. 26 shows cytotoxic effect of TRAIL-ASPD_F335A on human cancer cells.

From Size exclusion chromatography an aliquot from collected fractions A1 to A13 was resolved by reducing SDS- The cytotoxic effect of TRAIL-ASPD_F335A on human cancer cells is shown in FIG. 26. Indicated human cancer cell lines were incubated over night with varying concentrations of affinity and SEC purified, trimeric TRAIL-ASPD F335A in the presence or absence of cross-linking antibody (2.5 microgram/ml of anti Strep-tag II). Cell viability was quantified by crystal violet staining (HT1080, HeLa and WM35)

or MTS (Colo205). The rise of Colo205 cell viability at high ligand concentrations is likely due to limitation of cross-linking antibody.

Figure 27:
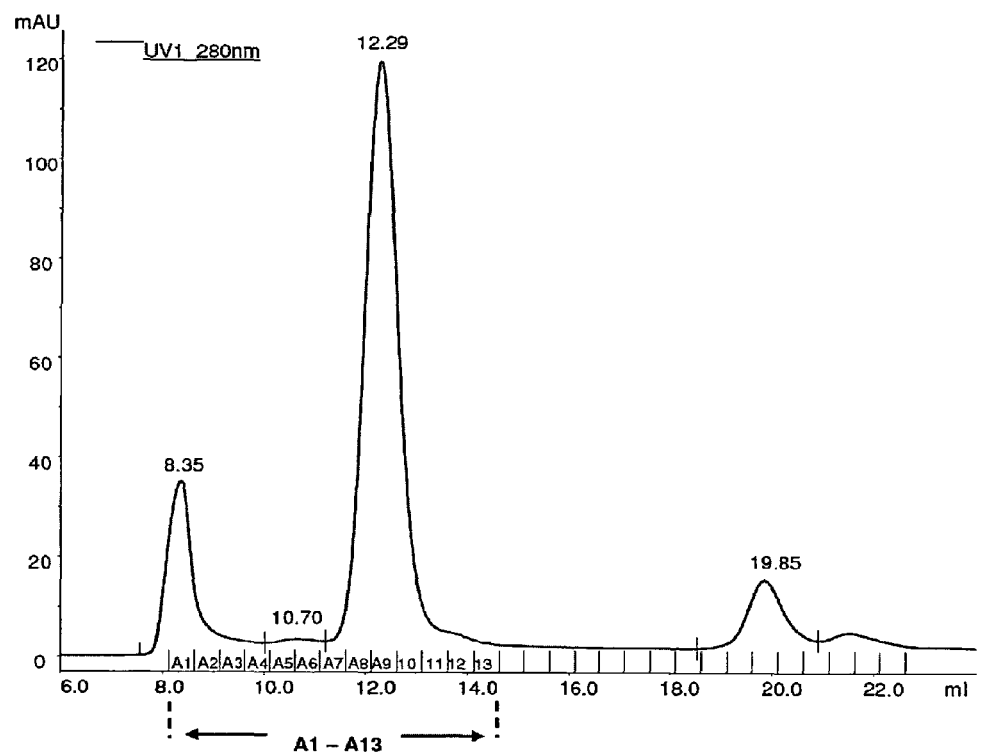
FIG. 27 shows SEC of affinity purified TRAIL-ASPD_F335D.

Affinity purified TRAIL-ASPD_F335D was subjected to Size Exclusion Chromatography by loading 0.5 ml (0.2 mg protein) to a Superdex 200 column as shown in FIG. 27. Proteins were resolved at 0.5 ml/minute with PBS as running buffer and 0.5 ml fractions were collected (A1 to A13 are indicated). The retention volume of 12.29 ml corresponds to 135-145 kDa as determined from size exclusion standard. This indicated that TRAIL-ASPD F335D is a homotrimer as calculated from the expected monomeric weight of 40 kDa. The peak at 8.35 corresponded to inactive TRAIL-ASPD_F335D aggregates typically found for all fusion proteins containing parts of the wild type TRAIL amino acid sequence.

Figure 28:
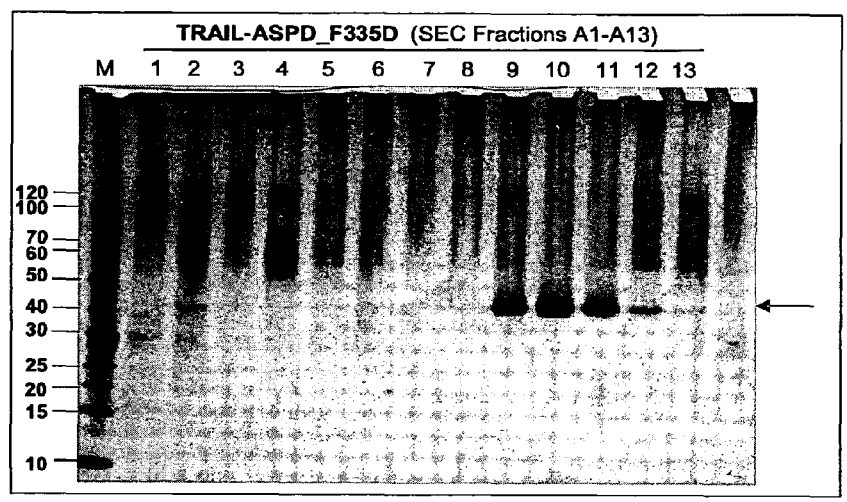
FIG. 28 shows silver stained SDS-PAGE of SEC from affinity purified TRAIL-ASPD_F335D.

From Size exclusion chromatography aliquots of affinity purified TRAIL-ASPD_F335D from the collected fractions A1 to A13 were resolved by reducing SDS-PAGE and the gel was silver stained (FIG. 28). The bands detected at approximately 40 kDa (indicated by an arrow) corresponded to the calculated molecular weight of 40 kDa for TRAIL-ASPD_F335D. Fractions containing trimeric protein (fractions A8 to A10) were pooled and used for further analyses.

Figure 29:
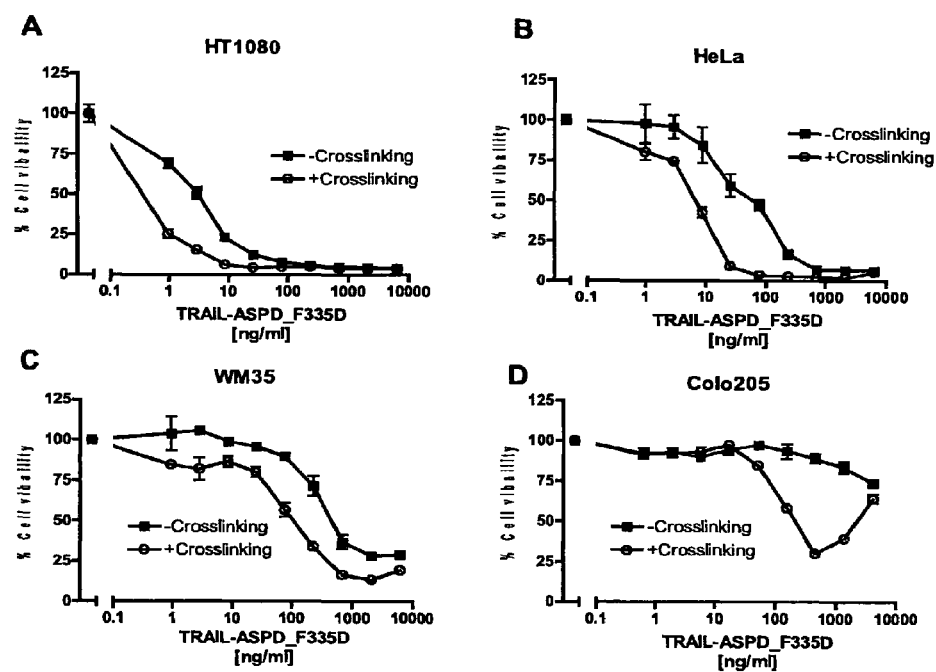
FIG. 29 shows cytotoxic effect TRAIL-SPD_F335D on human cancer cells.

The human cancer cell lines HT1080 (A), HeLa (B), WM35 (C) or Colo205 (D) were incubated over night with varying concentrations of affinity purified, trimeric TRAIL-ASPD_F335D in the presence or absence of cross-linking antibodies (anti-Strep-tag II). Cell viability was quantified by crystal violet staining (HT1080, HeLa and WM35) or MTS (Colo205). The data show that TRAIL-ASPD_F335D is capable of inducing cell death in exemplified cancer cell lines (FIG. 29). The rise of Colo205 cell viability at high concentrations of ligand is likely due to limitation of cross-linking antibody.

2.6 Analysis of Carbohydrate Binding Characteristics of the SPD Trimerization Motif Variants It has been shown that wild-type, full length and oligomeric SP-D protein from several species, as well as the trimeric neck+CRD of human SP-D bind to several different carbohydrates. In addition, the neck+CRD of human SP-D also has been shown to excert immunomodulatory effects by serving as a chemotactic factor for immuno cells such as neutrophils (Cai et al., 1999, *Am J Physiol Lung Cell Mol Physiol* 276:131-136). Other cells may also be recruited by SP-D. The chemotactic effect of neck+CRD of human SP-D has been shown to depend on the glycobinding function, as the addition of maltose inhibited the chemotactic function. Thus, a ligand of the TNFSF with a SP-D-mediated chemotactic function may be of superior activity as compared to ligands or constructs thereof with natural amino acid sequences. For instance, in a scenario where cellular effects are desirable such as in cancer treatment such a described ligand may be desirable.

In addition, a ligand where SP-D has no carbohydrate function may be desirable in other settings. For human SP-D a mutant has been described in which amino acid phenylalanine 335 (corresponding to amino acid 355 of SEQ ID NO:21) has been mutated to alanine (SPD_F335A, Crouch et al., *JBC* 281: 18008-18014). This mutant showed very weak carbohydrate binding. However, introducing a charged amino acid (e.g. an acidic amino acid) may be even better as compared to F335A if no carbohydrate binding is desired. Therefore the mutant SPD_F335D may be superior towards F335A mutant.

Figure 30:
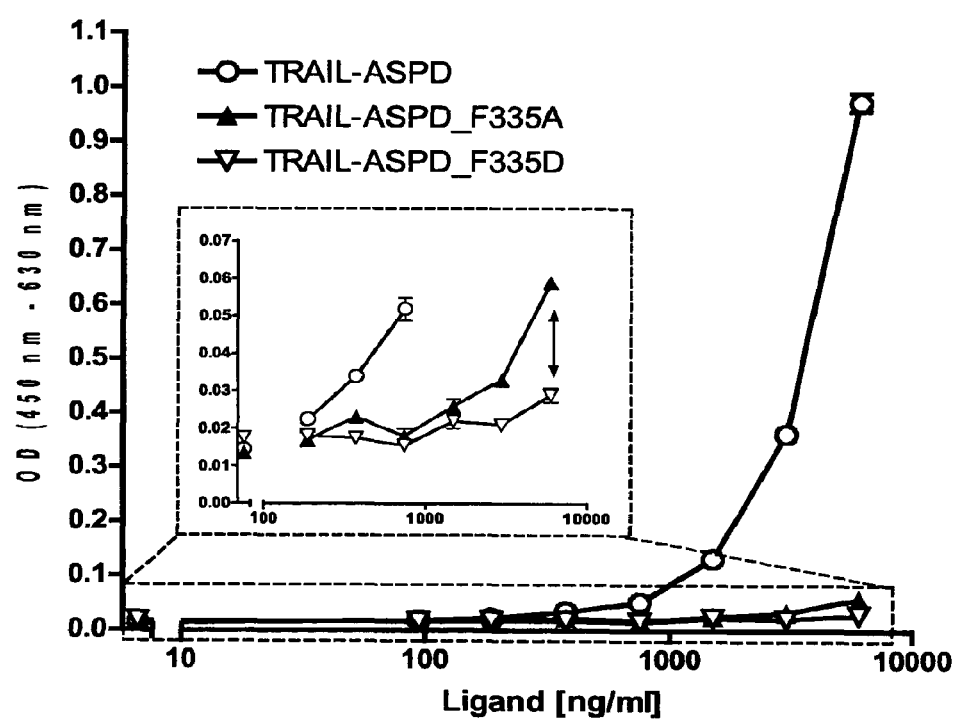
FIG. 30 shows binding of TRAIL-ASPD fusion protein to carbohydrates.
Figure 31:
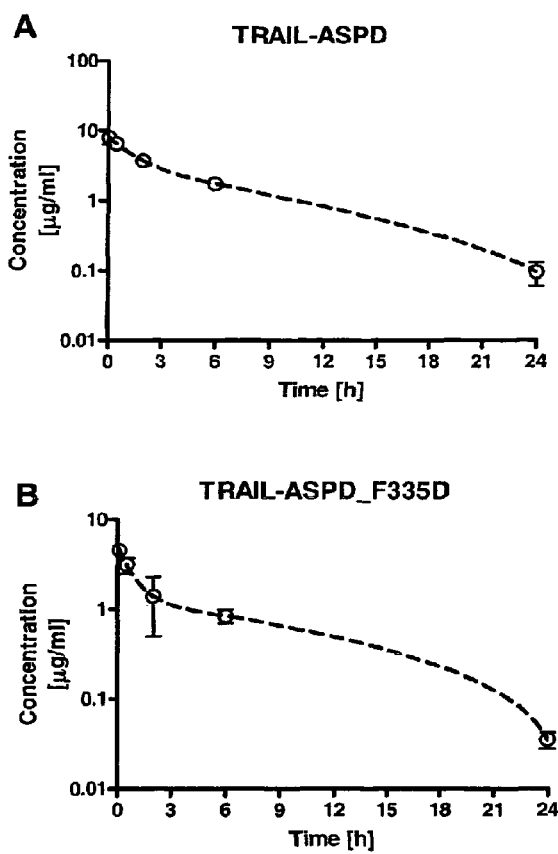
FIG. 31 shows pharmacokinetics of TRAIL-ASPD (A) or TRAIL-ASPD_F335D (B) fusion proteins.
Figure 32:
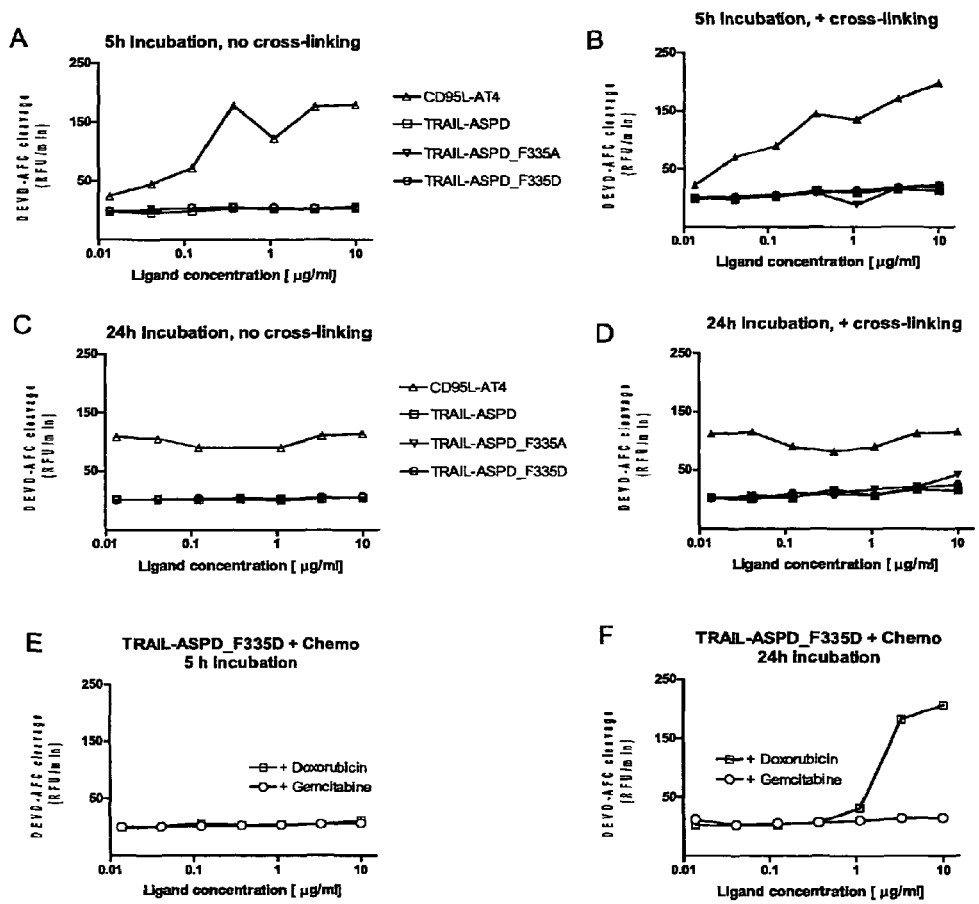
FIG. 32 shows caspase activity in primary human hepatocytes.

To analyze the binding of TRAIL-fusion proteins to carbohydrates, mannan from yeast was immobilized on microplates and the binding of TRAIL-SPD, TRAIL-SPD_F335A or TRAIL-SPD_F335D was detected by ELISA. The results are shown in FIG. 30. As expected, the ELISA signal increased with increasing concentrations of TRAIL-ASPD. In contrast, the carbohydrate-mutant form TRAIL-ASPD_F335A showed a very low ELISA signal. In addition, the new constructed variant TRAIL-ASPD_F335D displayed the lowest ELISA signal (see inset and arrow). This indicated that the mutant F335D has a lower mannan-binding affinity as compared to the previously described SP-D mutant form F335A.

2.7 Pharmacokinetics of TRAIL-SPD Fusion Proteins

To determine the half-lifes of TRAIL-SPD fusion protein, ten micrograms of TRAIL-ASPD (A) or TRAIL-ASPD_F335D (B) were injected intraveneously into male CD1 mice and serum samples were collected after several time points (predose, 5 min., 30 min., 2 h, 6 h and 24 h). TRAIL proteins in sera of mice were quantified by an ELISA and the data was used to calculate halflifes. The results are shown in FIG. 31. For the two proteins analyzed, a halflife of 7 to 14 hours for TRAIL-ASPD (A) and TRAIL-ASPD_F335D (B) were calculated. No animal died or showed signs of intolerance during the period observed. The data indicate an at least 80-fold improvement of the serum halftime as compared to wild type TRAIL that was reported to have a half time in the range of three to five minutes in rodents (Kelley et. al 2001).

2.8 Cytotoxicity of TRAIL-ASPD Fusion Proteins

To analyze potential hepatotoxic effects of TRAIL-ASPD, TRAIL-ASPD_F335A or TRAIL-ASPD_F335D, primary human hepatocytes (PHH) were incubated with varying concentrations of indicated TRAIL-SPD-fusion proteins, with or without cross-linking antibodies (anti-Strep-tag II). As a control, a stabilized variant of CD95L, CD95L-T4 (described in WO2008/025516) was used. The results are shown in FIG. 32.

In addition, the effect of a simultaneous incubation of PHH with 5 mM of chemotherapeutic drugs was analyzed for TRAIL-ASPD_F335D. After 5 h (A, B and E) or 24 h (C, D and F) of incubation, cells were lysed and caspase activity was assessed with a fluorogenic assay.

As a result, all analyzed TRAIL-SPD fusion proteins induced no hepatotoxic effects, even if ligands were secondarily cross-linked by antibodies. In contrast, CD95L-T4 is hepatotoxic as indicated by an increase of active caspase (A to D). Five hours of co-incubation of primary human hepatocytes with trimeric TRAIL-ASPD_F335D together with chemotherapeutic drugs induced no caspase activity (E). However, after 24 h of co-incubation with doxorubicin, soluble TRAIL-ASPD_F335D induced a strong caspase activity signal (F).

This indicates that TRAIL fusion proteins of the present invention may not show undesired hepatotoxicity in medical use. Thus, TRAIL fusion proteins are preferably administered in combination with drugs, which are apoptosis sensitizers and/or apoptosis inducers, e.g. a chemotherapeutic drug such as oxaliplatin, cisplatin, 5-fluorouracil, etoposide, gemcitabine, irinotecan and others, or Bcl2 binding molecules, e.g. small molecules or peptidic compounds, which bind to polypeptides of the Bcl2 family, particularly Bcl2 or Bclxl.

2.9 Characterization of APRIL Fusion Proteins

Figure 33:
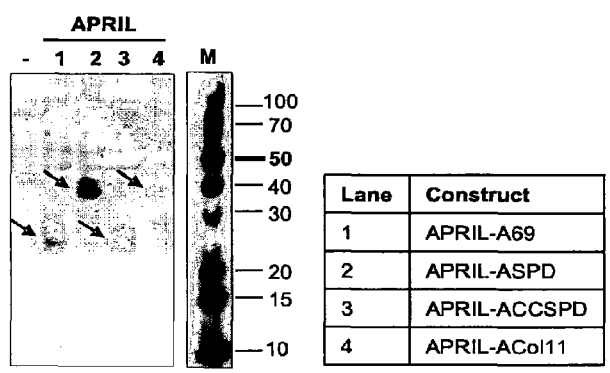
FIG. 33 shows western Blot of supernatants from HEK293 cells transiently transfected with trimerized APRIL constructs.

HEK293 cells were transiently transfected with expression vectors encoding for APRIL-A69 (WO2008025516), APRIL-ASPD, APRIL-ACCSPD or APRIL-ACol11. After three days supernatants were analyzed for secreted proteins by Western Blotting. The results are shown in FIG. 33. For the detection of APRIL-fusion proteins an antibody specific for Strep-tag II was used. Arrows indicate specific bands that were detected around 40 kDa (APRIL-ASPD and APRIL-ACol11, respectively), as well as at around 25 kDa (APRIL-A69 and APRIL-ACCSPD, respectively). Thus APRIL expression cassettes are functional and the secretion of protein indicated that the proteins are properly folded. As for other TNFSF proteins analyzed, the highest secreted protein levels were found for APRIL fused to the trimerization motif composed of coiled coil "neck"+CRD of human SP-D (APRIL-ASPD, lane No. 2). APRIL-ASPD was used to analyze the binding to the receptor TACI.

Figure 34:
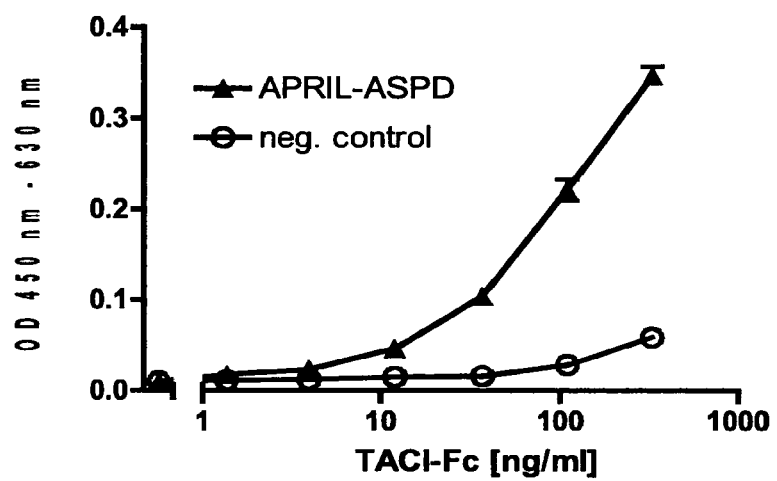
FIG. 34 shows TACI-Fc binds to APRIL-ASPD.

To show that the constructed APRIL-ASPD fusion protein is functional, the binding to a known receptor of APRIL, namely TACI, was assessed (FIG. 34). Therefore, APRIL-ASPD in supernatant from transiently transfected HEK293 cells was immobilized on Streptactin coated microplates. Cell supernatant from untransfected HEK293 cells served as negative control. Specifically bound proteins were detected with varying concentrations of TACI-Fc followed by incubation with an anti-human, Fc-specific antibody conjugated with peroxidase. As a result, the ELISA signal increased with increasing concentrations of TACI-Fc, indicating that APRIL-ASPD is a functional molecule.

The amino acid sequence of an APRIL fusion protein is shown below.

```
SEQ ID 51: Sp-APRIL-ASPD
Total amino acid number: 344, MW = 37120
ORIGIN
    1 METDTLLLWV LLLWVPAGNG KQHSVLHLVP INATSKDDSD VTEVMWQPAL RRGRGLQAQG

61 YGVRIQDAGV YLLYSQVLFQ DVTFTMGQVV SREGQGRQET LFRCIRSMPS HPDRAYNSCY

121 SAGVFHLHQG DILSVIIPRA RAKLNLSPHG TFLGFVKLGS SGSSGSSGSG LPDVASLRQQ

181 VEALQGQVQH LQAAFSQYKK VELFPNGQSV GEKIFKTAGF VKPFTEAQLL CTQAGGQLAS

241 PRSAAENAAL QQLVVAKNEA AFLSMTDSKT EGKFTYPTGE SLVYSNWAPG EPNDDGGSED

301 CVEIFTNGKW NDRACGEKRL VVCEFGGSPS SSSSSAWSHP QFEK 1-20:    Signal secretion peptide (underlined)
21-158:  APRIL-RBD
159-169: Flexible linker element (A-linker; GSS GSS GSS GS italic)
170-207: Coiled coil "neck" region of human SP-D
208-325: C-type lectin domain of human SP-D
326-336: Linker element (GGSPSSSSSSA)
337-344: Strep-tag II (WSHPQFEK)
```

REFERENCES

1. Locksley R M, Killeen N and Lenardo M J (2001) Cell 104: 487-501
2. Bodmer J L, Schneider P and Tschopp J (2002) Trends Biochem. Sci. 27: 19-26
3. Grell M, Douni E, Wajant H, Lohden M., Clauss M, Maxeiner B, Georgopoulos S, Lesslauer W, Kollias G, Pfizenmaier K and Scheurich P (1995) Cell 83: 793-802
4. Schneider P, Holler N, Bodmer J L, Hahne M, Frei K, Fontana A and Tschopp J (1998) J. Exp. Med. 187: 1205-1213
5. Wajant H, Moosmayer D, Wuest T, Bartke T, Gerlach E, Schonherr U, Peters N, Scheurich P and Pfizenmaier K (2001) Oncogene 20: 4101-4106
6. Haswell L E, Glennie M J and Al-Shamkhani A (2001) Eur. J. Immunol. 31:3094-31008
7. Holler N, Tardivel A, Kovacsovics-Bankowski M, Hertig S, Gaide O, Martinon F, Tinel A, Deperthes D, Calderara S, Schulthess T, Engel J, Schneider P and Tschopp J (2003) Mol. Cell. Biol. 23: 1428-1440
8. Stone G W, Barzee S, Snarsky V, Kee K, Spina C A, Yu X F and Kornbluth R S (2006) J. Virol. 80: 1762-177216
9. Mundle S D and Raza A (2002) Trends Immunol. 23: 187-194
10. Siegel R M, Muppidi J R, Sarker M, Lobito A, Jen M, Martin D, Straus S E and Lenardo M J (2004) J. Cell Biol. 167: 735-744
11. Henkler F, Behrle E, Dennehy K M, Wicovsky A, Peters N, Warnke C, Pfizenmaier K and Wajant H (2005) J. Cell Biol. 168: 1087-1098

What is claimed is:

1. A fusion protein comprising:
   (i) TRAIL (tumor necrosis factor-related apoptosis-inducing ligand) or a receptor binding domain thereof, and
   (ii) a collectin trimerization domain comprising a neck domain or a neck and carbohydrate binding domain of surfactant protein-D,
   wherein (ii) is located C-terminally of (i).

2. The fusion protein of claim 1, additionally comprising a flexible linker between (i) and (ii), wherein the flexible linker is a glycine/serine linker and has a length of 3-20 amino acids.

3. The fusion protein of claim 2, wherein the flexible linker element has the amino acid sequence of SEQ ID NO: 53, which is $(GSS)_a(SSG)_b(GSG)_c$ wherein a, b, c is each 0, 1, 2, 3, 4, 5 or 6.

4. The fusion protein of claim 2, wherein the flexible linker element has a length of 9-15 amino acids.

5. The fusion protein of claim 1, wherein the TRAIL has the sequence of SEQ ID NO:10.

6. The fusion protein of claim 1, wherein (i) comprises amino acids 95-281, 116-281, 117-281, 118-281, 119-281 or 120-281 of human TRAIL (SEQ ID NO:10).

7. The fusion protein of claim 1, wherein (i) comprises a mutant of SEQ ID NO:10 or a receptor binding domain thereof, which binds and/or activates TRAIL-receptor 1 and/or TRAIL-receptor 2, wherein the mutant comprises amino acid substitutions only in one or more of the following amino acid positions of SEQ ID NO:10: R130, G160, Y189, R191, Q193, E195, N199, K201, Y213, T214, S215, H264, I266, D267, and D269.

8. The fusion protein of claim 7, wherein the amino acid substitutions are one or more of the following: R130E, G160M, Y189A, Y189Q, R191K, Q193S, Q193R, E195R, N199V, N199R, K201R, Y213W, T214R, S215D, H264R, I266L, D267Q, D269H, D269R, and D269K.

9. The fusion protein of claim 1, wherein (ii) comprises amino acids 217-375, 218-375, 219-375, 220-375, 221-375, 222-375, 223-375, 224-375, or 225-375 of human surfactant protein-D of SEQ ID NO:21.

10. The fusion protein of claim 1, wherein (ii) comprises amino acids 217-257, 218-257, 219-257, 220-257, 221-257, 222-257, 223-257, 224-257, or 225-257 of human surfactant protein-D of SEQ ID NO:21.

11. The fusion protein of claim 1, wherein (ii) comprises a mutant of human surfactant protein-D of SEQ ID NO:21 having only one amino acid substitution.

12. The fusion protein of claim 11, wherein the amino acid substitution is one of the following: F355A, F355S, F355T, F355E, F355D, F355K, or F355R.

13. The fusion protein of claim 11, wherein (ii) comprises a mutant which does not bind to mannose.

14. The fusion protein of claim 1, which additionally comprises an N-terminal signal peptide domain.

15. The fusion protein of claim 1, which comprises the sequence of SEQ ID NO: 43 or 44.

16. The fusion protein of claim 1, wherein the fusion protein further comprises a recognition/purification domain located at the N-terminus or at the C-terminus.

17. The fusion protein of claim 16, wherein the recognition/purification domain is a Strep-tag or a poly His-domain.

18. The fusion protein of claim 1, which additionally comprises a terminal flexible element.

19. A trimeric complex comprising three fusion proteins of claim 1.

20. The trimeric complex of claim 19, wherein the complex is formed by covalent linkage between the three fusion proteins.

21. The trimeric complex of claim 19, wherein the complex consists of three identical fusion proteins.

22. A nucleic acid molecule encoding the fusion protein of claim 1.

23. The nucleic acid molecule of claim 22, which is operatively linked to an expression control sequence.

24. A vector comprising the nucleic acid molecule of claim 23.

25. An isolated cell transformed or transfected with the nucleic acid molecule of claim 23.

* * * * *

SEQUENCE LISTING

<160> NUMBER OF SEQ ID NOS: 62

<210> SEQ ID NO 1
<211> LENGTH: 205
<212> TYPE: PRT
<213> ORGANISM: Homo sapiens
<220> FEATURE:
<221> NAME/KEY: MISC_FEATURE
<223> OTHER INFORMATION: human LTA

<400> SEQUENCE: 1

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

<210> SEQ ID NO 2
<211> LENGTH: 233
<212> TYPE: PRT
<213> ORGANISM: Homo sapiens
<220> FEATURE:
<221> NAME/KEY: MISC_FEATURE
<223> OTHER INFORMATION: human TNFa

<400> SEQUENCE: 2

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro

```
                        85                  90                  95
Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
        130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 3
<211> LENGTH: 244
<212> TYPE: PRT
<213> ORGANISM: Homo sapiens
<220> FEATURE:
<221> NAME/KEY: MISC_FEATURE
<223> OTHER INFORMATION: human LTA
<220> FEATURE:
<221> NAME/KEY: MISC_FEATURE
<223> OTHER INFORMATION: human LTB

<400> SEQUENCE: 3

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190
```

```
Arg Arg Gln Gly Tyr Gly Pro Leu Trp Tyr Thr Ser Val Gly Phe Gly
            195                 200                 205

Gly Leu Val Gln Leu Arg Arg Gly Glu Arg Val Tyr Val Asn Ile Ser
210                 215                 220

His Pro Asp Met Val Asp Phe Ala Arg Gly Lys Thr Phe Phe Gly Ala
225                 230                 235                 240

Val Met Val Gly

<210> SEQ ID NO 4
<211> LENGTH: 183
<212> TYPE: PRT
<213> ORGANISM: Homo sapiens
<220> FEATURE:
<221> NAME/KEY: MISC_FEATURE
<223> OTHER INFORMATION: human OX40L

<400> SEQUENCE: 4

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 261
<212> TYPE: PRT
<213> ORGANISM: Homo sapiens
<220> FEATURE:
<221> NAME/KEY: MISC_FEATURE
<223> OTHER INFORMATION: human CD40L

<400> SEQUENCE: 5

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
```

```
              50                  55                  60
Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 6
<211> LENGTH: 281
<212> TYPE: PRT
<213> ORGANISM: Homo sapiens
<220> FEATURE:
<221> NAME/KEY: MISC_FEATURE
<223> OTHER INFORMATION: human CD95L

<400> SEQUENCE: 6

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
                 20                  25                  30

Pro Thr Ser Val Pro Arg Arg Pro Gly Gln Arg Arg Pro Pro Pro Pro
             35                  40                  45

Pro Pro Pro Pro Pro Leu Pro Pro Pro Pro Pro Pro Pro Pro Leu Pro
         50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140
```

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 7
<211> LENGTH: 193
<212> TYPE: PRT
<213> ORGANISM: Homo sapiens
<220> FEATURE:
<221> NAME/KEY: MISC_FEATURE
<223> OTHER INFORMATION: human CD27L

<400> SEQUENCE: 7

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro

<210> SEQ ID NO 8
<211> LENGTH: 234

```
<212> TYPE: PRT
<213> ORGANISM: Homo sapiens
<220> FEATURE:
<221> NAME/KEY: MISC_FEATURE
<223> OTHER INFORMATION: human CD30L

<400> SEQUENCE: 8
```

Met Asp Pro Gly Leu Gln Gln Ala Leu Asn Gly Met Ala Pro Pro Gly
 1               5                  10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
 50                  55                  60

Thr Asp Ser Ile Pro Asn Ser Pro Asp Asn Val Pro Leu Lys Gly Gly
 65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
210                 215                 220

Leu Ser Ile Phe Leu Tyr Ser Asn Ser Asp
225                 230

```
<210> SEQ ID NO 9
<211> LENGTH: 254
<212> TYPE: PRT
<213> ORGANISM: Homo sapiens
<220> FEATURE:
<221> NAME/KEY: MISC_FEATURE
<223> OTHER INFORMATION: human CD137L

<400> SEQUENCE: 9
```

Met Glu Tyr Ala Ser Asp Ala Ser Leu Asp Pro Glu Ala Pro Trp Pro
 1               5                  10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
 50                  55                  60

Ala Ala Ser Pro Arg Leu Arg Glu Gly Pro Glu Leu Ser Pro Asp Asp
 65                  70                  75                  80

```
Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 10
<211> LENGTH: 281
<212> TYPE: PRT
<213> ORGANISM: Homo sapiens
<220> FEATURE:
<221> NAME/KEY: MISC_FEATURE
<223> OTHER INFORMATION: human TRAIL

<400> SEQUENCE: 10

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190
```

```
Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
                275                 280

<210> SEQ ID NO 11
<211> LENGTH: 317
<212> TYPE: PRT
<213> ORGANISM: Homo sapiens
<220> FEATURE:
<221> NAME/KEY: MISC_FEATURE
<223> OTHER INFORMATION: human RANKL

<400> SEQUENCE: 11

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
                20                  25                  30

Pro Pro Pro Pro Ala Pro His Gln Pro Pro Ala Ala Ser Arg Ser Met
            35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
```

```
                    260                 265                 270
Tyr Ser Ile Asn Val Gly Gly Phe Phe Lys Leu Arg Ser Gly Glu Glu
                275                 280                 285

Ile Ser Ile Glu Val Ser Asn Pro Ser Leu Leu Asp Pro Asp Gln Asp
                290                 295                 300

Ala Thr Tyr Phe Gly Ala Phe Lys Val Arg Asp Ile Asp
305                 310                 315

<210> SEQ ID NO 12
<211> LENGTH: 249
<212> TYPE: PRT
<213> ORGANISM: Homo sapiens
<220> FEATURE:
<221> NAME/KEY: MISC_FEATURE
<223> OTHER INFORMATION: human TWEAK

<400> SEQUENCE: 12

Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
                35                  40                  45

Ser Leu Ser Ala Gln Glu Pro Ala Gln Glu Glu Leu Val Ala Glu Glu
            50                  55                  60

Asp Gln Asp Pro Ser Glu Leu Asn Pro Gln Thr Glu Glu Ser Gln Asp
65              70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
                100                 105                 110

Val His Pro Arg Pro Gly Gln Asp Gly Ala Gln Ala Gly Val Asp Gly
            115                 120                 125

Thr Val Ser Gly Trp Glu Glu Ala Arg Ile Asn Ser Ser Ser Pro Leu
            130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
            210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 13
<211> LENGTH: 247
<212> TYPE: PRT
<213> ORGANISM: Homo sapiens
<220> FEATURE:
<221> NAME/KEY: MISC_FEATURE
<223> OTHER INFORMATION: human APRIL_ver1
```

-continued

<400> SEQUENCE: 13

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Leu
                245
```

<210> SEQ ID NO 14
<211> LENGTH: 250
<212> TYPE: PRT
<213> ORGANISM: Homo sapiens
<220> FEATURE:
<221> NAME/KEY: MISC_FEATURE
<223> OTHER INFORMATION: human APRIL_ver2

<400> SEQUENCE: 14

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95
```

```
Gly Glu Arg Ser Arg Lys Arg Arg Ala Val Leu Thr Gln Lys Gln Lys
                100                 105                 110

Lys Gln His Ser Val Leu His Leu Val Pro Ile Asn Ala Thr Ser Lys
            115                 120                 125

Asp Asp Ser Asp Val Thr Glu Val Met Trp Gln Pro Ala Leu Arg Arg
        130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 15
<211> LENGTH: 285
<212> TYPE: PRT
<213> ORGANISM: Homo sapiens
<220> FEATURE:
<221> NAME/KEY: MISC_FEATURE
<223> OTHER INFORMATION: human BAFF

<400> SEQUENCE: 15

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205
```

Gly His Leu Ile Gln Arg Lys Lys Val His Val Phe Gly Asp Glu Leu
210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
                260                 265                 270

Asp Gly Asp Val Thr Phe Phe Gly Ala Leu Lys Leu Leu
                275                 280                 285

<210> SEQ ID NO 16
<211> LENGTH: 240
<212> TYPE: PRT
<213> ORGANISM: Homo sapiens
<220> FEATURE:
<221> NAME/KEY: MISC_FEATURE
<223> OTHER INFORMATION: human LIGHT

<400> SEQUENCE: 16

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
                20                  25                  30

Cys Ser Val Ala Arg Val Gly Leu Gly Leu Leu Leu Leu Leu Met Gly
            35                  40                  45

Ala Gly Leu Ala Val Gln Gly Trp Phe Leu Leu Gln Leu His Trp Arg
50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
210                 215                 220

Val Arg Leu Arg Asp Gly Thr Arg Ser Tyr Phe Gly Ala Phe Met Val
225                 230                 235                 240

<210> SEQ ID NO 17
<211> LENGTH: 251
<212> TYPE: PRT
<213> ORGANISM: Homo sapiens
<220> FEATURE:
<221> NAME/KEY: MISC_FEATURE
<223> OTHER INFORMATION: human TL1A

<400> SEQUENCE: 17

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 18
<211> LENGTH: 177
<212> TYPE: PRT
<213> ORGANISM: Homo sapiens
<220> FEATURE:
<221> NAME/KEY: MISC_FEATURE
<223> OTHER INFORMATION: human GITRL

<400> SEQUENCE: 18

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
        35                  40                  45

Leu Gln Leu Glu Thr Ala Lys Glu Pro Cys Met Ala Lys Phe Gly Pro
50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu

```
                        85                  90                  95
Ile Tyr Gly Gln Val Ala Pro Asn Ala Asn Tyr Asn Asp Val Ala Pro
            100                 105                 110

Phe Glu Val Arg Leu Tyr Lys Asn Lys Asp Met Ile Gln Thr Leu Thr
            115                 120                 125

Asn Lys Ser Lys Ile Gln Asn Val Gly Gly Thr Tyr Glu Leu His Val
            130                 135                 140

Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser

<210> SEQ ID NO 19
<211> LENGTH: 391
<212> TYPE: PRT
<213> ORGANISM: Homo sapiens
<220> FEATURE:
<221> NAME/KEY: MISC_FEATURE
<223> OTHER INFORMATION: human EDA-A1

<400> SEQUENCE: 19

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
            115                 120                 125

Asp Gly His Gln Met Ala Leu Leu Asn Phe Phe Phe Pro Asp Glu Lys
        130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
            195                 200                 205

Pro Gly Thr Thr Val Met Gly Pro Pro Gly Pro Pro Gly Pro Pro Gly
        210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
```

```
              260                 265                 270
Asp Trp Ser Arg Ile Thr Met Asn Pro Lys Val Phe Lys Leu His Pro
            275                 280                 285

Arg Ser Gly Glu Leu Glu Val Leu Val Asp Gly Thr Tyr Phe Ile Tyr
        290                 295                 300

Ser Gln Val Glu Val Tyr Tyr Ile Asn Phe Thr Asp Phe Ala Ser Tyr
305                 310                 315                 320

Glu Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Thr Phe Phe Gly Ala Ile Arg
    370                 375                 380

Leu Gly Glu Ala Pro Ala Ser
385                 390

<210> SEQ ID NO 20
<211> LENGTH: 389
<212> TYPE: PRT
<213> ORGANISM: Homo sapiens
<220> FEATURE:
<221> NAME/KEY: MISC_FEATURE
<223> OTHER INFORMATION: human EDA-A2

<400> SEQUENCE: 20

Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Phe Pro Asp Glu Lys
    130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220
```

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
            245                 250                 255

Gly Ser Ala Ile Gln Val Lys Asn Asp Leu Ser Gly Gly Val Leu Asn
                260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Tyr Tyr Ile Asn Phe Thr Asp Phe Ala Ser Tyr Glu Val
305                 310                 315                 320

Val Val Asp Glu Lys Pro Phe Leu Gln Cys Thr Arg Ser Ile Glu Thr
                325                 330                 335

Gly Lys Thr Asn Tyr Asn Thr Cys Tyr Thr Ala Gly Val Cys Leu Leu
                340                 345                 350

Lys Ala Arg Gln Lys Ile Ala Val Lys Met Val His Ala Asp Ile Ser
            355                 360                 365

Ile Asn Met Ser Lys His Thr Thr Phe Phe Gly Ala Ile Arg Leu Gly
370                 375                 380

Glu Ala Pro Ala Ser
385

<210> SEQ ID NO 21
<211> LENGTH: 375
<212> TYPE: PRT
<213> ORGANISM: Homo sapiens

<400> SEQUENCE: 21

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Thr Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Ala Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

-continued

```
Ile Pro Gly Asp Lys Gly Ala Lys Gly Glu Ser Gly Leu Pro Asp Val
    210                 215                 220
Ala Ser Leu Arg Gln Gln Val Glu Ala Leu Gln Gly Gln Val Gln His
225                 230                 235                 240
Leu Gln Ala Ala Phe Ser Gln Tyr Lys Lys Val Glu Leu Phe Pro Asn
                245                 250                 255
Gly Gln Ser Val Gly Glu Lys Ile Phe Lys Thr Ala Gly Phe Val Lys
                260                 265                 270
Pro Phe Thr Glu Ala Gln Leu Leu Cys Thr Gln Ala Gly Gly Gln Leu
            275                 280                 285
Ala Ser Pro Arg Ser Ala Glu Asn Ala Ala Leu Gln Gln Leu Val
290                 295                 300
Val Ala Lys Asn Glu Ala Ala Phe Leu Ser Met Thr Asp Ser Lys Thr
305                 310                 315                 320
Glu Gly Lys Phe Thr Tyr Pro Thr Gly Glu Ser Leu Val Tyr Ser Asn
                325                 330                 335
Trp Ala Pro Gly Glu Pro Asn Asp Asp Gly Ser Glu Asp Cys Val
                340                 345                 350
Glu Ile Phe Thr Asn Gly Lys Trp Asn Asp Arg Ala Cys Gly Glu Lys
            355                 360                 365
Arg Leu Val Val Cys Glu Phe
    370                 375

<210> SEQ ID NO 22
<211> LENGTH: 271
<212> TYPE: PRT
<213> ORGANISM: Homo sapiens

<400> SEQUENCE: 22

Met Arg Gly Asn Leu Ala Leu Val Gly Val Leu Ile Ser Leu Ala Phe
1               5                   10                  15
Leu Ser Leu Leu Pro Ser Gly His Pro Gln Pro Ala Gly Asp Asp Ala
                20                  25                  30
Cys Ser Val Gln Ile Leu Val Pro Gly Leu Lys Gly Asp Ala Gly Glu
            35                  40                  45
Lys Gly Asp Lys Gly Ala Pro Gly Arg Pro Gly Arg Val Gly Pro Thr
    50                  55                  60
Gly Glu Lys Gly Asp Met Gly Asp Lys Gly Gln Lys Gly Ser Val Gly
65                  70                  75                  80
Arg His Gly Lys Ile Gly Pro Ile Gly Ser Lys Gly Glu Lys Gly Asp
                85                  90                  95
Ser Gly Asp Ile Gly Pro Pro Gly Pro Asn Gly Glu Pro Gly Leu Pro
            100                 105                 110
Cys Glu Cys Ser Gln Leu Arg Lys Ala Ile Gly Glu Met Asp Asn Gln
        115                 120                 125
Val Ser Gln Leu Thr Ser Glu Leu Lys Phe Ile Lys Asn Ala Val Ala
    130                 135                 140
Gly Val Arg Glu Thr Glu Ser Lys Ile Tyr Leu Leu Val Lys Glu Glu
145                 150                 155                 160
Lys Arg Tyr Ala Asp Ala Gln Leu Ser Cys Gln Gly Arg Gly Gly Thr
                165                 170                 175
Leu Ser Met Pro Lys Asp Glu Ala Ala Asn Gly Leu Met Ala Ala Tyr
            180                 185                 190
Leu Ala Gln Ala Gly Leu Ala Arg Val Phe Ile Gly Ile Asn Asp Leu
```

```
                195                 200                 205
Glu Lys Glu Gly Ala Phe Val Tyr Ser Asp His Ser Pro Met Arg Thr
            210                 215                 220

Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
                245                 250                 255

His Thr Thr Met Tyr Phe Met Cys Glu Phe Asp Lys Gly Asn Met
            260                 265                 270

<210> SEQ ID NO 23
<211> LENGTH: 19
<212> TYPE: PRT
<213> ORGANISM: Artificial
<220> FEATURE:
<223> OTHER INFORMATION: signal peptide

<400> SEQUENCE: 23

Met Asn Phe Gly Phe Ser Leu Ile Phe Leu Val Leu Val Leu Lys Gly
1               5                   10                  15

Val Gln Cys

<210> SEQ ID NO 24
<211> LENGTH: 20
<212> TYPE: PRT
<213> ORGANISM: Artificial
<220> FEATURE:
<223> OTHER INFORMATION: signal peptide

<400> SEQUENCE: 24

Met Glu Thr Asp Thr Leu Leu Leu Trp Val Leu Leu Leu Trp Val Pro
1               5                   10                  15

Gly Ser Thr Gly
            20

<210> SEQ ID NO 25
<211> LENGTH: 20
<212> TYPE: PRT
<213> ORGANISM: Artificial
<220> FEATURE:
<223> OTHER INFORMATION: signal peptide

<400> SEQUENCE: 25

Met Glu Thr Asp Thr Leu Leu Leu Trp Val Leu Leu Leu Trp Val Pro
1               5                   10                  15

Ala Gly Asn Gly
            20

<210> SEQ ID NO 26
<211> LENGTH: 339
<212> TYPE: PRT
<213> ORGANISM: Artificial
<220> FEATURE:
<223> OTHER INFORMATION: fusion protein SP-hsTrailsyn-SPD-construct-1

<400> SEQUENCE: 26

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45
```

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                    85                  90                  95

Ile Lys Glu Asn Thr Lys Asn Asp Lys Gln Met Val Gln Tyr Ile Tyr
                100                 105                 110

Lys Tyr Thr Ser Tyr Pro Asp Pro Ile Leu Leu Met Lys Ser Ala Arg
            115                 120                 125

Asn Ser Cys Trp Ser Lys Asp Ala Glu Tyr Gly Leu Tyr Ser Ile Tyr
        130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Gly Leu Pro Asp Val Ala Ser Leu Arg
                180                 185                 190

Gln Gln Val Glu Ala Leu Gln Gly Gln Val Gln His Leu Gln Ala Ala
            195                 200                 205

Phe Ser Gln Tyr Lys Lys Val Glu Leu Phe Pro Asn Gly Gln Ser Val
        210                 215                 220

Gly Glu Lys Ile Phe Lys Thr Ala Gly Phe Val Lys Pro Phe Thr Glu
225                 230                 235                 240

Ala Gln Leu Leu Cys Thr Gln Ala Gly Gly Gln Leu Ala Ser Pro Arg
                245                 250                 255

Ser Ala Ala Glu Asn Ala Ala Leu Gln Gln Leu Val Val Ala Lys Asn
                260                 265                 270

Glu Ala Ala Phe Leu Ser Met Thr Asp Ser Lys Thr Glu Gly Lys Phe
            275                 280                 285

Thr Tyr Pro Thr Gly Glu Ser Leu Val Tyr Ser Asn Trp Ala Pro Gly
        290                 295                 300

Glu Pro Asn Asp Asp Gly Gly Ser Glu Asp Cys Val Glu Ile Phe Thr
305                 310                 315                 320

Asn Gly Lys Trp Asn Asp Arg Ala Cys Gly Glu Lys Arg Leu Val Val
                325                 330                 335

Cys Glu Phe

<210> SEQ ID NO 27
<211> LENGTH: 343
<212> TYPE: PRT
<213> ORGANISM: Artificial
<220> FEATURE:
<223> OTHER INFORMATION: fusion protein SP-hsTrailsyn-SPD-construct-2

<400> SEQUENCE: 27

Met Glu Thr Asp Thr Leu Leu Leu Trp Val Leu Leu Leu Trp Val Pro
1               5                   10                  15

Gly Ser Thr Gly Glu Arg Gly Pro Gln Arg Val Ala Ala His Ile Thr
                20                  25                  30

Gly Thr Arg Gly Arg Ser Asn Thr Leu Ser Ser Pro Asn Ser Lys Asn
            35                  40                  45

Glu Lys Ala Leu Gly Arg Lys Ile Asn Ser Trp Glu Ser Ser Arg Ser
        50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
            115                 120                 125

Lys Ser Ala Arg Asn Ser Cys Trp Ser Lys Asp Ala Glu Tyr Gly Leu
        130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gly Leu Pro Asp Val
            180                 185                 190

Ala Ser Leu Arg Gln Gln Val Glu Ala Leu Gln Gly Gln Val Gln His
        195                 200                 205

Leu Gln Ala Ala Phe Ser Gln Tyr Lys Lys Val Glu Leu Phe Pro Asn
210                 215                 220

Gly Gln Ser Val Gly Glu Lys Ile Phe Lys Thr Ala Gly Phe Val Lys
225                 230                 235                 240

Pro Phe Thr Glu Ala Gln Leu Leu Cys Thr Gln Ala Gly Gly Gln Leu
                245                 250                 255

Ala Ser Pro Arg Ser Ala Ala Glu Asn Ala Ala Leu Gln Gln Leu Val
            260                 265                 270

Val Ala Lys Asn Glu Ala Ala Phe Leu Ser Met Thr Asp Ser Lys Thr
        275                 280                 285

Glu Gly Lys Phe Thr Tyr Pro Thr Gly Glu Ser Leu Val Tyr Ser Asn
290                 295                 300

Trp Ala Pro Gly Glu Pro Asn Asp Asp Gly Ser Glu Asp Cys Val
305                 310                 315                 320

Glu Ile Phe Thr Asn Gly Lys Trp Asn Asp Arg Ala Cys Gly Glu Lys
                325                 330                 335

Arg Leu Val Val Cys Glu Phe
            340

<210> SEQ ID NO 28
<211> LENGTH: 225
<212> TYPE: PRT
<213> ORGANISM: Artificial
<220> FEATURE:
<223> OTHER INFORMATION: fusion protein

<400> SEQUENCE: 28

Met Glu Thr Asp Thr Leu Leu Leu Trp Val Leu Leu Leu Trp Val Pro
1               5                   10                  15

Gly Ser Thr Gly Glu Arg Gly Pro Gln Arg Val Ala Ala His Ile Thr
                20                  25                  30

Gly Thr Arg Gly Arg Ser Asn Thr Leu Ser Ser Pro Asn Ser Lys Asn
            35                  40                  45

Glu Lys Ala Leu Gly Arg Lys Ile Asn Ser Trp Glu Ser Ser Arg Ser
        50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
            115                 120                 125

Lys Ser Ala Arg Asn Ser Cys Trp Ser Lys Asp Ala Glu Tyr Gly Leu
130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gly Leu Pro Asp Val
                180                 185                 190

Ala Ser Leu Arg Gln Gln Val Glu Ala Leu Gln Gly Gln Val Gln His
            195                 200                 205

Leu Gln Ala Ala Phe Ser Gln Tyr Lys Lys Val Glu Leu Phe Pro Asn
        210                 215                 220

Gly
225

<210> SEQ ID NO 29
<211> LENGTH: 338
<212> TYPE: PRT
<213> ORGANISM: Artificial
<220> FEATURE:
<223> OTHER INFORMATION: fusion protein SP-hsTrailsyn-coll11-construct-1

<400> SEQUENCE: 29

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Gln Leu Arg Lys Ala Ile Gly Glu Met
            180                 185                 190

Asp Asn Gln Val Ser Gln Leu Thr Ser Glu Leu Lys Phe Ile Lys Asn
        195                 200                 205

```
Ala Val Ala Gly Val Arg Glu Thr Glu Ser Lys Ile Tyr Leu Leu Val
    210                 215                 220

Lys Glu Glu Lys Arg Tyr Ala Asp Ala Gln Leu Ser Cys Gln Gly Arg
225                 230                 235                 240

Gly Gly Thr Leu Ser Met Pro Lys Asp Glu Ala Ala Asn Gly Leu Met
                245                 250                 255

Ala Ala Tyr Leu Ala Gln Ala Gly Leu Ala Arg Val Phe Ile Gly Ile
            260                 265                 270

Asn Asp Leu Glu Lys Glu Gly Ala Phe Val Tyr Ser Asp His Ser Pro
        275                 280                 285

Met Arg Thr Phe Asn Lys Trp Arg Ser Gly Glu Pro Asn Asn Ala Tyr
290                 295                 300

Asp Glu Glu Asp Cys Val Glu Met Val Ala Ser Gly Gly Trp Asn Asp
305                 310                 315                 320

Val Ala Cys His Thr Thr Met Tyr Phe Met Cys Glu Phe Asp Lys Glu
                325                 330                 335

Asn Met
```

<210> SEQ ID NO 30
<211> LENGTH: 342
<212> TYPE: PRT
<213> ORGANISM: Artificial
<220> FEATURE:
<223> OTHER INFORMATION: fusion protein SP-hsTrailsyn-coll11-construct-2

<400> SEQUENCE: 30

```
Met Glu Thr Asp Thr Leu Leu Trp Val Leu Leu Leu Trp Val Pro
1               5                   10                  15

Gly Ser Thr Gly Glu Arg Gly Pro Gln Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gln Leu Arg Lys Ala
            180                 185                 190

Ile Gly Glu Met Asp Asn Gln Val Ser Gln Leu Thr Ser Glu Leu Lys
        195                 200                 205

Phe Ile Lys Asn Ala Val Ala Gly Val Arg Glu Thr Glu Ser Lys Ile
    210                 215                 220

Tyr Leu Leu Val Lys Glu Glu Lys Arg Tyr Ala Asp Ala Gln Leu Ser
```

225                 230                 235                 240

Cys Gln Gly Arg Gly Gly Thr Leu Ser Met Pro Lys Asp Glu Ala Ala
                        245                 250                 255

Asn Gly Leu Met Ala Ala Tyr Leu Ala Gln Ala Gly Leu Ala Arg Val
                260                 265                 270

Phe Ile Gly Ile Asn Asp Leu Glu Lys Glu Gly Ala Phe Val Tyr Ser
            275                 280                 285

Asp His Ser Pro Met Arg Thr Phe Asn Lys Trp Arg Ser Gly Glu Pro
        290                 295                 300

Asn Asn Ala Tyr Asp Glu Glu Asp Cys Val Glu Met Val Ala Ser Gly
305                 310                 315                 320

Gly Trp Asn Asp Val Ala Cys His Thr Thr Met Tyr Phe Met Cys Glu
                325                 330                 335

Phe Asp Lys Glu Asn Met
            340

<210> SEQ ID NO 31
<211> LENGTH: 222
<212> TYPE: PRT
<213> ORGANISM: Artificial
<220> FEATURE:
<223> OTHER INFORMATION: fusion protein SP-hsTrailsyn-coll11-construct-3

<400> SEQUENCE: 31

Met Glu Thr Asp Thr Leu Leu Leu Trp Val Leu Leu Leu Trp Val Pro
1               5                   10                  15

Gly Ser Thr Gly Glu Arg Gly Pro Gln Arg Val Ala Ala His Ile Thr
            20                  25                  30

Gly Thr Arg Gly Arg Ser Asn Thr Leu Ser Ser Pro Asn Ser Lys Asn
        35                  40                  45

Glu Lys Ala Leu Gly Arg Lys Ile Asn Ser Trp Glu Ser Ser Arg Ser
    50                  55                  60

Gly His Ser Phe Leu Ser Asn Leu His Leu Arg Asn Gly Glu Leu Val
65                  70                  75                  80

Ile His Glu Lys Gly Phe Tyr Tyr Ile Tyr Ser Gln Thr Tyr Phe Arg
                85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
        115                 120                 125

Lys Ser Ala Arg Asn Ser Cys Trp Ser Lys Asp Ala Glu Tyr Gly Leu
    130                 135                 140

Tyr Ser Ile Tyr Gln Gly Gly Ile Phe Glu Leu Lys Glu Asn Asp Arg
145                 150                 155                 160

Ile Phe Val Ser Val Thr Asn Glu His Leu Ile Asp Met Asp His Glu
                165                 170                 175

Ala Ser Phe Phe Gly Ala Phe Leu Val Gly Ser Gln Leu Arg Lys Ala
            180                 185                 190

Ile Gly Glu Met Asp Asn Gln Val Ser Gln Leu Thr Ser Glu Leu Lys
        195                 200                 205

Phe Ile Lys Asn Ala Val Ala Gly Val Arg Glu Thr Glu Ser
    210                 215                 220

<210> SEQ ID NO 32
<211> LENGTH: 235
<212> TYPE: PRT

<213> ORGANISM: Artificial
<220> FEATURE:
<223> OTHER INFORMATION: fusion protein FLAG-hCol11-hTRAIL_Glu116_Gly281

<400> SEQUENCE: 32

Met Asn Phe Gly Phe Ser Leu Ile Phe Leu Val Leu Val Leu Lys Gly
1               5                   10                  15

Val Gln Cys Asp Tyr Lys Asp Asp Asp Lys Gly Leu Pro Cys Glu
            20                  25                  30

Cys Ser Gln Leu Arg Lys Ala Ile Gly Glu Met Asp Asn Gln Val Ser
        35                  40                  45

Gln Leu Thr Ser Glu Leu Lys Phe Ile Lys Asn Ala Val Ala Gly Val
50                  55                  60

Arg Glu Thr Glu Ser Glu Arg Gly Pro Gln Arg Val Ala Ala His Ile
65                  70                  75                  80

Thr Gly Thr Arg Gly Arg Ser Asn Thr Leu Ser Ser Pro Asn Ser Lys
                85                  90                  95

Asn Glu Lys Ala Leu Gly Arg Lys Ile Asn Ser Trp Glu Ser Ser Arg
            100                 105                 110

Ser Gly His Ser Phe Leu Ser Asn Leu His Leu Arg Asn Gly Glu Leu
        115                 120                 125

Val Ile His Glu Lys Gly Phe Tyr Tyr Ile Tyr Ser Gln Thr Tyr Phe
130                 135                 140

Arg Phe Gln Glu Glu Ile Lys Glu Asn Thr Lys Asn Asp Lys Gln Met
145                 150                 155                 160

Val Gln Tyr Ile Tyr Lys Tyr Thr Ser Tyr Pro Asp Pro Ile Leu Leu
                165                 170                 175

Met Lys Ser Ala Arg Asn Ser Cys Trp Ser Lys Asp Ala Glu Tyr Gly
            180                 185                 190

Leu Tyr Ser Ile Tyr Gln Gly Gly Ile Phe Glu Leu Lys Glu Asn Asp
        195                 200                 205

Arg Ile Phe Val Ser Val Thr Asn Glu His Leu Ile Asp Met Asp His
    210                 215                 220

Glu Ala Ser Phe Phe Gly Ala Phe Leu Val Gly
225                 230                 235

<210> SEQ ID NO 33
<211> LENGTH: 233
<212> TYPE: PRT
<213> ORGANISM: Artificial
<220> FEATURE:
<223> OTHER INFORMATION: fusion protein
      FLAG-hCol11s-hTRAIL_Glu116_Gly281

<400> SEQUENCE: 33

Met Asn Phe Gly Phe Ser Leu Ile Phe Leu Val Leu Val Leu Lys Gly
1               5                   10                  15

Val Gln Cys Asp Tyr Lys Asp Asp Asp Lys Gly Leu Pro Cys Glu
            20                  25                  30

Cys Ser Gln Leu Arg Lys Ala Ile Gly Glu Met Asp Asn Gln Val Ser
        35                  40                  45

Gln Leu Thr Ser Glu Leu Lys Phe Ile Lys Asn Ala Val Ala Gly Val
50                  55                  60

Arg Glu Thr Glu Arg Gly Pro Gln Arg Val Ala Ala His Ile Thr Gly
65                  70                  75                  80

Thr Arg Gly Arg Ser Asn Thr Leu Ser Ser Pro Asn Ser Lys Asn Glu
                85                  90                  95

```
Lys Ala Leu Gly Arg Lys Ile Asn Ser Trp Glu Ser Ser Arg Ser Gly
            100                 105                 110

His Ser Phe Leu Ser Asn Leu His Leu Arg Asn Gly Glu Leu Val Ile
            115                 120                 125

His Glu Lys Gly Phe Tyr Tyr Ile Tyr Ser Gln Thr Tyr Phe Arg Phe
            130                 135                 140

Gln Glu Glu Ile Lys Glu Asn Thr Lys Asn Asp Lys Gln Met Val Gln
145                 150                 155                 160

Tyr Ile Tyr Lys Tyr Thr Ser Tyr Pro Asp Pro Ile Leu Leu Met Lys
                165                 170                 175

Ser Ala Arg Asn Ser Cys Trp Ser Lys Asp Ala Glu Tyr Gly Leu Tyr
            180                 185                 190

Ser Ile Tyr Gln Gly Gly Ile Phe Glu Leu Lys Glu Asn Asp Arg Ile
            195                 200                 205

Phe Val Ser Val Thr Asn Glu His Leu Ile Asp Met Asp His Glu Ala
            210                 215                 220

Ser Phe Phe Gly Ala Phe Leu Val Gly
225                 230

<210> SEQ ID NO 34
<211> LENGTH: 225
<212> TYPE: PRT
<213> ORGANISM: Artificial
<220> FEATURE:
<223> OTHER INFORMATION: fusion protein hCol11s-hTRAIL_Glu116_Gly281

<400> SEQUENCE: 34

Met Asn Phe Gly Phe Ser Leu Ile Phe Leu Val Leu Val Leu Lys Gly
1               5                   10                  15

Val Gln Cys Gly Leu Pro Cys Glu Cys Ser Gln Leu Arg Lys Ala Ile
            20                  25                  30

Gly Glu Met Asp Asn Gln Val Ser Gln Leu Thr Ser Glu Leu Lys Phe
            35                  40                  45

Ile Lys Asn Ala Val Ala Gly Val Arg Glu Thr Glu Arg Gly Pro Gln
50                  55                  60

Arg Val Ala Ala His Ile Thr Gly Thr Arg Gly Arg Ser Asn Thr Leu
65                  70                  75                  80

Ser Ser Pro Asn Ser Lys Asn Glu Lys Ala Leu Gly Arg Lys Ile Asn
            85                  90                  95

Ser Trp Glu Ser Ser Arg Ser Gly His Ser Phe Leu Ser Asn Leu His
            100                 105                 110

Leu Arg Asn Gly Glu Leu Val Ile His Glu Lys Gly Phe Tyr Tyr Ile
            115                 120                 125

Tyr Ser Gln Thr Tyr Phe Arg Phe Gln Glu Glu Ile Lys Glu Asn Thr
            130                 135                 140

Lys Asn Asp Lys Gln Met Val Gln Tyr Ile Tyr Lys Tyr Thr Ser Tyr
145                 150                 155                 160

Pro Asp Pro Ile Leu Leu Met Lys Ser Ala Arg Asn Ser Cys Trp Ser
                165                 170                 175

Lys Asp Ala Glu Tyr Gly Leu Tyr Ser Ile Tyr Gln Gly Gly Ile Phe
            180                 185                 190

Glu Leu Lys Glu Asn Asp Arg Ile Phe Val Ser Val Thr Asn Glu His
            195                 200                 205

Leu Ile Asp Met Asp His Glu Ala Ser Phe Phe Gly Ala Phe Leu Val
            210                 215                 220
```

Gly
225

<210> SEQ ID NO 35
<211> LENGTH: 247
<212> TYPE: PRT
<213> ORGANISM: Artificial
<220> FEATURE:
<223> OTHER INFORMATION: fusion protein
      FLAG-hCol11-GSS-hTRAIL_Glu116_Gly281

<400> SEQUENCE: 35

Met Asn Phe Gly Phe Ser Leu Ile Phe Leu Val Leu Val Leu Lys Gly
1               5                   10                  15

Val Gln Cys Asp Tyr Lys Asp Asp Asp Lys Gly Leu Pro Cys Glu
            20                  25                  30

Cys Ser Gln Leu Arg Lys Ala Ile Gly Glu Met Asp Asn Gln Val Ser
        35                  40                  45

Gln Leu Thr Ser Glu Leu Lys Phe Ile Lys Asn Ala Val Ala Gly Val
    50                  55                  60

Arg Glu Thr Glu Ser Gly Ser Ser Gly Ser Ser Gly Ser Ser Gly Ser
65                  70                  75                  80

Gly Glu Arg Gly Pro Gln Arg Val Ala Ala His Ile Thr Gly Thr Arg
                85                  90                  95

Gly Arg Ser Asn Thr Leu Ser Ser Pro Asn Ser Lys Asn Glu Lys Ala
            100                 105                 110

Leu Gly Arg Lys Ile Asn Ser Trp Glu Ser Ser Arg Ser Gly His Ser
        115                 120                 125

Phe Leu Ser Asn Leu His Leu Arg Asn Gly Glu Leu Val Ile His Glu
    130                 135                 140

Lys Gly Phe Tyr Tyr Ile Tyr Ser Gln Thr Tyr Phe Arg Phe Gln Glu
145                 150                 155                 160

Glu Ile Lys Glu Asn Thr Lys Asn Asp Lys Gln Met Val Gln Tyr Ile
                165                 170                 175

Tyr Lys Tyr Thr Ser Tyr Pro Asp Pro Ile Leu Leu Met Lys Ser Ala
            180                 185                 190

Arg Asn Ser Cys Trp Ser Lys Asp Ala Glu Tyr Gly Leu Tyr Ser Ile
        195                 200                 205

Tyr Gln Gly Gly Ile Phe Glu Leu Lys Glu Asn Asp Arg Ile Phe Val
    210                 215                 220

Ser Val Thr Asn Glu His Leu Ile Asp Met Asp His Glu Ala Ser Phe
225                 230                 235                 240

Phe Gly Ala Phe Leu Val Gly
                245

<210> SEQ ID NO 36
<211> LENGTH: 237
<212> TYPE: PRT
<213> ORGANISM: Artificial
<220> FEATURE:
<223> OTHER INFORMATION: fusion protein
      Sp1-hTRAIL_Glu116_Gly281-GSS-col111

<400> SEQUENCE: 36

Met Asn Phe Gly Phe Ser Leu Ile Phe Leu Val Leu Val Leu Lys Gly
1               5                   10                  15

Val Gln Cys Glu Arg Gly Pro Gln Arg Val Ala Ala His Ile Thr Gly
            20                  25                  30

Thr Arg Gly Arg Ser Asn Thr Leu Ser Ser Pro Asn Ser Lys Asn Glu
            35                  40                  45

Lys Ala Leu Gly Arg Lys Ile Asn Ser Trp Glu Ser Ser Arg Ser Gly
 50                  55                  60

His Ser Phe Leu Ser Asn Leu His Leu Arg Asn Gly Glu Leu Val Ile
 65                  70                  75                  80

His Glu Lys Gly Phe Tyr Tyr Ile Tyr Ser Gln Thr Tyr Phe Arg Phe
                85                  90                  95

Gln Glu Glu Ile Lys Glu Asn Thr Lys Asn Asp Lys Gln Met Val Gln
            100                 105                 110

Tyr Ile Tyr Lys Tyr Thr Ser Tyr Pro Asp Pro Ile Leu Leu Met Lys
            115                 120                 125

Ser Ala Arg Asn Ser Cys Trp Ser Lys Asp Ala Glu Tyr Gly Leu Tyr
130                 135                 140

Ser Ile Tyr Gln Gly Gly Ile Phe Glu Leu Lys Glu Asn Asp Arg Ile
145                 150                 155                 160

Phe Val Ser Val Thr Asn Glu His Leu Ile Asp Met Asp His Glu Ala
                165                 170                 175

Ser Phe Phe Gly Ala Phe Leu Val Gly Ser Ser Gly Ser Ser Gly Ser
            180                 185                 190

Ser Gly Ser Gly Leu Pro Cys Glu Cys Ser Gln Leu Arg Lys Ala Ile
            195                 200                 205

Gly Glu Met Asp Asn Gln Val Ser Gln Leu Thr Ser Glu Leu Lys Phe
            210                 215                 220

Ile Lys Asn Ala Val Ala Gly Val Arg Glu Thr Glu Ser
225                 230                 235

<210> SEQ ID NO 37
<211> LENGTH: 238
<212> TYPE: PRT
<213> ORGANISM: Artificial
<220> FEATURE:
<223> OTHER INFORMATION: fusion protein
      Sp3-hTRAIL_Glu116_Gly281-GSS-coll11

<400> SEQUENCE: 37

Met Glu Thr Asp Thr Leu Leu Leu Trp Val Leu Leu Leu Trp Val Pro
 1               5                  10                  15

Ala Gly Asn Gly Glu Arg Gly Pro Gln Arg Val Ala Ala His Ile Thr
             20                  25                  30

Gly Thr Arg Gly Arg Ser Asn Thr Leu Ser Ser Pro Asn Ser Lys Asn
         35                  40                  45

Glu Lys Ala Leu Gly Arg Lys Ile Asn Ser Trp Glu Ser Ser Arg Ser
 50                  55                  60

Gly His Ser Phe Leu Ser Asn Leu His Leu Arg Asn Gly Glu Leu Val
 65                  70                  75                  80

Ile His Glu Lys Gly Phe Tyr Tyr Ile Tyr Ser Gln Thr Tyr Phe Arg
                 85                  90                  95

Phe Gln Glu Glu Ile Lys Glu Asn Thr Lys Asn Asp Lys Gln Met Val
            100                 105                 110

Gln Tyr Ile Tyr Lys Tyr Thr Ser Tyr Pro Asp Pro Ile Leu Leu Met
            115                 120                 125

Lys Ser Ala Arg Asn Ser Cys Trp Ser Lys Asp Ala Glu Tyr Gly Leu
130                 135                 140

Tyr Ser Ile Tyr Gln Gly Gly Ile Phe Glu Leu Lys Glu Asn Asp Arg

```
                145                 150                 155                 160
Ile Phe Val Ser Val Thr Asn Glu His Leu Ile Asp Met Asp His Glu
                    165                 170                 175

Ala Ser Phe Phe Gly Ala Phe Leu Val Gly Ser Gly Ser Ser Gly
                180                 185                 190

Ser Ser Gly Ser Gly Leu Pro Cys Glu Cys Ser Gln Leu Arg Lys Ala
            195                 200                 205

Ile Gly Glu Met Asp Asn Gln Val Ser Gln Leu Thr Ser Glu Leu Lys
210                 215                 220

Phe Ile Lys Asn Ala Val Ala Gly Val Arg Glu Thr Glu Ser
225                 230                 235

<210> SEQ ID NO 38
<211> LENGTH: 1045
<212> TYPE: DNA
<213> ORGANISM: Artificial
<220> FEATURE:
<223> OTHER INFORMATION: coding sequence corresponding to SEQ ID NO:26
      SP-hsTrailsyn-SPD-construct-1

<400> SEQUENCE: 38
aagcttgccg ccaccatgga gaccgataca ctgctcttgt gggtgctctt gctgtgggtt      60
cctgcaggta atggtcaaag agtcgcagct cacatcactg ggactagagg caggagtaac    120
accctgagtt ctcccaattc caagaacgag aaagccctgg gtaggaagat caactcctgg    180
gaaagctcca gaagcggcca tagctttctt agcaacctcc acttgaggaa tggcgaactt    240
gtgatccatg agaagggctt ctactacatc tacagccaga cgtacttcag gttccaggag    300
gaaatcaagg agaacaccaa gaacgacaag cagatggtgc aatacatcta caagtacacg    360
tcatacccct gatcctatact gctgatgaag tccgccagaa acagttgctg gagcaaagac    420
gctgaatacg gcctgtattc catctatcag ggcggtatct ttgaactcaa ggagaacgac    480
aggatcttcg tgtctgtgac aaacgagcat ctgatcgaca tggaccatga gcgtctttc     540 ttcggtgcct tcttggtggg atccggtttg ccagatgttg cttctttgag acaacaggtt    600
gaggctttgc agggtcaagt ccagcacttg caggctgctt tctctcaata caagaaggtt    660
gagttgttcc caaatggtca atctgttggc gaaaagattt tcaagactgc tggtttcgtc    720
aaaccattca cggaggcaca attattgtgt actcaggctg gtggacagtt ggcctctcca    780
cgttctgccg ctgagaacgc cgccttgcaa caattagtcg tagctaagaa cgaggctgct    840
ttcttgagca tgactgattc caagacagag ggcaagttca cctacccaac aggagaatcc    900
ttggtctatt ctaattgggc acctggagag cccaacgatg atggcggctc agaggactgt    960
gtggaaatct tcaccaatgg caagtggaat gacagagctt gtggagagaa cgtttggtg   1020 gtctgtgagt tctaatagcg gccgc                                         1045

<210> SEQ ID NO 39
<211> LENGTH: 1057
<212> TYPE: DNA
<213> ORGANISM: Artificial
<220> FEATURE:
<223> OTHER INFORMATION: coding sequence corresponding to SEQ ID NO:27
      SP-hsTrailsyn-SPD-construct-2

<400> SEQUENCE: 39
aagcttgccg ccaccatgga gaccgataca ctgctcttgt gggtactctt gctgtgggtt      60
ccgggatcta ccggtgaacg tggtcctcaa agagtcgcag ctcacatcac tgggactaga    120
```

-continued

```
ggcaggagta acaccctgag ttctcccaat tccaagaacg agaaagccct gggtaggaag    180
atcaactcct gggaaagctc cagaagcggc catagctttc ttagcaacct ccacttgagg    240
aatggcgaac ttgtgatcca tgagaagggc ttctactaca tctacagcca gacgtacttc    300
aggttccagg aggaaatcaa ggagaacacc aagaacgaca agcagatggt gcaatacatc    360
tacaagtaca cgtcataccc tgatcctata ctgctgatga agtccgccag aaacagttgc    420
tggagcaaag acgctgaata cggcctgtat tccatctatc agggcggtat ctttgaactc    480
aaggagaacg acaggatctt cgtgtctgtg acaaacgagc atctgatcga catggaccat    540
gaagcgtctt tcttcggtgc cttcttggtg ggatccggtt tgccagatgt tgcttctttg    600
agacaacagg ttgaggcttt gcagggtcaa gtccagcact tgcaggctgc tttctctcaa    660
tacaagaagg ttgagttgtt cccaaatggt caatctgttg gcgaaaagat tttcaagact    720
gctggtttcg tcaaaccatt cacggaggca caattattgt gtactcaggc tggtggacag    780
ttggcctctc cacgttctgc cgctgagaac gccgccttgc aacaattagt cgtagctaag    840
aacgaggctg ctttcttgag catgactgat tccaagacag agggcaagtt cacctaccca    900
acaggagaat ccttggtcta ttctaattgg gcacctggag agcccaacga tgatggcggc    960
tcagaggact gtgtggaaat cttcaccaat ggcaagtgga atgacagagc ttgtggagag   1020
aagcgtttgg tggtctgtga gttctaatag cggccgc                            1057
```

<210> SEQ ID NO 40
<211> LENGTH: 346
<212> TYPE: PRT
<213> ORGANISM: Artificial
<220> FEATURE:
<223> OTHER INFORMATION: fusion protein CD95L-ASPD

<400> SEQUENCE: 40

```
Met Glu Thr Asp Thr Leu Leu Leu Trp Val Leu Leu Leu Trp Val Pro
1               5                   10                  15

Gly Ser Thr Gly Glu Leu Arg Lys Val Ala His Leu Thr Gly Lys Ser
            20                  25                  30

Asn Ser Arg Ser Met Pro Leu Glu Trp Glu Asp Thr Tyr Gly Ile Val
        35                  40                  45

Leu Leu Ser Gly Val Lys Tyr Lys Lys Gly Gly Leu Val Ile Asn Glu
    50                  55                  60

Thr Gly Leu Tyr Phe Val Tyr Ser Lys Val Tyr Phe Arg Gly Gln Ser
65                  70                  75                  80

Cys Asn Asn Leu Pro Leu Ser His Lys Val Tyr Met Arg Asn Ser Lys
                85                  90                  95

Tyr Pro Gln Asp Leu Val Met Met Glu Gly Lys Met Met Ser Tyr Cys
            100                 105                 110

Thr Thr Gly Gln Met Trp Ala Arg Ser Ser Tyr Val Gly Ala Val Phe
        115                 120                 125

Asn Leu Thr Ser Ala Asp His Leu Tyr Val Asn Val Ser Glu Leu Ser
    130                 135                 140

Leu Val Asn Phe Glu Glu Ser Gln Thr Phe Phe Gly Leu Tyr Lys Leu
145                 150                 155                 160

Gly Ser Ser Gly Ser Ser Gly Ser Ser Gly Ser Gly Leu Pro Asp Val
                165                 170                 175

Ala Ser Leu Arg Gln Gln Val Glu Ala Leu Gln Gly Gln Val Gln His
            180                 185                 190

Leu Gln Ala Ala Phe Ser Gln Tyr Lys Lys Val Glu Leu Phe Pro Asn
```

```
                195                 200                 205
Gly Gln Ser Val Gly Glu Lys Ile Phe Lys Thr Ala Gly Phe Val Lys
            210                 215                 220

Pro Phe Thr Glu Ala Gln Leu Leu Cys Thr Gln Ala Gly Gly Gln Leu
225                 230                 235                 240

Ala Ser Pro Arg Ser Ala Glu Asn Ala Leu Gln Gln Leu Val
                245                 250                 255

Val Ala Lys Asn Glu Ala Ala Phe Leu Ser Met Thr Asp Ser Lys Thr
            260                 265                 270

Glu Gly Lys Phe Thr Tyr Pro Thr Gly Glu Ser Leu Val Tyr Ser Asn
            275                 280                 285

Trp Ala Pro Gly Glu Pro Asn Asp Asp Gly Ser Glu Asp Cys Val
            290                 295                 300

Glu Ile Phe Thr Asn Gly Lys Trp Asn Asp Arg Ala Cys Gly Glu Lys
305                 310                 315                 320

Arg Leu Val Val Cys Glu Phe Gly Gly Ser Pro Ser Ser Ser Ser
                325                 330                 335

Ser Ala Trp Ser His Pro Gln Phe Glu Lys
            340                 345

<210> SEQ ID NO 41
<211> LENGTH: 356
<212> TYPE: PRT
<213> ORGANISM: Artificial
<220> FEATURE:
<223> OTHER INFORMATION: fusion protein Sp-LIGHT-ASPD

<400> SEQUENCE: 41

Met Glu Thr Asp Thr Leu Leu Leu Trp Val Leu Leu Leu Trp Val Pro
1               5                   10                  15

Gly Ser Thr Gly Glu Val Asn Pro Ala Ala His Leu Thr Gly Ala Asn
                20                  25                  30

Ser Ser Leu Thr Gly Ser Gly Gly Pro Leu Leu Trp Glu Thr Gln Leu
            35                  40                  45

Gly Leu Ala Phe Leu Arg Gly Leu Ser Tyr His Asp Gly Ala Leu Val
        50                  55                  60

Val Thr Lys Ala Gly Tyr Tyr Tyr Ile Tyr Ser Lys Val Gln Leu Gly
65                  70                  75                  80

Gly Val Gly Cys Pro Leu Gly Leu Ala Ser Thr Ile Thr His Gly Leu
                85                  90                  95

Tyr Lys Arg Thr Pro Arg Tyr Pro Glu Glu Leu Glu Leu Leu Val Ser
            100                 105                 110

Gln Gln Ser Pro Cys Gly Arg Ala Thr Ser Ser Ser Arg Val Trp Trp
            115                 120                 125

Asp Ser Ser Phe Leu Gly Gly Val Val His Leu Glu Ala Gly Glu Glu
        130                 135                 140

Val Val Val Arg Val Leu Asp Glu Arg Leu Val Arg Leu Arg Asp Gly
145                 150                 155                 160

Thr Arg Ser Tyr Phe Gly Ala Phe Met Val Gly Ser Ser Gly Ser Ser
                165                 170                 175

Gly Ser Ser Gly Ser Gly Leu Pro Asp Val Ala Ser Leu Arg Gln Gln
            180                 185                 190

Val Glu Ala Leu Gln Gly Gln Val Gln His Leu Gln Ala Ala Phe Ser
            195                 200                 205

Gln Tyr Lys Lys Val Glu Leu Phe Pro Asn Gly Gln Ser Val Gly Glu
```

```
          210                 215                 220
Lys Ile Phe Lys Thr Ala Gly Phe Val Lys Pro Phe Thr Glu Ala Gln
225                 230                 235                 240

Leu Leu Cys Thr Gln Ala Gly Gly Gln Leu Ala Ser Pro Arg Ser Ala
            245                 250                 255

Ala Glu Asn Ala Ala Leu Gln Gln Leu Val Val Ala Lys Asn Glu Ala
                260                 265                 270

Ala Phe Leu Ser Met Thr Asp Ser Lys Thr Glu Gly Lys Phe Thr Tyr
            275                 280                 285

Pro Thr Gly Glu Ser Leu Val Tyr Ser Asn Trp Ala Pro Gly Glu Pro
        290                 295                 300

Asn Asp Asp Gly Gly Ser Glu Asp Cys Val Glu Ile Phe Thr Asn Gly
305                 310                 315                 320

Lys Trp Asn Asp Arg Ala Cys Gly Glu Lys Arg Leu Val Val Cys Glu
                325                 330                 335

Phe Gly Gly Ser Pro Ser Ser Ser Ser Ser Ala Trp Ser His Pro
            340                 345                 350

Gln Phe Glu Lys
        355

<210> SEQ ID NO 42
<211> LENGTH: 1129
<212> TYPE: DNA
<213> ORGANISM: Artificial
<220> FEATURE:
<223> OTHER INFORMATION: expression cassette of Sp-TRAIL-ASPD

<400> SEQUENCE: 42
aagcttgccg ccaccatgga gaccgataca ctgctcttgt gggtgctctt gctgtgggtt      60
cctgcaggta atggtcaaag agtcgcagct cacatcactg gactagagg caggagtaac     120
accctgagtt ctcccaattc caagaacgag aaagccctgg gtaggaagat caactcctgg     180
gaaagctcca gaagcggcca tagctttctt agcaacctcc acttgaggaa tggcgaactt     240
gtgatccatg agaagggctt ctactacatc tacagccaga cgtacttcag gttccaggag     300
gaaatcaagg agaacaccaa gaacgacaag cagatggtgc aatacatcta caagtacacg     360
tcatacccctg atcctatact gctgatgaag tccgccagaa acagttgctg gagcaaagac     420
gctgaatacg gcctgtattc catctatcag ggcggtatct ttgaactcaa ggagaacgac     480
aggatcttcg tgtctgtgac aaacgagcat ctgatcgaca tggaccatga gcgtctttc      540
ttcggtgcct tcttggtggg atcctctggt tcgagtggtt cgagtggttc tggattgcca     600
gacgttgctt ctttgagaca acaggttgag gctttgcagg tcaagtccaa gcacttgcag     660
gctgctttct ctcaatacaa gaaggttgag ttgttcccaa acgtcaatc tgttggcgaa      720
aagattttca agactgctgg tttcgtcaaa ccattcacgg aggcacaatt attgtgtact     780
caggctggtg gacagttggc ctctccacgt tctgccgctg agaacgccgc cttgcaacag     840
ttggtcgtag ctaagaacga ggctgctttc ttgagcatga ctgattccaa gacagagggc     900
aagttcaccct acccaacagg agaatccttg gtctattcta attgggcacc tggagagccc     960
aacgatgatg gcggctcaga ggactgtgtg gaaatcttca ccaatggcaa gtggaatgac    1020
agagcttgtg gagagaagcg tttggtggtc tgtgagttcg gaggcagtcc ttcatcttca    1080
tctagctctg cctggtcgca tccacaattc gagaaataat agcggccgc                1129

<210> SEQ ID NO 43
```

<211> LENGTH: 367
<212> TYPE: PRT
<213> ORGANISM: Artificial
<220> FEATURE:
<223> OTHER INFORMATION: fusion protein Sp-TRAIL-ASPD

<400> SEQUENCE: 43

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
            20                  25                  30

Arg Ser Asn Thr Leu Ser Ser Pro Asn Ser Lys Asn Glu Lys Ala Leu
        35                  40                  45

Gly Arg Lys Ile Asn Ser Trp Glu Ser Ser Arg Ser Gly His Ser Phe
    50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Tyr Phe Arg Phe Gln Glu Glu
                85                  90                  95

Ile Lys Glu Asn Thr Lys Asn Asp Lys Gln Met Val Gln Tyr Ile Tyr
            100                 105                 110

Lys Tyr Thr Ser Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Gly Ser Gly Ser Gly Ser
            180                 185                 190

Gly Leu Pro Asp Val Ala Ser Leu Arg Gln Gln Val Glu Ala Leu Gln
        195                 200                 205

Gly Gln Val Gln His Leu Gln Ala Ala Phe Ser Gln Tyr Lys Lys Val
    210                 215                 220

Glu Leu Phe Pro Asn Gly Gln Ser Val Gly Glu Lys Ile Phe Lys Thr
225                 230                 235                 240

Ala Gly Phe Val Lys Pro Phe Thr Glu Ala Gln Leu Leu Cys Thr Gln
                245                 250                 255

Ala Gly Gly Gln Leu Ala Ser Pro Arg Ser Ala Ala Glu Asn Ala Ala
            260                 265                 270

Leu Gln Gln Leu Val Val Ala Lys Asn Glu Ala Ala Phe Leu Ser Met
        275                 280                 285

Thr Asp Ser Lys Thr Glu Gly Lys Phe Thr Tyr Pro Thr Gly Glu Ser
    290                 295                 300

Leu Val Tyr Ser Asn Trp Ala Pro Gly Glu Pro Asn Asp Asp Gly Gly
305                 310                 315                 320

Ser Glu Asp Cys Val Glu Ile Phe Thr Asn Gly Lys Trp Asn Asp Arg
                325                 330                 335

Ala Cys Gly Glu Lys Arg Leu Val Val Cys Glu Phe Gly Gly Ser Pro
            340                 345                 350

Ser Ser Ser Ser Ser Ser Ala Trp Ser His Pro Gln Phe Glu Lys
        355                 360                 365

<210> SEQ ID NO 44

```
<211> LENGTH: 246
<212> TYPE: PRT
<213> ORGANISM: Artificial
<220> FEATURE:
<223> OTHER INFORMATION: fusion protein Sp-TRAIL-ACCSPD

<400> SEQUENCE: 44
```

| Met<br>1 | Glu | Thr | Asp | Thr<br>5 | Leu | Leu | Leu | Trp | Val<br>10 | Leu | Leu | Leu | Trp | Val<br>15 | Pro |
|---|---|---|---|---|---|---|---|---|---|---|---|---|---|---|---|
| Ala | Gly | Asn | Gly<br>20 | Gln | Arg | Val | Ala | Ala<br>25 | His | Ile | Thr | Gly | Thr<br>30 | Arg | Gly |
| Arg | Ser | Asn<br>35 | Thr | Leu | Ser | Ser | Pro<br>40 | Asn | Ser | Lys | Asn | Glu<br>45 | Lys | Ala | Leu |
| Gly | Arg<br>50 | Lys | Ile | Asn | Ser | Trp<br>55 | Glu | Ser | Ser | Arg | Ser<br>60 | Gly | His | Ser | Phe |
| Leu<br>65 | Ser | Asn | Leu | His | Leu<br>70 | Arg | Asn | Gly | Glu | Leu<br>75 | Val | Ile | His | Glu | Lys<br>80 |
| Gly | Phe | Tyr | Tyr | Ile<br>85 | Tyr | Ser | Gln | Thr | Tyr<br>90 | Phe | Arg | Phe | Gln | Glu<br>95 | Glu |
| Ile | Lys | Glu | Asn<br>100 | Thr | Lys | Asn | Asp | Lys<br>105 | Gln | Met | Val | Gln | Tyr<br>110 | Ile | Tyr |
| Lys | Tyr | Thr<br>115 | Ser | Tyr | Pro | Asp | Pro<br>120 | Ile | Leu | Leu | Met | Lys<br>125 | Ser | Ala | Arg |
| Asn | Ser<br>130 | Cys | Trp | Ser | Lys | Asp<br>135 | Ala | Glu | Tyr | Gly | Leu<br>140 | Tyr | Ser | Ile | Tyr |
| Gln<br>145 | Gly | Gly | Ile | Phe | Glu<br>150 | Leu | Lys | Glu | Asn | Asp<br>155 | Arg | Ile | Phe | Val | Ser<br>160 |
| Val | Thr | Asn | Glu | His<br>165 | Leu | Ile | Asp | Met | Asp<br>170 | His | Glu | Ala | Ser | Phe<br>175 | Phe |
| Gly | Ala | Phe | Leu<br>180 | Val | Gly | Ser | Ser | Gly<br>185 | Ser | Ser | Gly | Ser | Gly<br>190 | Ser | Ser |
| Gly | Leu | Pro<br>195 | Asp | Val | Ala | Ser | Leu<br>200 | Arg | Gln | Gln | Val | Glu<br>205 | Ala | Leu | Gln |
| Gly | Gln<br>210 | Val | Gln | His | Leu | Gln<br>215 | Ala | Ala | Phe | Ser | Gln<br>220 | Tyr | Lys | Lys | Val |
| Glu<br>225 | Leu | Phe | Pro | Asn | Gly<br>230 | Pro | Ser | Ser | Ser | Ser<br>235 | Ser | Ser | Ala | Trp | Ser<br>240 |
| His | Pro | Gln | Phe | Glu<br>245 | Lys | | | | | | | | | | |

```
<210> SEQ ID NO 45
<211> LENGTH: 365
<212> TYPE: PRT
<213> ORGANISM: Artificial
<220> FEATURE:
<223> OTHER INFORMATION: fusion protein Sp-TRAIL-ACol11

<400> SEQUENCE: 45
```

| Met<br>1 | Glu | Thr | Asp | Thr<br>5 | Leu | Leu | Leu | Trp | Val<br>10 | Leu | Leu | Leu | Trp | Val<br>15 | Pro |
|---|---|---|---|---|---|---|---|---|---|---|---|---|---|---|---|
| Ala | Gly | Asn | Gly<br>20 | Gln | Arg | Val | Ala | Ala<br>25 | His | Ile | Thr | Gly | Thr<br>30 | Arg | Gly |
| Arg | Ser | Asn<br>35 | Thr | Leu | Ser | Ser | Pro<br>40 | Asn | Ser | Lys | Asn | Glu<br>45 | Lys | Ala | Leu |
| Gly | Arg<br>50 | Lys | Ile | Asn | Ser | Trp<br>55 | Glu | Ser | Ser | Arg | Ser<br>60 | Gly | His | Ser | Phe |
| Leu | Ser | Asn | Leu | His | Leu | Arg | Asn | Gly | Glu | Leu | Val | Ile | His | Glu | Lys |

```
                65                  70                  75                  80
Gly Phe Tyr Tyr Ile Tyr Ser Gln Thr Tyr Phe Arg Phe Gln Glu Glu
                    85                  90                  95

Ile Lys Glu Asn Thr Lys Asn Asp Lys Gln Met Val Gln Tyr Ile Tyr
                100                 105                 110

Lys Tyr Thr Ser Tyr Pro Asp Pro Ile Leu Leu Met Lys Ser Ala Arg
                115                 120                 125

Asn Ser Cys Trp Ser Lys Asp Ala Glu Tyr Gly Leu Tyr Ser Ile Tyr
            130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser
                180                 185                 190

Gln Leu Arg Lys Ala Ile Gly Glu Met Asp Asn Gln Val Ser Gln Leu
                195                 200                 205

Thr Ser Glu Leu Lys Phe Ile Lys Asn Ala Val Ala Gly Val Arg Glu
                210                 215                 220

Thr Glu Ser Lys Ile Tyr Leu Leu Val Lys Glu Lys Arg Tyr Ala
225                 230                 235                 240

Asp Ala Gln Leu Ser Cys Gln Gly Arg Gly Gly Thr Leu Ser Met Pro
                245                 250                 255

Lys Asp Glu Ala Ala Asn Gly Leu Met Ala Ala Tyr Leu Ala Gln Ala
                260                 265                 270

Gly Leu Ala Arg Val Phe Ile Gly Ile Asn Asp Leu Glu Lys Glu Gly
                275                 280                 285

Ala Phe Val Tyr Ser Asp His Ser Pro Met Arg Thr Phe Asn Lys Trp
                290                 295                 300

Arg Ser Gly Glu Pro Asn Asn Ala Tyr Asp Glu Glu Asp Cys Val Glu
305                 310                 315                 320

Met Val Ala Ser Gly Gly Trp Asn Asp Val Ala Cys His Thr Thr Met
                325                 330                 335

Tyr Phe Met Cys Glu Phe Asp Lys Glu Asn Met Gly Ser Pro Ser Ser
                340                 345                 350

Ser Ser Ser Ser Ala Trp Ser His Pro Gln Phe Glu Lys
                355                 360                 365

<210> SEQ ID NO 46
<211> LENGTH: 246
<212> TYPE: PRT
<213> ORGANISM: Artificial
<220> FEATURE:
<223> OTHER INFORMATION: fusion protein Sp-TRAIL-ACC11

<400> SEQUENCE: 46

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
                20                  25                  30

Arg Ser Asn Thr Leu Ser Ser Pro Asn Ser Lys Asn Glu Lys Ala Leu
            35                  40                  45

Gly Arg Lys Ile Asn Ser Trp Glu Ser Ser Arg Ser Gly His Ser Phe
        50                  55                  60

Leu Ser Asn Leu His Leu Arg Asn Gly Glu Leu Val Ile His Glu Lys
```

Gly Phe Tyr Tyr Ile Tyr Ser Gln Thr Tyr Phe Arg Phe Gln Glu Glu
65                  70                  75                  80

Ile Lys Glu Asn Thr Lys Asn Asp Lys Gln Met Val Gln Tyr Ile Tyr
                85                  90                  95

Lys Tyr Thr Ser Tyr Pro Asp Pro Ile Leu Leu Met Lys Ser Ala Arg
            100                 105                 110

Asn Ser Cys Trp Ser Lys Asp Ala Glu Tyr Gly Leu Tyr Ser Ile Tyr
        115                 120                 125

Gln Gly Gly Ile Phe Glu Leu Lys Glu Asn Asp Arg Ile Phe Val Ser
    130                 135                 140

Val Thr Asn Glu His Leu Ile Asp Met Asp His Glu Ala Ser Phe Phe
145                 150                 155                 160

Gly Ala Phe Leu Val Gly Ser Ser Gly Ser Ser Gly Ser Ser Gly Ser
                165                 170                 175

Gly Ser Gln Leu Arg Lys Ala Ile Gly Glu Met Asp Asn Gln Val Ser
            180                 185                 190

Gln Leu Thr Ser Glu Leu Lys Phe Ile Lys Asn Ala Val Ala Gly Val
        195                 200                 205

Arg Glu Thr Glu Ser Gly Pro Ser Ser Ser Ser Ser Ala Trp Ser
    210                 215                 220

His Pro Gln Phe Glu Lys
225                 230                 235                 240

His Pro Gln Phe Glu Lys
                245

<210> SEQ ID NO 47
<211> LENGTH: 367
<212> TYPE: PRT
<213> ORGANISM: Artificial
<220> FEATURE:
<223> OTHER INFORMATION: fusion protein Sp-TRAILR1mut-ASPD

<400> SEQUENCE: 47

Met Glu Thr Asp Thr Leu Leu Leu Trp Val Leu Leu Leu Trp Val Pro
1               5                   10                  15

Ala Gly Asn Gly Gln Arg Val Ala Ala His Ile Thr Gly Thr Arg Gly
                20                  25                  30

Arg Ser Asn Thr Leu Ser Ser Pro Asn Ser Lys Asn Glu Lys Ala Leu
            35                  40                  45

Gly Arg Lys Ile Asn Ser Trp Glu Ser Ser Arg Ser Gly His Ser Phe
        50                  55                  60

Leu Ser Asn Leu His Leu Arg Asn Gly Glu Leu Val Ile His Glu Lys
65                  70                  75                  80

Gly Phe Tyr Tyr Ile Tyr Ser Gln Thr Ala Phe Arg Phe Ser Glu Glu
                85                  90                  95

Ile Lys Glu Val Thr Arg Asn Asp Lys Gln Met Val Gln Tyr Ile Tyr
            100                 105                 110

Lys Trp Thr Asp Tyr Pro Asp Pro Ile Leu Leu Met Lys Ser Ala Arg
        115                 120                 125

Asn Ser Cys Trp Ser Lys Asp Ala Glu Tyr Gly Leu Tyr Ser Ile Tyr
    130                 135                 140

Gln Gly Gly Ile Phe Glu Leu Lys Glu Asn Asp Arg Ile Phe Val Ser
145                 150                 155                 160

Val Thr Asn Glu His Leu Ile Asp Met Asp His Glu Ala Ser Phe Phe
                165                 170                 175

Gly Ala Phe Leu Val Gly Ser Ser Gly Ser Ser Gly Ser Ser Gly Ser

```
            180                 185                 190
Gly Leu Pro Asp Val Ala Ser Leu Arg Gln Gln Val Glu Ala Leu Gln
                195                 200                 205
Gly Gln Val Gln His Leu Gln Ala Ala Phe Ser Gln Tyr Lys Lys Val
                210                 215                 220
Glu Leu Phe Pro Asn Gly Gln Ser Val Gly Glu Lys Ile Phe Lys Thr
225                 230                 235                 240
Ala Gly Phe Val Lys Pro Phe Thr Glu Ala Gln Leu Leu Cys Thr Gln
                245                 250                 255
Ala Gly Gly Gln Leu Ala Ser Pro Arg Ser Ala Ala Glu Asn Ala Ala
                260                 265                 270
Leu Gln Gln Leu Val Val Ala Lys Asn Glu Ala Ala Phe Leu Ser Met
                275                 280                 285
Thr Asp Ser Lys Thr Glu Gly Lys Phe Thr Tyr Pro Thr Gly Glu Ser
                290                 295                 300
Leu Val Tyr Ser Asn Trp Ala Pro Gly Glu Pro Asn Asp Asp Gly Gly
305                 310                 315                 320
Ser Glu Asp Cys Val Glu Ile Phe Thr Asn Gly Lys Trp Asn Asp Arg
                325                 330                 335
Ala Cys Gly Glu Lys Arg Leu Val Val Cys Glu Phe Gly Gly Ser Pro
                340                 345                 350
Ser Ser Ser Ser Ser Ala Trp Ser His Pro Gln Phe Glu Lys
                355                 360                 365

<210> SEQ ID NO 48
<211> LENGTH: 367
<212> TYPE: PRT
<213> ORGANISM: Artificial
<220> FEATURE:
<223> OTHER INFORMATION: fusion protein Sp-TRAILR2mut-ASPD

<400> SEQUENCE: 48

Met Glu Thr Asp Thr Leu Leu Leu Trp Val Leu Leu Leu Trp Val Pro
1               5                   10                  15
Ala Gly Asn Gly Gln Arg Val Ala Ala His Ile Thr Gly Thr Arg Gly
                20                  25                  30
Arg Ser Asn Thr Leu Ser Ser Pro Asn Ser Lys Asn Glu Lys Ala Leu
                35                  40                  45
Gly Arg Lys Ile Asn Ser Trp Glu Ser Ser Arg Ser Gly His Ser Phe
            50                  55                  60
Leu Ser Asn Leu His Leu Arg Asn Gly Glu Leu Val Ile His Glu Lys
65              70                  75                  80
Gly Phe Tyr Tyr Ile Tyr Ser Gln Thr Gln Phe Lys Phe Arg Glu Glu
                85                  90                  95
Ile Lys Glu Asn Thr Lys Asn Asp Lys Gln Met Val Gln Tyr Ile Tyr
                100                 105                 110
Lys Tyr Thr Ser Tyr Pro Asp Pro Ile Leu Leu Met Lys Ser Ala Arg
                115                 120                 125
Asn Ser Cys Trp Ser Lys Asp Ala Glu Tyr Gly Leu Tyr Ser Ile Tyr
                130                 135                 140
Gln Gly Gly Ile Phe Glu Leu Lys Glu Asn Asp Arg Ile Phe Val Ser
145                 150                 155                 160
Val Thr Asn Glu Arg Leu Leu Gln Met Asp His Glu Ala Ser Phe Phe
                165                 170                 175
Gly Ala Phe Leu Val Gly Ser Ser Gly Ser Ser Gly Ser Ser Gly Ser
```

```
                    180                 185                 190
Gly Leu Pro Asp Val Ala Ser Leu Arg Gln Gln Val Glu Ala Leu Gln
            195                 200                 205
Gly Gln Val Gln His Leu Gln Ala Ala Phe Ser Gln Tyr Lys Lys Val
    210                 215                 220
Glu Leu Phe Pro Asn Gly Gln Ser Val Gly Glu Lys Ile Phe Lys Thr
225                 230                 235                 240
Ala Gly Phe Val Lys Pro Phe Thr Glu Ala Gln Leu Leu Cys Thr Gln
            245                 250                 255
Ala Gly Gly Gln Leu Ala Ser Pro Arg Ser Ala Ala Glu Asn Ala Ala
            260                 265                 270
Leu Gln Gln Leu Val Val Ala Lys Asn Glu Ala Ala Phe Leu Ser Met
            275                 280                 285
Thr Asp Ser Lys Thr Glu Gly Lys Phe Thr Tyr Pro Thr Gly Glu Ser
            290                 295                 300
Leu Val Tyr Ser Asn Trp Ala Pro Gly Glu Pro Asn Asp Asp Gly Gly
305                 310                 315                 320
Ser Glu Asp Cys Val Glu Ile Phe Thr Asn Gly Lys Trp Asn Asp Arg
            325                 330                 335
Ala Cys Gly Glu Lys Arg Leu Val Val Cys Glu Phe Gly Gly Ser Pro
            340                 345                 350
Ser Ser Ser Ser Ser Ala Trp Ser His Pro Gln Phe Glu Lys
            355                 360                 365

<210> SEQ ID NO 49
<211> LENGTH: 367
<212> TYPE: PRT
<213> ORGANISM: Artificial
<220> FEATURE:
<223> OTHER INFORMATION: fusion protein Sp-TRAIL-ASPD_F335A

<400> SEQUENCE: 49

Met Glu Thr Asp Thr Leu Leu Leu Trp Val Leu Leu Leu Trp Val Pro
1               5                   10                  15
Ala Gly Asn Gly Gln Arg Val Ala Ala His Ile Thr Gly Thr Arg Gly
            20                  25                  30
Arg Ser Asn Thr Leu Ser Ser Pro Asn Ser Lys Asn Glu Lys Ala Leu
        35                  40                  45
Gly Arg Lys Ile Asn Ser Trp Glu Ser Ser Arg Ser Gly His Ser Phe
    50                  55                  60
Leu Ser Asn Leu His Leu Arg Asn Gly Glu Leu Val Ile His Glu Lys
65                  70                  75                  80
Gly Phe Tyr Tyr Ile Tyr Ser Gln Thr Tyr Phe Arg Phe Gln Glu Glu
                85                  90                  95
Ile Lys Glu Asn Thr Lys Asn Asp Lys Gln Met Val Gln Tyr Ile Tyr
            100                 105                 110
Lys Tyr Thr Ser Tyr Pro Asp Pro Ile Leu Leu Met Lys Ser Ala Arg
        115                 120                 125
Asn Ser Cys Trp Ser Lys Asp Ala Glu Tyr Gly Leu Tyr Ser Ile Tyr
    130                 135                 140
Gln Gly Gly Ile Phe Glu Leu Lys Glu Asn Asp Arg Ile Phe Val Ser
145                 150                 155                 160
Val Thr Asn Glu His Leu Ile Asp Met Asp His Glu Ala Ser Phe Phe
                165                 170                 175
Gly Ala Phe Leu Val Gly Ser Ser Gly Ser Ser Gly Ser Ser Gly Ser
```

```
            180                 185                 190
Gly Leu Pro Asp Val Ala Ser Leu Arg Gln Gln Val Glu Ala Leu Gln
            195                 200                 205
Gly Gln Val Gln His Leu Gln Ala Ala Phe Ser Gln Tyr Lys Lys Val
    210                 215                 220
Glu Leu Phe Pro Asn Gly Gln Ser Val Gly Glu Lys Ile Phe Lys Thr
225                 230                 235                 240
Ala Gly Phe Val Lys Pro Phe Thr Glu Ala Gln Leu Leu Cys Thr Gln
                245                 250                 255
Ala Gly Gly Gln Leu Ala Ser Pro Arg Ser Ala Ala Glu Asn Ala Ala
            260                 265                 270
Leu Gln Gln Leu Val Val Ala Lys Asn Glu Ala Ala Phe Leu Ser Met
        275                 280                 285
Thr Asp Ser Lys Thr Glu Gly Lys Phe Thr Tyr Pro Thr Gly Glu Ser
    290                 295                 300
Leu Val Tyr Ser Asn Trp Ala Pro Gly Glu Pro Asn Asp Asp Gly Gly
305                 310                 315                 320
Ser Glu Asp Cys Val Glu Ile Ala Thr Asn Gly Lys Trp Asn Asp Arg
                325                 330                 335
Ala Cys Gly Glu Lys Arg Leu Val Val Cys Glu Phe Gly Gly Ser Pro
            340                 345                 350
Ser Ser Ser Ser Ser Ala Trp Ser His Pro Gln Phe Glu Lys
        355                 360                 365

<210> SEQ ID NO 50
<211> LENGTH: 367
<212> TYPE: PRT
<213> ORGANISM: Artificial
<220> FEATURE:
<223> OTHER INFORMATION: fusion protein Sp-TRAIL-ASPD_F335D

<400> SEQUENCE: 50

Met Glu Thr Asp Thr Leu Leu Leu Trp Val Leu Leu Leu Trp Val Pro
1               5                   10                  15
Ala Gly Asn Gly Gln Arg Val Ala Ala His Ile Thr Gly Thr Arg Gly
            20                  25                  30
Arg Ser Asn Thr Leu Ser Ser Pro Asn Ser Lys Asn Glu Lys Ala Leu
        35                  40                  45
Gly Arg Lys Ile Asn Ser Trp Glu Ser Ser Arg Ser Gly His Ser Phe
    50                  55                  60
Leu Ser Asn Leu His Leu Arg Asn Gly Glu Leu Val Ile His Glu Lys
65                  70                  75                  80
Gly Phe Tyr Tyr Ile Tyr Ser Gln Thr Tyr Phe Arg Phe Gln Glu Glu
                85                  90                  95
Ile Lys Glu Asn Thr Lys Asn Asp Lys Gln Met Val Gln Tyr Ile Tyr
                100                 105                 110
Lys Tyr Thr Ser Tyr Pro Asp Pro Ile Leu Leu Met Lys Ser Ala Arg
        115                 120                 125
Asn Ser Cys Trp Ser Lys Asp Ala Glu Tyr Gly Leu Tyr Ser Ile Tyr
    130                 135                 140
Gln Gly Gly Ile Phe Glu Leu Lys Glu Asn Asp Arg Ile Phe Val Ser
145                 150                 155                 160
Val Thr Asn Glu His Leu Ile Asp Met Asp His Glu Ala Ser Phe Phe
                165                 170                 175
Gly Ala Phe Leu Val Gly Ser Ser Gly Ser Ser Gly Ser Ser Gly Ser
```

```
                180             185             190
Gly Leu Pro Asp Val Ala Ser Leu Arg Gln Gln Val Glu Ala Leu Gln
            195             200             205
Gly Gln Val Gln His Leu Gln Ala Ala Phe Ser Gln Tyr Lys Lys Val
    210             215             220
Glu Leu Phe Pro Asn Gly Gln Ser Val Gly Glu Lys Ile Phe Lys Thr
225             230             235             240
Ala Gly Phe Val Lys Pro Phe Thr Glu Ala Gln Leu Leu Cys Thr Gln
            245             250             255
Ala Gly Gly Gln Leu Ala Ser Pro Arg Ser Ala Ala Glu Asn Ala Ala
        260             265             270
Leu Gln Gln Leu Val Val Ala Lys Asn Glu Ala Ala Phe Leu Ser Met
    275             280             285
Thr Asp Ser Lys Thr Glu Gly Lys Phe Thr Tyr Pro Thr Gly Glu Ser
        290             295             300
Leu Val Tyr Ser Asn Trp Ala Pro Gly Glu Pro Asn Asp Asp Gly Gly
305             310             315             320
Ser Glu Asp Cys Val Glu Ile Asp Thr Asn Gly Lys Trp Asn Asp Arg
            325             330             335
Ala Cys Gly Glu Lys Arg Leu Val Val Cys Glu Phe Gly Gly Ser Pro
        340             345             350
Ser Ser Ser Ser Ser Ala Trp Ser His Pro Gln Phe Glu Lys
    355             360             365

<210> SEQ ID NO 51
<211> LENGTH: 344
<212> TYPE: PRT
<213> ORGANISM: Artificial
<220> FEATURE:
<223> OTHER INFORMATION: fusion protein Sp-APRIL-ASPD

<400> SEQUENCE: 51

Met Glu Thr Asp Thr Leu Leu Leu Trp Val Leu Leu Leu Trp Val Pro
1               5                   10                  15
Ala Gly Asn Gly Lys Gln His Ser Val Leu His Leu Val Pro Ile Asn
            20                  25                  30
Ala Thr Ser Lys Asp Asp Ser Asp Val Thr Glu Val Met Trp Gln Pro
        35                  40                  45
Ala Leu Arg Arg Gly Arg Gly Leu Gln Ala Gln Gly Tyr Gly Val Arg
    50                  55                  60
Ile Gln Asp Ala Gly Val Tyr Leu Leu Tyr Ser Gln Val Leu Phe Gln
65                  70                  75                  80
Asp Val Thr Phe Thr Met Gly Gln Val Val Ser Arg Glu Gly Gln Gly
                85                  90                  95
Arg Gln Glu Thr Leu Phe Arg Cys Ile Arg Ser Met Pro Ser His Pro
            100                 105                 110
Asp Arg Ala Tyr Asn Ser Cys Tyr Ser Ala Gly Val Phe His Leu His
        115                 120                 125
Gln Gly Asp Ile Leu Ser Val Ile Ile Pro Arg Ala Arg Ala Lys Leu
    130                 135                 140
Asn Leu Ser Pro His Gly Thr Phe Leu Gly Phe Val Lys Leu Gly Ser
145                 150                 155                 160
Ser Gly Ser Ser Gly Ser Ser Gly Ser Gly Leu Pro Asp Val Ala Ser
                165                 170                 175
Leu Arg Gln Gln Val Glu Ala Leu Gln Gly Gln Val Gln His Leu Gln
```

```
                180                 185                 190
Ala Ala Phe Ser Gln Tyr Lys Lys Val Glu Leu Phe Pro Asn Gly Gln
            195                 200                 205

Ser Val Gly Glu Lys Ile Phe Lys Thr Ala Gly Phe Val Lys Pro Phe
            210                 215                 220

Thr Glu Ala Gln Leu Leu Cys Thr Gln Ala Gly Gly Gln Leu Ala Ser
225                 230                 235                 240

Pro Arg Ser Ala Ala Glu Asn Ala Ala Leu Gln Gln Leu Val Val Ala
                245                 250                 255

Lys Asn Glu Ala Ala Phe Leu Ser Met Thr Asp Ser Lys Thr Glu Gly
                260                 265                 270

Lys Phe Thr Tyr Pro Thr Gly Glu Ser Leu Val Tyr Ser Asn Trp Ala
            275                 280                 285

Pro Gly Glu Pro Asn Asp Asp Gly Gly Ser Glu Asp Cys Val Glu Ile
            290                 295                 300

Phe Thr Asn Gly Lys Trp Asn Asp Arg Ala Cys Gly Glu Lys Arg Leu
305                 310                 315                 320

Val Val Cys Glu Phe Gly Gly Ser Pro Ser Ser Ser Ser Ser Ser Ala
                325                 330                 335

Trp Ser His Pro Gln Phe Glu Lys
            340

<210> SEQ ID NO 52
<211> LENGTH: 9
<212> TYPE: PRT
<213> ORGANISM: Artificial
<220> FEATURE:
<223> OTHER INFORMATION: FLAG-epitope/enterokinase-processing site

<400> SEQUENCE: 52

Asp Tyr Lys Asp Asp Asp Asp Lys Asp
1               5

<210> SEQ ID NO 53
<211> LENGTH: 9
<212> TYPE: PRT
<213> ORGANISM: Artificial
<220> FEATURE:
<223> OTHER INFORMATION: flexible linker element
<220> FEATURE:
<221> NAME/KEY: REPEAT
<222> LOCATION: (1)..(3)
<223> OTHER INFORMATION: 0,1,2,3,4,5 or 6
<220> FEATURE:
<221> NAME/KEY: REPEAT
<222> LOCATION: (4)..(6)
<223> OTHER INFORMATION: 0,1,2,3,4,5 or 6
<220> FEATURE:
<221> NAME/KEY: REPEAT
<222> LOCATION: (7)..(9)
<223> OTHER INFORMATION: 0,1,2,3,4,5 or 6

<400> SEQUENCE: 53

Gly Ser Ser Ser Ser Gly Gly Ser Gly
1               5

<210> SEQ ID NO 54
<211> LENGTH: 11
<212> TYPE: PRT
<213> ORGANISM: Artificial
<220> FEATURE:
<223> OTHER INFORMATION: linker A

<400> SEQUENCE: 54
```

```
Gly Ser Ser Gly Ser Ser Gly Ser Ser Gly Ser
1               5                   10

<210> SEQ ID NO 55
<211> LENGTH: 8
<212> TYPE: PRT
<213> ORGANISM: Artificial
<220> FEATURE:
<223> OTHER INFORMATION: linker B

<400> SEQUENCE: 55

Gly Ser Ser Gly Ser Ser Gly Ser
1               5

<210> SEQ ID NO 56
<211> LENGTH: 5
<212> TYPE: PRT
<213> ORGANISM: Artificial
<220> FEATURE:
<223> OTHER INFORMATION: linker C

<400> SEQUENCE: 56

Gly Ser Ser Gly Ser
1               5

<210> SEQ ID NO 57
<211> LENGTH: 2
<212> TYPE: PRT
<213> ORGANISM: Artificial
<220> FEATURE:
<223> OTHER INFORMATION: linker D

<400> SEQUENCE: 57

Gly Ser
1

<210> SEQ ID NO 58
<211> LENGTH: 8
<212> TYPE: PRT
<213> ORGANISM: Artificial
<220> FEATURE:
<223> OTHER INFORMATION: Strep-tag II

<400> SEQUENCE: 58

Trp Ser His Pro Gln Phe Glu Lys
1               5

<210> SEQ ID NO 59
<211> LENGTH: 8
<212> TYPE: PRT
<213> ORGANISM: Artificial
<220> FEATURE:
<223> OTHER INFORMATION: flexible linker element

<400> SEQUENCE: 59

Pro Ser Ser Ser Ser Ser Ser Ala
1               5

<210> SEQ ID NO 60
<211> LENGTH: 11
<212> TYPE: PRT
<213> ORGANISM: Artificial
<220> FEATURE:
<223> OTHER INFORMATION: linker element

<400> SEQUENCE: 60
```

```
Gly Gly Ser Pro Ser Ser Ser Ser Ser Ala
1               5                   10

<210> SEQ ID NO 61
<211> LENGTH: 10
<212> TYPE: PRT
<213> ORGANISM: Artificial
<220> FEATURE:
<223> OTHER INFORMATION: linker element

<400> SEQUENCE: 61

Gly Ser Pro Ser Ser Ser Ser Ser Ser Ala
1               5                   10

<210> SEQ ID NO 62
<211> LENGTH: 9
<212> TYPE: PRT
<213> ORGANISM: Artificial
<220> FEATURE:
<223> OTHER INFORMATION: linker element

<400> SEQUENCE: 62

Gly Pro Ser Ser Ser Ser Ser Ser Ala
1               5
```